US011584785B2

(12) United States Patent
Doerner et al.

(10) Patent No.: US 11,584,785 B2
(45) Date of Patent: Feb. 21, 2023

(54) C-PEPTIDES AND PROINSULIN POLYPEPTIDES COMPRISING THE SAME

(71) Applicant: ABSCI, LLC, Vancouver, WA (US)

(72) Inventors: Amy Doerner, Vancouver, WA (US); Michael Cammarata, Vancouver, WA (US); Tyler Nusca, Portland, OR (US); Suzanne A. Sprunger, Port Ludlow, WA (US); Melissa Patterson, Portland, OR (US)

(73) Assignee: ABSCI, LLC, Vancouver, WA (US)

( * ) Notice: Subject to any disclaimer, the term of this patent is extended or adjusted under 35 U.S.C. 154(b) by 0 days.

(21) Appl. No.: 16/866,361

(22) Filed: May 4, 2020

(65) Prior Publication Data

US 2020/0299343 A1 Sep. 24, 2020

Related U.S. Application Data

(63) Continuation of application No. PCT/US2019/052998, filed on Sep. 25, 2019.

(60) Provisional application No. 62/735,861, filed on Sep. 25, 2018.

(51) Int. Cl.

| | |
|---|---|
| ***C07K 14/47*** | (2006.01) |
| ***C07K 14/62*** | (2006.01) |
| ***C12N 9/48*** | (2006.01) |
| ***C12N 9/96*** | (2006.01) |

(52) U.S. Cl.

CPC .............. *C07K 14/47* (2013.01); *C07K 14/62* (2013.01); *C12N 9/485* (2013.01); *C12N 9/96* (2013.01); *C12Y 304/17002* (2013.01); *C07K 2319/00* (2013.01)

(58) Field of Classification Search

None

See application file for complete search history.

(56) References Cited

U.S. PATENT DOCUMENTS

| | | | |
|---|---|---|---|
| 9,617,335 | B2 | 4/2017 | McClain et al. |
| 2015/0353940 | A1 | 12/2015 | McClain et al. |

FOREIGN PATENT DOCUMENTS

| | | | |
|---|---|---|---|
| WO | WO-2001/00245 | A2 | 1/2001 |
| WO | WO-2009/089154 | A2 | 7/2009 |
| WO | WO 2012/115638 | | 8/2012 |
| WO | WO 2013/168178 | | 11/2013 |
| WO | WO-2014/025663 | A1 | 2/2014 |
| WO | WO-2016/205570 | A1 | 12/2016 |
| WO | WO 2017/106583 | | 6/2017 |

OTHER PUBLICATIONS

Nguyen et al., "Pre-expression of a sulfhydryl oxidase significantly increases the yields of eukaryotic disulfide bond containing proteins expressed in the cytoplasm of *E. coli," Microbial Cell Factories*, 10:1, 2011 (13 pages).

Amet et al., Insertion of the designed helical linker led to increased expression of Tf-based fusion proteins, *Pharm. Res. Mar.* 26(3): 523-528 (2009).

Chang et al., Human insulin production from a novel mini-proinsulin which has high receptor-binding activity, *Biochem. J.* 329(Pt 3): 631-635 (1998).

Chung et al., Recombinant production of biologically active giant grouper (*Epinephelus lanceolatus*) growth hormone from inclusion bodies of Escherichia coli by fed-batch culture, *Protein Expr. Purif.* 110: 79-88 (2015).

Coll et al., Three-dimensional structure of porcine procarboxypeptidase B: a structural basis of its inactivity, *EMBO. J.* 10(1): 1-9 (1991).

Cube Biotech, "Screening detergents for optimal solubilization and purification of membrane proteins", 2013, retrieved from www.cube-biotech.com/files/protocols/Screening_Detergents.pdf www.cube-biotech.com/files/protocols/Screening_Detergents.pdf> on Mar. 29, 2017.

Datsenko et al., One-step inactivation of chromosomal genes in Escherichia colt K-12 using PCR products, *Proc. Natl. Acad. Sci. U.S.A.* 97(12): 6640-6645 (2000).

De Mey et al., Promoter knock-in: a novel rational method for the fine tuning of genes, *BMC Biotechnol.* 10: 26 (2010).

Farr et al., Oxidative stress responses in Escherichia coli and Salmonella typhimurium, *Microbiol. Rev.* 55(4): 561-585 (1991).

Faulkner et al., Functional plasticity of a peroxidase allows evolution of diverse disulfide-reducing pathways, *Proc. Natl. Acad. Sci. U.S.A.* 105(18): 6735-6740 (2008).

Khlebnikov et al., Regulatable arabinose-inducible gene expression system with consistent control in all cells of a culture, *J. Bacteriol.* 182(24): 7029-7034 (2000).

Kikuchi et al., The nucleotide sequence of the promoter and the amino-terminal region of alkaline phosphatase structural gene (phoA) of *Escherichia coli*, *Nucleic Acids Res.* 9(21): 5671-5678 (1981).

Lobstein et al., SHuffle, a novel *Escherichia coli* protein expression strain capable of correctly folding disulfide bonded proteins in its cytoplasm, *Microb. Cell Fact.*11: 56 (2012).

Majewski et al., Simple constrained-optimization view of acetate overflow in *E. coli, Biotechnol. Bioeng.* 35(7): 732-738 (1990).

Makino et al., Strain engineering for improved expression of recombinant proteins in bacteria, *Microb. Cell Fact.* 14; 10: 32 (2011).

(Continued)

*Primary Examiner* — Anand U Desai

(74) *Attorney, Agent, or Firm* — Marshall, Gerstein & Borun LLP

(57) ABSTRACT

A connecting polypeptide has SEQ ID NO:73. A proinsulin polypeptide includes a mature insulin A-chain, a mature insulin B-chain, and a connecting peptide comprising SEQ ID NO: 73 linking the mature A-chain and the mature B-chain, wherein the connecting peptide is not a native human proinsulin C-peptide. The proinsulin polypeptides according to the invention can be made in high titers and in high purity.

20 Claims, 5 Drawing Sheets

Specification includes a Sequence Listing.

(56) References Cited

OTHER PUBLICATIONS

Man et al., Artificial trans-encoded small non-coding RNAs specifically silence the selected gene expression in bacteria, *Nucleic Acids Res*. 39(8): e50 (2011).
Morgan-Kiss et al., Long-term and homogeneous regulation of the Escherichia coli araBAD promoter by use of a lactose transporter of relaxed specificity, *Proc. Natl. Acad. Sci. U.S.A*. 99(11): 7373-7377 (2002).
Muyrers et al., Rapid modification of bacterial artificial chromosomes by ET-recombination, *Nucleic Acids Res*. 27(6): 1555-1557 (1999).
NCBI Accession No. NC 000913.2, *Escherichia coli* str. K-12 substr. MG1655, complete genome, Mar. 9, 2022.
NCBI Accession No. NC 000913.3, *Escherichia coli* str. K-12 substr. MG1655, complete genome, Mar. 9, 2022.
NCBI Accession No. NP 001278826.1, insulin preproprotein [*Homo sapiens*], Feb. 2022.
Needleman et al., A general method applicable to the search for similarities in the amino acid sequence of two proteins, *J. Mol. Biol*. 48:443 (1970).
Nili et al., Defining the disulfide bonds of insulin-like growth factor-binding protein-5 by tandem mass spectrometry with electron transfer dissociation and collision-induced dissociation, *J. Biol. Chem*. 287(2): 1510-1519 (2012).
Notenboom et al., Crystal structures of the family 9 carbohydrate-binding module from *Thermotoga maritima* xylanase 10A in native and ligand-bound forms, *Biochemistry*. 40(21): 6248-6256 (2001).
Schoenfeld, "Convenient, rapid enrichment of periplasmic and spheroplasmic protein fractions using the new PeriPrepsTM Periplasting Kit", Epicentre Forum 1998 5(1): 5; available at epibio.com/docs/default-source/forum-archive/forum-05-1—convenient-rapid-enrichment-of-periplasmic-and-epibio.com/docs/default-source/forum-archive/forum-05-1—convenient-rapid-enrichment-of-periplasmic-and->spheropl asmic-protein-fractions-using-the-new-periprep s-periplasting-kit.pdf.
Song et al., Organization and regulation of the D-xylose operons in *Escherichia coli* K-12: XylR acts as a transcriptional activator, *J. Bacteriol*. 179(22): 7025-7032 (1997).
Wickstrum et al., The AraC/XylS family activator RhaS negatively autoregulates *rhaSR* expression by preventing cyclic AMP receptor protein activation, *J. Bacteriol*. 192(1): 225-232 (2010).
Yamaguchi et al., Refolding techniques for recovering biologically active recombinant proteins from inclusion bodies, *Biomolecules*. 4(1): 235-251 (2014).

Purified Proglargine

Digest with Trypsin,
and then digest with Glu-C

Predicted Peptide Fragments:

2 disulfide bonds:

(SEQ ID NO:89)
FVNQHLCGSHLVE
|
QCCTSICSLYQLE
(SEQ ID NO:88)

1 disulfide bond:

(SEQ ID NO:91)
ALYLVCGE
|
NYCG
(SEQ ID NO:90)

Characterize peptide fragments by mass spectrometry

SEQUENCE LISTING

<160> NUMBER OF SEQ ID NOS: 74

<210> SEQ ID NO 1
<211> LENGTH: 21
<212> TYPE: PRT
<213> ORGANISM: Homo sapiens

<400> SEQUENCE: 1

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 2
<211> LENGTH: 30
<212> TYPE: PRT
<213> ORGANISM: Homo sapiens

<400> SEQUENCE: 2

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

<210> SEQ ID NO 3
<211> LENGTH: 30
<212> TYPE: PRT
<213> ORGANISM: Artificial Sequence
<220> FEATURE:
<223> OTHER INFORMATION: Insulin lispro, B chain

<400> SEQUENCE: 3

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 4
<211> LENGTH: 30
<212> TYPE: PRT
<213> ORGANISM: Artificial Sequence
<220> FEATURE:
<223> OTHER INFORMATION: Insulin aspart, B chain

<400> SEQUENCE: 4

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30
```

<210> SEQ ID NO 5
<211> LENGTH: 30
<212> TYPE: PRT
<213> ORGANISM: Artificial Sequence
<220> FEATURE:
<223> OTHER INFORMATION: Insulin glulisine, B chain

<400> SEQUENCE: 5

```
Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```

-continued

```
<210> SEQ ID NO 6
<211> LENGTH: 21
<212> TYPE: PRT
<213> ORGANISM: Artificial Sequence
<220> FEATURE:
<223> OTHER INFORMATION: Insulin glargine, A chain

<400> SEQUENCE: 6

Gly Ile Val Glu Gln Cys Cys Thr Ser Ile Cys Ser Leu Tyr Gln Leu
1               5                   10                  15

Glu Asn Tyr Cys Gly
            20


<210> SEQ ID NO 7
<211> LENGTH: 32
<212> TYPE: PRT
<213> ORGANISM: Artificial Sequence
<220> FEATURE:
<223> OTHER INFORMATION: Insulin glargine, B chain

<400> SEQUENCE: 7

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30


<210> SEQ ID NO 8
<211> LENGTH: 29
<212> TYPE: PRT
<213> ORGANISM: Artificial Sequence
<220> FEATURE:
<223> OTHER INFORMATION: Insulin degludec, B chain; modification of
      lysine at B29 with a hexadecanedioic acid molecule bound to B29
      through an L-gamma-Glu linker

<400> SEQUENCE: 8

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25


<210> SEQ ID NO 9
<211> LENGTH: 29
<212> TYPE: PRT
<213> ORGANISM: Artificial Sequence
<220> FEATURE:
<223> OTHER INFORMATION: Insulin detemir, B chain; modification of
      lysine at B29 with a myristic acid molecule

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25


<210> SEQ ID NO 10
<211> LENGTH: 35
<212> TYPE: PRT
<213> ORGANISM: Homo sapiens

<400> SEQUENCE: 10

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30
```

```
Gln Lys Arg
        35


<210> SEQ ID NO 11
<211> LENGTH: 9
<212> TYPE: PRT
<213> ORGANISM: Artificial Sequence
<220> FEATURE:
<223> OTHER INFORMATION: Artificial C-peptide

<400> SEQUENCE: 11

Arg Arg Tyr Pro Gly Asp Val Lys Arg
1               5


<210> SEQ ID NO 12
<211> LENGTH: 34
<212> TYPE: PRT
<213> ORGANISM: Artificial Sequence
<220> FEATURE:
<223> OTHER INFORMATION: Artificial variant of the human C-peptide

<400> SEQUENCE: 12

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Arg


<210> SEQ ID NO 13
<211> LENGTH: 25
<212> TYPE: PRT
<213> ORGANISM: Artificial Sequence
<220> FEATURE:
<223> OTHER INFORMATION: Artificial variant of the human C-peptide

<400> SEQUENCE: 13

Arg Arg Glu Ala Glu Asp Leu Gln Val Gly Gln Val Glu Leu Gly Gly
1               5                   10                  15

Gly Pro Gly Ala Gly Ser Leu Gln Arg
            20                  25


<210> SEQ ID NO 14
<211> LENGTH: 8
<212> TYPE: PRT
<213> ORGANISM: Artificial Sequence
<220> FEATURE:
<223> OTHER INFORMATION: Artificial C-peptide

<400> SEQUENCE: 14

Arg Arg Asp Asp Asn Leu Glu Arg
1               5


<210> SEQ ID NO 15
<211> LENGTH: 147
<212> TYPE: PRT
<213> ORGANISM: Artificial Sequence
<220> FEATURE:
<223> OTHER INFORMATION: Metreleptin

<400> SEQUENCE: 15

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30
```

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 16
<211> LENGTH: 168
<212> TYPE: PRT
<213> ORGANISM: Hog cholera virus (strain Alfort)

<400> SEQUENCE: 16

Met Glu Leu Asn His Phe Glu Leu Leu Tyr Lys Thr Ser Lys Gln Lys
1               5                   10                  15

Pro Val Gly Val Glu Glu Pro Val Tyr Asp Thr Ala Gly Arg Pro Leu
            20                  25                  30

Phe Gly Asn Pro Ser Glu Val His Pro Gln Ser Thr Leu Lys Leu Pro
        35                  40                  45

His Asp Arg Gly Arg Gly Asp Ile Arg Thr Thr Leu Arg Asp Leu Pro
    50                  55                  60

Arg Lys Gly Asp Cys Arg Ser Gly Asn His Leu Gly Pro Val Ser Gly
65                  70                  75                  80

Ile Tyr Ile Lys Pro Gly Pro Val Tyr Tyr Gln Asp Tyr Thr Gly Pro
                85                  90                  95

Val Tyr His Arg Ala Pro Leu Glu Phe Phe Asp Glu Ala Gln Phe Cys
            100                 105                 110

Glu Val Thr Lys Arg Ile Gly Arg Val Thr Gly Ser Asp Gly Lys Leu
        115                 120                 125

Tyr His Ile Tyr Val Cys Val Asp Gly Cys Ile Leu Leu Lys Leu Ala
    130                 135                 140

Lys Arg Gly Thr Pro Arg Thr Leu Lys Trp Ile Arg Asn Phe Thr Asn
145                 150                 155                 160

Cys Pro Leu Trp Val Thr Ser Cys
                165

<210> SEQ ID NO 17
<211> LENGTH: 91
<212> TYPE: PRT
<213> ORGANISM: Caenorhabditis elegans

<400> SEQUENCE: 17

Met Ala Asp Asp Ala Ala Gln Ala Gly Asp Asn Ala Glu Tyr Ile Lys
1               5                   10                  15

Ile Lys Val Val Gly Gln Asp Ser Asn Glu Val His Phe Arg Val Lys
            20                  25                  30

```
Tyr Gly Thr Ser Met Ala Lys Leu Lys Lys Ser Tyr Ala Asp Arg Thr
        35                  40                  45

Gly Val Ala Val Asn Ser Leu Arg Phe Leu Phe Asp Gly Arg Arg Ile
    50                  55                  60

Asn Asp Asp Asp Thr Pro Lys Thr Leu Glu Met Glu Asp Asp Asp Val
65                  70                  75                  80

Ile Glu Val Tyr Gln Glu Gln Leu Gly Gly Phe
                85                  90


<210> SEQ ID NO 18
<211> LENGTH: 26
<212> TYPE: PRT
<213> ORGANISM: Artificial Sequence
<220> FEATURE:
<223> OTHER INFORMATION: Linker polypeptide

<400> SEQUENCE: 18

Leu Glu Ala Glu Ala Ala Ala Lys Glu Ala Ala Ala Lys Glu Ala Ala
1               5                   10                  15

Ala Lys Glu Ala Ala Ala Lys Ala Leu Glu
            20                  25


<210> SEQ ID NO 19
<211> LENGTH: 50
<212> TYPE: PRT
<213> ORGANISM: Artificial Sequence
<220> FEATURE:
<223> OTHER INFORMATION: Linker polypeptide

<400> SEQUENCE: 19

Leu Glu Ala Glu Ala Ala Ala Lys Glu Ala Ala Ala Lys Glu Ala Ala
1               5                   10                  15

Ala Lys Glu Ala Ala Ala Lys Ala Leu Glu Ala Glu Ala Ala Ala Lys
            20                  25                  30

Glu Ala Ala Ala Lys Glu Ala Ala Ala Lys Glu Ala Ala Ala Lys Ala
        35                  40                  45

Leu Glu
    50


<210> SEQ ID NO 20
<211> LENGTH: 7
<212> TYPE: PRT
<213> ORGANISM: Artificial Sequence
<220> FEATURE:
<223> OTHER INFORMATION: Acid-cleavable amino acid sequence

<400> SEQUENCE: 20

Gly Gly Asp Pro Gly Gly Gly
1               5


<210> SEQ ID NO 21
<211> LENGTH: 8
<212> TYPE: PRT
<213> ORGANISM: Artificial Sequence
<220> FEATURE:
<223> OTHER INFORMATION: TEV (tobacco etch virus) protease cleavage site

<400> SEQUENCE: 21

Glu Asn Leu Tyr Phe Gln Gly Gly
1               5


<210> SEQ ID NO 22
```

-continued

<211> LENGTH: 6
<212> TYPE: PRT
<213> ORGANISM: Artificial Sequence
<220> FEATURE:
<223> OTHER INFORMATION: Enterokinase cleavage site

<400> SEQUENCE: 22

```
Asp Asp Asp Asp Lys Gly
1               5
```

<210> SEQ ID NO 23
<211> LENGTH: 6
<212> TYPE: PRT
<213> ORGANISM: Artificial Sequence
<220> FEATURE:
<223> OTHER INFORMATION: Thrombin cleavage site

<400> SEQUENCE: 23

```
Leu Val Pro Arg Gly Ser
1               5
```

<210> SEQ ID NO 24
<211> LENGTH: 396
<212> TYPE: PRT
<213> ORGANISM: Escherichia coli

<400> SEQUENCE: 24

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Gly Lys
            20                  25                  30

Leu Val Ile Trp Ile Asn Gly Asp Lys Gly Tyr Asn Gly Leu Ala Glu
        35                  40                  45

Val Gly Lys Lys Phe Glu Lys Asp Thr Gly Ile Lys Val Thr Val Glu
    50                  55                  60

His Pro Asp Lys Leu Glu Glu Lys Phe Pro Gln Val Ala Ala Thr Gly
65                  70                  75                  80

Asp Gly Pro Asp Ile Ile Phe Trp Ala His Asp Arg Phe Gly Gly Tyr
                85                  90                  95

Ala Gln Ser Gly Leu Leu Ala Glu Ile Thr Pro Asp Lys Ala Phe Gln
            100                 105                 110

Asp Lys Leu Tyr Pro Phe Thr Trp Asp Ala Val Arg Tyr Asn Gly Lys
        115                 120                 125

Leu Ile Ala Tyr Pro Ile Ala Val Glu Ala Leu Ser Leu Ile Tyr Asn
    130                 135                 140

Lys Asp Leu Leu Pro Asn Pro Pro Lys Thr Trp Glu Glu Ile Pro Ala
145                 150                 155                 160

Leu Asp Lys Glu Leu Lys Ala Lys Gly Lys Ser Ala Leu Met Phe Asn
                165                 170                 175

Leu Gln Glu Pro Tyr Phe Thr Trp Pro Leu Ile Ala Ala Asp Gly Gly
            180                 185                 190

Tyr Ala Phe Lys Tyr Glu Asn Gly Lys Tyr Asp Ile Lys Asp Val Gly
        195                 200                 205

Val Asp Asn Ala Gly Ala Lys Ala Gly Leu Thr Phe Leu Val Asp Leu
    210                 215                 220

Ile Lys Asn Lys His Met Asn Ala Asp Thr Asp Tyr Ser Ile Ala Glu
225                 230                 235                 240

Ala Ala Phe Asn Lys Gly Glu Thr Ala Met Thr Ile Asn Gly Pro Trp
                245                 250                 255
```

```
Ala Trp Ser Asn Ile Asp Thr Ser Lys Val Asn Tyr Gly Val Thr Val
            260                 265                 270

Leu Pro Thr Phe Lys Gly Gln Pro Ser Lys Pro Phe Val Gly Val Leu
        275                 280                 285

Ser Ala Gly Ile Asn Ala Ala Ser Pro Asn Lys Glu Leu Ala Lys Glu
    290                 295                 300

Phe Leu Glu Asn Tyr Leu Leu Thr Asp Glu Gly Leu Glu Ala Val Asn
305                 310                 315                 320

Lys Asp Lys Pro Leu Gly Ala Val Ala Leu Lys Ser Tyr Glu Glu Glu
                325                 330                 335

Leu Ala Lys Asp Pro Arg Ile Ala Ala Thr Met Glu Asn Ala Gln Lys
            340                 345                 350

Gly Glu Ile Met Pro Asn Ile Pro Gln Met Ser Ala Phe Trp Tyr Ala
        355                 360                 365

Val Arg Thr Ala Val Ile Asn Ala Ala Ser Gly Arg Gln Thr Val Asp
    370                 375                 380

Glu Ala Leu Lys Asp Ala Gln Thr Arg Ile Thr Lys
385                 390                 395


<210> SEQ ID NO 25
<211> LENGTH: 169
<212> TYPE: PRT
<213> ORGANISM: Thermotoga maritima

<400> SEQUENCE: 25

Lys Glu Ser Arg Ile Ser Glu Gly Glu Ala Val Val Val Gly Met Met
1               5                   10                  15

Asp Asp Ser Tyr Leu Met Ser Lys Pro Ile Glu Ile Leu Asp Glu Glu
            20                  25                  30

Gly Asn Val Lys Ala Thr Ile Arg Ala Val Trp Lys Asp Ser Thr Ile
        35                  40                  45

Tyr Ile Tyr Gly Glu Val Gln Asp Lys Thr Lys Lys Pro Ala Glu Asp
    50                  55                  60

Gly Val Ala Ile Phe Ile Asn Pro Asn Asn Glu Arg Thr Pro Tyr Leu
65                  70                  75                  80

Gln Pro Asp Asp Thr Tyr Ala Val Leu Trp Thr Asn Trp Lys Thr Glu
                85                  90                  95

Val Asn Arg Glu Asp Val Gln Val Lys Lys Phe Val Gly Pro Gly Phe
            100                 105                 110

Arg Arg Tyr Ser Phe Glu Met Ser Ile Thr Ile Pro Gly Val Glu Phe
        115                 120                 125

Lys Lys Asp Ser Tyr Ile Gly Phe Asp Ala Ala Val Ile Asp Asp Gly
    130                 135                 140

Lys Trp Tyr Ser Trp Ser Asp Thr Thr Asn Ser Gln Lys Thr Asn Thr
145                 150                 155                 160

Met Asn Tyr Gly Thr Leu Lys Leu Glu
                165


<210> SEQ ID NO 26
<211> LENGTH: 95
<212> TYPE: PRT
<213> ORGANISM: Homo sapiens

<400> SEQUENCE: 26

His His Gly Gly Glu His Phe Glu Gly Glu Lys Val Phe Arg Val Asn
1               5                   10                  15
```

Val Glu Asp Glu Asn His Ile Asn Ile Ile Arg Glu Leu Ala Ser Thr
20 25 30

Thr Gln Ile Asp Phe Trp Lys Pro Asp Ser Val Thr Gln Ile Lys Pro
35 40 45

His Ser Thr Val Asp Phe Arg Val Lys Ala Glu Asp Thr Val Thr Val
50 55 60

Glu Asn Val Leu Lys Gln Asn Glu Leu Gln Tyr Lys Val Leu Ile Ser
65 70 75 80

Asn Leu Arg Asn Val Val Glu Ala Gln Phe Asp Ser Arg Val Arg
85 90 95

<210> SEQ ID NO 27
<211> LENGTH: 44
<212> TYPE: PRT
<213> ORGANISM: Artificial Sequence
<220> FEATURE:
<223> OTHER INFORMATION: Carboxypeptidase B propeptide variant

<400> SEQUENCE: 27

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Glu Val Arg
35 40

<210> SEQ ID NO 28
<211> LENGTH: 51
<212> TYPE: PRT
<213> ORGANISM: Artificial Sequence
<220> FEATURE:
<223> OTHER INFORMATION: Carboxypeptidase B propeptide variant

<400> SEQUENCE: 28

Met His His Ser Gly Glu His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Val Glu Asp Phe Glu Leu Asp
35 40 45

Arg Val Arg
50

<210> SEQ ID NO 29
<211> LENGTH: 51
<212> TYPE: PRT
<213> ORGANISM: Artificial Sequence
<220> FEATURE:
<223> OTHER INFORMATION: Carboxypeptidase B propeptide variant

<400> SEQUENCE: 29

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Val Glu Asp Phe Glu Leu Asp
35 40 45

Arg Val Arg
50

<210> SEQ ID NO 30
<211> LENGTH: 53
<212> TYPE: PRT
<213> ORGANISM: Artificial Sequence
<220> FEATURE:
<223> OTHER INFORMATION: Carboxypeptidase B propeptide variant

<400> SEQUENCE: 30

```
Met His His Ser Gly Glu His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Val Glu Asp Phe Glu Leu Gln
        35                  40                  45

Asp Ser Arg Val Arg
    50
```

<210> SEQ ID NO 31
<211> LENGTH: 53
<212> TYPE: PRT
<213> ORGANISM: Artificial Sequence
<220> FEATURE:
<223> OTHER INFORMATION: Carboxypeptidase B propeptide variant

<400> SEQUENCE: 31

```
Met His His His His His His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Val Glu Asp Phe Glu Leu Gln
        35                  40                  45

Asp Ser Arg Val Arg
    50
```

<210> SEQ ID NO 32
<211> LENGTH: 58
<212> TYPE: PRT
<213> ORGANISM: Artificial Sequence
<220> FEATURE:
<223> OTHER INFORMATION: Carboxypeptidase B propeptide variant

<400> SEQUENCE: 32

```
Met His His Ser Gly Glu His Glu Lys Val Phe Arg Val Glu Asn Asp
1               5                   10                  15

Ile Ser Leu His Glu Leu Ala Ser Thr Gln Ile Asp Phe Trp Lys Pro
            20                  25                  30

Asp Ile His Val Asp Phe Arg Val Lys Ala Glu Asp Leu Val Glu Asp
        35                  40                  45

Phe Leu Glu Gln Glu Leu Gln Arg Val Arg
    50                  55
```

<210> SEQ ID NO 33
<211> LENGTH: 48
<212> TYPE: PRT
<213> ORGANISM: Artificial Sequence
<220> FEATURE:
<223> OTHER INFORMATION: Carboxypeptidase B propeptide variant with
acid-cleavable Asp-Pro sequence

<400> SEQUENCE: 33

```
Met His His His His His His Glu Val Phe Val Glu Asn Asp Ile Ser
1               5                   10                  15
```

Leu His Glu Leu Ala Ser Thr Gln Ile Asp Phe Trp Pro Asp Ile Glu
20 25 30

Val Asp Phe Arg Val Lys Ala Glu Asp Glu Val Asp Pro Asp Pro Arg
35 40 45

<210> SEQ ID NO 34
<211> LENGTH: 48
<212> TYPE: PRT
<213> ORGANISM: Artificial Sequence
<220> FEATURE:
<223> OTHER INFORMATION: Carboxypeptidase B propeptide variant with acid-cleavable Asp-Pro sequence

<400> SEQUENCE: 34

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Glu Val Gly Asp Pro Gly Arg
35 40 45

<210> SEQ ID NO 35
<211> LENGTH: 51
<212> TYPE: PRT
<213> ORGANISM: Artificial Sequence
<220> FEATURE:
<223> OTHER INFORMATION: Carboxypeptidase B propeptide variant with acid-cleavable Asp-Pro sequence

<400> SEQUENCE: 35

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Glu Val Gly Gly Asp Pro Gly
35 40 45

Gly Gly Arg
50

<210> SEQ ID NO 36
<211> LENGTH: 18
<212> TYPE: PRT
<213> ORGANISM: Artificial Sequence
<220> FEATURE:
<223> OTHER INFORMATION: Carboxypeptidase B propeptide variant

<400> SEQUENCE: 36

Met His His His His His His Glu Val Phe Val Glu Asn Asp Ile Ser
1 5 10 15

Leu Arg

<210> SEQ ID NO 37
<211> LENGTH: 8
<212> TYPE: PRT
<213> ORGANISM: Artificial Sequence
<220> FEATURE:
<223> OTHER INFORMATION: Artificial propeptide

<400> SEQUENCE: 37

Met His His His His His His Arg
1 5

<210> SEQ ID NO 38
<211> LENGTH: 189
<212> TYPE: PRT
<213> ORGANISM: Saccharomyces cerevisiae

<400> SEQUENCE: 38

```
Met Lys Ala Ile Asp Lys Met Thr Asp Asn Pro Pro Gln Glu Gly Leu
1               5                   10                  15

Ser Gly Arg Lys Ile Ile Tyr Asp Glu Asp Gly Lys Pro Cys Arg Ser
            20                  25                  30

Cys Asn Thr Leu Leu Asp Phe Gln Tyr Val Thr Gly Lys Ile Ser Asn
        35                  40                  45

Gly Leu Lys Asn Leu Ser Ser Asn Gly Lys Leu Ala Gly Thr Gly Ala
    50                  55                  60

Leu Thr Gly Glu Ala Ser Glu Leu Met Pro Gly Ser Arg Thr Tyr Arg
65                  70                  75                  80

Lys Val Asp Pro Pro Asp Val Glu Gln Leu Gly Arg Ser Ser Trp Thr
                85                  90                  95

Leu Leu His Ser Val Ala Ala Ser Tyr Pro Ala Gln Pro Thr Asp Gln
            100                 105                 110

Gln Lys Gly Glu Met Lys Gln Phe Leu Asn Ile Phe Ser His Ile Tyr
        115                 120                 125

Pro Cys Asn Trp Cys Ala Lys Asp Phe Glu Lys Tyr Ile Arg Glu Asn
    130                 135                 140

Ala Pro Gln Val Glu Ser Arg Glu Glu Leu Gly Arg Trp Met Cys Glu
145                 150                 155                 160

Ala His Asn Lys Val Asn Lys Lys Leu Arg Lys Pro Lys Phe Asp Cys
                165                 170                 175

Asn Phe Trp Glu Lys Arg Trp Lys Asp Gly Trp Asp Glu
            180                 185
```

<210> SEQ ID NO 39
<211> LENGTH: 191
<212> TYPE: PRT
<213> ORGANISM: Artificial Sequence
<220> FEATURE:
<223> OTHER INFORMATION: CPBpro variant attached to N-terminus of metreleptin

<400> SEQUENCE: 39

```
Met His His His His His His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Glu Val Arg Met Val Pro Ile
        35                  40                  45

Gln Lys Val Gln Asp Asp Thr Lys Thr Leu Ile Lys Thr Ile Val Thr
    50                  55                  60

Arg Ile Asn Asp Ile Ser His Thr Gln Ser Val Ser Ser Lys Gln Lys
65                  70                  75                  80

Val Thr Gly Leu Asp Phe Ile Pro Gly Leu His Pro Ile Leu Thr Leu
                85                  90                  95

Ser Lys Met Asp Gln Thr Leu Ala Val Tyr Gln Gln Ile Leu Thr Ser
            100                 105                 110

Met Pro Ser Arg Asn Val Ile Gln Ile Ser Asn Asp Leu Glu Asn Leu
        115                 120                 125

Arg Asp Leu Leu His Val Leu Ala Phe Ser Lys Ser Cys His Leu Pro
```

```
130 135 140

Trp Ala Ser Gly Leu Glu Thr Leu Asp Ser Leu Gly Gly Val Leu Glu
145 150 155 160

Ala Ser Gly Tyr Ser Thr Glu Val Val Ala Leu Ser Arg Leu Gln Gly
165 170 175

Ser Leu Gln Asp Met Leu Trp Gln Leu Asp Leu Ser Pro Gly Cys
180 185 190


<210> SEQ ID NO 40
<211> LENGTH: 486
<212> TYPE: PRT
<213> ORGANISM: Artificial Sequence
<220> FEATURE:
<223> OTHER INFORMATION: Humicola insolens protein disulfide isomerase
      (PDI), without signal peptide

<400> SEQUENCE: 40

Met Ser Asp Val Val Gln Leu Lys Lys Asp Thr Phe Asp Asp Phe Ile
1 5 10 15

Lys Thr Asn Asp Leu Val Leu Ala Glu Phe Phe Ala Pro Trp Cys Gly
20 25 30

His Cys Lys Ala Leu Ala Pro Glu Tyr Glu Glu Ala Ala Thr Thr Leu
35 40 45

Lys Glu Lys Asn Ile Lys Leu Ala Lys Val Asp Cys Thr Glu Glu Thr
50 55 60

Asp Leu Cys Gln Gln His Gly Val Glu Gly Tyr Pro Thr Leu Lys Val
65 70 75 80

Phe Arg Gly Leu Asp Asn Val Ser Pro Tyr Lys Gly Gln Arg Lys Ala
85 90 95

Ala Ala Ile Thr Ser Tyr Met Ile Lys Gln Ser Leu Pro Ala Val Ser
100 105 110

Glu Val Thr Lys Asp Asn Leu Glu Glu Phe Lys Lys Ala Asp Lys Ala
115 120 125

Val Leu Val Ala Tyr Val Asp Ala Ser Asp Lys Ala Ser Ser Glu Val
130 135 140

Phe Thr Gln Val Ala Glu Lys Leu Arg Asp Asn Tyr Pro Phe Gly Ser
145 150 155 160

Ser Ser Asp Ala Ala Leu Ala Glu Ala Glu Gly Val Lys Ala Pro Ala
165 170 175

Ile Val Leu Tyr Lys Asp Phe Asp Glu Gly Lys Ala Val Phe Ser Glu
180 185 190

Lys Phe Glu Val Glu Ala Ile Glu Lys Phe Ala Lys Thr Gly Ala Thr
195 200 205

Pro Leu Ile Gly Glu Ile Gly Pro Glu Thr Tyr Ser Asp Tyr Met Ser
210 215 220

Ala Gly Ile Pro Leu Ala Tyr Ile Phe Ala Glu Thr Ala Glu Glu Arg
225 230 235 240

Lys Glu Leu Ser Asp Lys Leu Lys Pro Ile Ala Glu Ala Gln Arg Gly
245 250 255

Val Ile Asn Phe Gly Thr Ile Asp Ala Lys Ala Phe Gly Ala His Ala
260 265 270

Gly Asn Leu Asn Leu Lys Thr Asp Lys Phe Pro Ala Phe Ala Ile Gln
275 280 285

Glu Val Ala Lys Asn Gln Lys Phe Pro Phe Asp Gln Glu Lys Glu Ile
290 295 300
```

```
Thr Phe Glu Ala Ile Lys Ala Phe Val Asp Asp Phe Val Ala Gly Lys
305                 310                 315                 320

Ile Glu Pro Ser Ile Lys Ser Glu Pro Ile Pro Glu Lys Gln Glu Gly
                325                 330                 335

Pro Val Thr Val Val Val Ala Lys Asn Tyr Asn Glu Ile Val Leu Asp
            340                 345                 350

Asp Thr Lys Asp Val Leu Ile Glu Phe Tyr Ala Pro Trp Cys Gly His
        355                 360                 365

Cys Lys Ala Leu Ala Pro Lys Tyr Glu Glu Leu Gly Ala Leu Tyr Ala
    370                 375                 380

Lys Ser Glu Phe Lys Asp Arg Val Val Ile Ala Lys Val Asp Ala Thr
385                 390                 395                 400

Ala Asn Asp Val Pro Asp Glu Ile Gln Gly Phe Pro Thr Ile Lys Leu
                405                 410                 415

Tyr Pro Ala Gly Ala Lys Gly Gln Pro Val Thr Tyr Ser Gly Ser Arg
            420                 425                 430

Thr Val Glu Asp Leu Ile Lys Phe Ile Ala Glu Asn Gly Lys Tyr Lys
        435                 440                 445

Ala Ala Ile Ser Glu Asp Ala Glu Glu Thr Ser Ser Ala Thr Glu Thr
    450                 455                 460

Thr Thr Glu Thr Ala Thr Lys Ser Glu Glu Ala Ala Lys Glu Thr Ala
465                 470                 475                 480

Thr Glu His Asp Glu Leu
                485
```

<210> SEQ ID NO 41
<211> LENGTH: 1487
<212> TYPE: DNA
<213> ORGANISM: Artificial Sequence
<220> FEATURE:
<223> OTHER INFORMATION: Polynucleotide encoding Humicola insolens PDI
without signal peptide

<400> SEQUENCE: 41

```
gctagcagga ggaattcacc atgtctgatg ttgtacaact gaagaaagat acgttcgatg     60

actttatcaa aactaatgac ttggtgctgg cagagttttt cgccccgtgg tgtggccact    120

gcaaagctct ggctccggag tacgaagagg ccgcgaccac cctgaaagaa aagaacatca    180

aactggcgaa agtggactgt acggaagaaa ccgacctgtg tcagcagcac ggcgtggaag    240

gttacccgac cctgaaggtg tttcgtggcc tggacaatgt tagcccgtac aaaggtcaac    300

gtaaggccgc agcgatcacc agctacatga tcaagcagtc gctgcctgca gtctctgagg    360

tgaccaaaga taatctggaa gagttcaaaa aggcagataa ggcggtgctg gttgcctatg    420

ttgatgcaag cgacaaggcg agcagcgagg tctttaccca ggtcgcggag aaattgcgcg    480

ataactaccc gttcggcagc agctccgatg cagctttggc cgaggcggaa ggtgtcaagg    540

ctccggcgat cgttctgtac aaagatttcg acgagggtaa agcggtgttc agcgaaaagt    600

ttgaggtgga agcaattgaa aagttcgcaa aaaccggtgc cacgcctttg attggcgaaa    660

tcggtccgga aacctattct gactatatga gcgccggtat cccgctggcc tacattttcg    720

cagaaacggc agaagagcgc aaagaactga gcgacaagtt gaagccaatt gcagaggcac    780

agcgtggcgt catcaacttt ggtaccattg acgcgaaagc atttggtgcg catgccggta    840

acctgaatct gaaaacggac aaatttccgg cgtttgcgat tcaagaggtg gcgaagaacc    900

aaaagtttcc gttcgatcaa gaaaaagaga ttaccttcga ggcgatcaaa gcgttcgttg    960
```

acgactttgt tgccggtaaa atcgagccga gcattaagag cgagccgatc ccggagaagc 1020
aggaaggccc ggtgaccgtc gtcgtcgcga agaattacaa cgagattgtt ctggatgaca 1080
cgaaagacgt cctgattgag ttctatgcgc cgtggtgcgg tcattgcaaa gcgctggccc 1140
cgaaatatga agagctgggt gcgctgtacg cgaagagcga gtttaaggac cgtgtggtta 1200
tcgcgaaagt agatgcgacc gccaatgacg ttcctgacga gatccaaggc ttcccgacca 1260
ttaaactgta tccggctggt gctaaaggcc agccagttac ctatagcggt agccgcacgg 1320
ttgaggatct gattaagttc attgccgaga acggcaagta caaggcggca atcagcgagg 1380
atgcagaaga aacgagctcc gcaaccgaaa ccacgacgga aaccgctact aagtccgaag 1440
aggcggcgaa agaaaccgcg acggagcacg atgagctgta agtcgac 1487

<210> SEQ ID NO 42
<211> LENGTH: 5304
<212> TYPE: DNA
<213> ORGANISM: Artificial Sequence
<220> FEATURE:
<223> OTHER INFORMATION: Dual-promoter vector, pSOL

<400> SEQUENCE: 42
ggcctttctt cggtagaagt cttcccccag aggcaggtat caaaggatct tcttgagatc 60
ctttttttct gcgcgtaatc tgctgcttgc aaacaaaaaa accaccgcta ccagcggtgg 120
tttgtttgcc ggatcaagag ctaccaactc tttttccgag gtaactggct tcagcagagc 180
gcagatacca aatactgttc ttctagtgta gccgtagtta ggccaccact tcaagaactc 240
tgtagcaccg cctacatacc tcgctctgct aatcctgtta ccagtggctg ctgccagtgg 300
cgataagtcg tgtcttaccg ggttggactc aagacgatag ttaccggata aggcgcagcg 360
gtcgggctga acggggggtt cgtgcacaca gcccagcttg gagcgaacga cctacaccga 420
actgagatac ctacagcgtg agctatgaga aagcgccacg cttcccgaag ggagaaaggc 480
ggacaggtat ccggtaagcg gcagggtcgg aacaggagag cgcacgaggg agcttccagg 540
gggaaacgcc tggtatcttt atagtcctgt cgggtttcgc cacctctgac ttgagcatcg 600
atttttgtga tgctcgtcag gggggcggag cctatggaaa aacgccagca acgcagaaag 660
gcccacccga aggtgagcca ggtgattaca tttgggccct catcagaggt tttcaccgtc 720
atcaccgaaa cgcgcgaggc agctgcggta aagctcatca gcgtggtcgt gaagcgattc 780
acagatgtct gcctgttcat ccgcgtccag ctcgttgagt ttctccagaa gcgttaatgt 840
ctggcttctg ataaagcggg ccatgttaag ggcggttttt tcctgtttgg tcatacctgc 900
ttagaaaaac tcatcgagca tcaaatgaaa ttgcaattta ttcatatcag gattatcaat 960
accatatttt tgaaaaagcc gtttctgtaa tgaaggagaa aactcaccga ggcagttcca 1020
taggatggca agatcctggt atcggtctgc gattccgact cgtccaacat caatacaacc 1080
tattaatttc ccctcgtcaa aaataaggtt atcaagtgag aaatcaccat gagtgacgac 1140
tgaatccggt gagaatggca aaagtttatg catttctttc cagacttgtt caacaggcca 1200
gccattacgc tcgtcatcaa aatcactcgc atcaaccaaa ccgttattca ttcgtgattg 1260
cgcctgagcg aggcgaaata cgcgatcgct gttaaaagga caattacaaa caggaatcga 1320
gtgcaaccgg cgcaggaaca ctgccagcgc atcaacaata ttttcacctg aatcaggata 1380
ttcttctaat acctggaacg ctgtttttcc ggggatcgca gtggtgagta accatgcatc 1440
atcaggagta cggataaaat gcttgatggt cggaagtggc ataaattccg tcagccagtt 1500
tagtctgacc atctcatctg taacatcatt ggcaacgcta cctttgccat gtttcagaaa 1560

-continued caactctggc gcatcgggct tcccatacaa gcgatagatt gtcgcacctg attgcccgac 1620
attatcgcga gcccatttat acccatataa atcagcatcc atgttggaat ttaatcgcgg 1680
cctcgacgtt tcccgttgaa tatggctcat agctcctgaa aatctcgata actcaaaaaa 1740
tacgcccggt agtgatctta tttcattatg gtgaaagttg gaacctctta cgtgccgatc 1800
aagaagacgg tcaaaagcct ccggtcggag gccgggagag tgttcaccga caaacaacag 1860
ataaaacaaa aggcccagtc ttccgactga gccttttgtt ttatttgatg tctggcagtt 1920
cccgagacgt tatgacaact tgacggctac atcattcact ttttcttcac aaccggcacg 1980
gaactcgctc gggctggccc cggtgcattt tttaaatacc cgcgagaaat agagttgatc 2040
gtcaaaacca acattgcgac cgacggtggc gataggcatc cgggtggtgc tcaaaagcag 2100
cttcgcctgg ctgatacgtt ggtcctcgcg ccagcttaag acgctaatcc ctaactgctg 2160
gcggaaaaga tgtgacagac gcgacggcga caagcaaaca tgctgtgcga cgctggcgat 2220
atcaaaattg ctgtctgcca ggtgatcgct gatgtactga caagcctcgc gtacccgatt 2280
atccatcggt ggatggagcg actcgttaat cgcttccatg cgccgcagta acaattgctc 2340
aagcagattt atcgccagca gctccgaata gcgcccttcc ccttgcccgg cgttaatgat 2400
ttgcccaaac aggtcgctga aatgcggctg gtgcgcttca tccgggcgaa agaaccccgt 2460
attggcaaat attgacggcc agttaagcca ttcatgccag taggcgcgcg gacgaaagta 2520
aacccactgg tgataccatt cgcgagcctc cggatgacga ccgtagtgat gaatctctcc 2580
tggcgggaac agcaaaatat cacccggtcg gcaaacaaat tctcgtccct gatttttcac 2640
cacccctga ccgcgaatgg tgagattgag aatataacct ttcattccca gcggtcggtc 2700
gataaaaaaa tcgagataac cgttggcctc aatcggcgtt aaacccgcca ccagatgggc 2760
attaaacgag tatcccggca gcaggggatc attttgcgct tcagccatac ttttcatact 2820
cccgccattc agagaagaaa ccaattgtcc atattgcatc agacattgcc gtctctgcgt 2880
cttttactgg ctcttctcgc taaccaaacc ggtaaccccg cttattaaaa gcattctgta 2940
acaaagcggg accaaagcca tgacaaaaac gcgtaacaaa agtgtctata atcacggcag 3000
aaaagtccac attgattatt tgcacggcgt cacactttgc tatgccatag catttttatc 3060
cataagatta gcggatccta cctgacgctt tttatcgcaa ctctctactg tttctccata 3120
cccgtttttt tgggctagca ggaggtaaaa aaaatgtgag accggtctcg gtctagatcg 3180
gtcagtttca cctgatttac gtaaaaaccc gcttcggcgg gtttttgctt ttggaggggc 3240
agaaagatga atgactgtct ctcctgttag tgagggttaa tgcccggaac gaagaaaggc 3300
ccacccgtga aggtgagcca gtgagttggt tacattttct cttgagggtt tagcttttca 3360
gacgacgcca aaaggtcgta cgtgaaatac ccaaatagtt ggccgcagcc gtcttgtcac 3420
cattaaactt ctcaagcgct tgctgcgggg tcagcaaacg cggagccggc gtctttgcgc 3480
tctcacgcgc cagctccggc agcagcaact gcatgaattg cggagtcaga tccggggtcg 3540
gctcaacgga caggaacagc gccaggcgtt ccatcatatt acgcagctcg cggatgttac 3600
ccggccagtc ataatgcagc agcaccgttt cgctcgcctg cagaccctgg cgcagtgccg 3660
cagagaacgg tgcgctcagg gctgccagcg agactttcag gaaagactcc gccagcggta 3720
aaatgtcggc gacacgttca cgcaacggcg ggagctgcag acgcagaatg ctcaggcggt 3780
agaacaggtc gcgacgaaaa cggccctgtt gcatatcctc ttccagattg cagtgggtcg 3840
cgctaatcac gcgcacgtct accggaaccg gttgatgacc accgacgcgg gtcacttctt 3900

-continued

```
tctcttccag cacacgcagc agacgggttt gcaatggcag cggcatctca ccgatctcgt   3960

ccaggaacaa ggtgccgccg tgggcaattt caaacaaacc agcacggcca ccgcgacggc   4020

tacccgtgaa tgcgccctct tcgtagccaa acagctcagc ttccagcagg ctttccgcga   4080

ttgcaccgca attaactgcc acaaacggat gagatttctt accctggcgg gcatcgtgac   4140

gggcgaaata ctcacgatgg attgcttgcg cagccagttc cttacccgta ccagtctcgc   4200

cttcgatcag aacagccgcg ctgctacgtg catacagcag aatggtctgg cgaacttgct   4260

ccatttgagg gctttggccc agcatatcac ccaggacata acgggtacgc agcgcattac   4320

gcgtcgcatc gtgggtgttg tggcgcaggc tcattctggt catgtccagg gcgtcgctga   4380

acgcctgacg caccgttgcc gcgctgtaga taaagatgcc cgtcatgccc gcttcttcgg   4440

ccaagtccgt gatcagaccc gcaccaacca cagcctcggt accgttcgct ttcagttcgt   4500

tgatctggcc acgtgcatct tcctcggtaa tgtagctgcg ttggtccagg cgcagattaa   4560

aggtcttttg aaacgcgacc agcgcaggga tcgtttcctg gtaggtgaca acgccaatcg   4620

aggaggtcag tttgcctgcc ttcgccagcg cctgcaagac atcgtaaccg ctcggcttaa   4680

tcaggatcac cggcacggac agacgggatt tcaggtaggc accattgcta cccgctgcga   4740

taatggcgtc acaacgctcg ttggccagct tttgcgaat gtaggtaacg gctttctcga   4800

aacccagctg aatcggagtg atgttcgcca ggtgatcaaa ctccaggcta atgtcgcgga   4860

acaactcgaa cagacgggtg acgctaacgg tccaaataac tggtttatca tcgttcaaac   4920

gcggtgggtg tgccatggtg aatacctcct gttaagaaac cgaatattgg gtttaaactt   4980

gtttcataat tgttgcaatg aaacgcggtg aaacattgcc tgaaacgtta actgaaacgc   5040

atatttgcgg attagttcat gactttatct ctaacaaatt gaaattaaac atttaatttt   5100

attaaggcaa ttgtggcaca ccccttgctt tgtctttatc aacgcaaata acaagttgat   5160

aacaaaagct taggaggaaa acatagagac cggtctctct cgagtaacta gttgatagag   5220

atcaagcctt aacgaactaa gaccccccgca ccgaaaggtc cggggggtttt ttttgacctt   5280

aaaaacataa ccgaggagca gaca                                          5304
```

```
<210> SEQ ID NO 43
<211> LENGTH: 104
<212> TYPE: PRT
<213> ORGANISM: Artificial Sequence
<220> FEATURE:
<223> OTHER INFORMATION: CPBpro variant lispro proinsulin polypeptide
      PN2.5

<400> SEQUENCE: 43

Met His His His His His His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Glu Val Arg Phe Val Asn Gln
        35                  40                  45

His Leu Cys Gly Ser His Leu Val Glu Ala Leu Tyr Leu Val Cys Gly
    50                  55                  60

Glu Arg Gly Phe Phe Tyr Thr Lys Pro Thr Arg Arg Tyr Pro Gly Asp
65                  70                  75                  80

Val Lys Arg Gly Ile Val Glu Gln Cys Cys Thr Ser Ile Cys Ser Leu
                85                  90                  95

Tyr Gln Leu Glu Asn Tyr Cys Asn
            100
```

<210> SEQ ID NO 44
<211> LENGTH: 329
<212> TYPE: DNA
<213> ORGANISM: Artificial Sequence
<220> FEATURE:
<223> OTHER INFORMATION: Polynucleotide encoding CPBpro variant lispro proinsulin polypeptide PN2.5

<400> SEQUENCE: 44

```
aggaggtaaa aaaaatgcac caccatcacc atcacgaagt ctttgttgag aatgacatta     60

gcctgcacga actggcatct acccaaatcg atttctggcc ggacatcgaa gttgactttc    120

gtgtgaaagc cgaagatgag gtccgcttcg ttaatcaaca cctgtgtggt tcccatctgg    180

tcgaagcgct gtatttggtt tgcggtgagc gcggtttctt ttacacgaaa ccgacccgtc    240

gctatccggg cgacgtgaag cgtggtatcg tggaacagtg ttgcaccagc atttgcagcc    300

tgtaccagct ggagaactat tgtaactaa                                      329
```

<210> SEQ ID NO 45
<211> LENGTH: 111
<212> TYPE: PRT
<213> ORGANISM: Artificial Sequence
<220> FEATURE:
<223> OTHER INFORMATION: CPBpro variant lispro proinsulin polypeptide PN2.6

<400> SEQUENCE: 45

```
Met His His Ser Gly Glu His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Val Glu Asp Phe Glu Leu Asp
        35                  40                  45

Arg Val Arg Phe Val Asn Gln His Leu Cys Gly Ser His Leu Val Glu
    50                  55                  60

Ala Leu Tyr Leu Val Cys Gly Glu Arg Gly Phe Phe Tyr Thr Lys Pro
65                  70                  75                  80

Thr Arg Arg Tyr Pro Gly Asp Val Lys Arg Gly Ile Val Glu Gln Cys
                85                  90                  95

Cys Thr Ser Ile Cys Ser Leu Tyr Gln Leu Glu Asn Tyr Cys Asn
            100                 105                 110
```

<210> SEQ ID NO 46
<211> LENGTH: 350
<212> TYPE: DNA
<213> ORGANISM: Artificial Sequence
<220> FEATURE:
<223> OTHER INFORMATION: Polynucleotide encoding CPBpro variant lispro proinsulin polypeptide PN2.6

<400> SEQUENCE: 46

```
aggaggtaaa aaaaatgcac cactctggcg aacatgaagt tttgttgag aatgatatta     60

gcctgcacga actggcaagc acccaaatcg atttctggcc ggacatcgaa gttgactttc    120

gtgtgaaagc cgaagatgtg gaagatttcg agctggaccg tgtccgcttc gttaatcaac    180

acctgtgtgg ttcccatctg gtcgaagcgc tgtatttggt ttgcggtgag cgcggtttct    240

tttacacgaa accgacccgt cgctatccgg gcgacgtgaa gcgtggtatc gtggaacagt    300

gttgcaccag catttgcagc ctgtaccagc tggagaacta ttgtaactaa               350
```

<210> SEQ ID NO 47
<211> LENGTH: 111
<212> TYPE: PRT
<213> ORGANISM: Artificial Sequence
<220> FEATURE:
<223> OTHER INFORMATION: CPBpro variant lispro proinsulin polypeptide
PN2.7

<400> SEQUENCE: 47

```
Met His His His His His His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Val Glu Asp Phe Glu Leu Asp
        35                  40                  45

Arg Val Arg Phe Val Asn Gln His Leu Cys Gly Ser His Leu Val Glu
    50                  55                  60

Ala Leu Tyr Leu Val Cys Gly Glu Arg Gly Phe Phe Tyr Thr Lys Pro
65                  70                  75                  80

Thr Arg Arg Tyr Pro Gly Asp Val Lys Arg Gly Ile Val Glu Gln Cys
                85                  90                  95

Cys Thr Ser Ile Cys Ser Leu Tyr Gln Leu Glu Asn Tyr Cys Asn
            100                 105                 110
```

<210> SEQ ID NO 48
<211> LENGTH: 350
<212> TYPE: DNA
<213> ORGANISM: Artificial Sequence
<220> FEATURE:
<223> OTHER INFORMATION: Polynucleotide encoding CPBpro variant lispro
proinsulin polypeptide PN2.7

<400> SEQUENCE: 48

```
aggaggtaaa aaaaatgcac caccatcacc atcacgaagt ctttgttgag aatgacatta     60

gcctgcacga actggcatct acccaaatcg atttctggcc ggacatcgaa gttgactttc    120

gtgtgaaagc cgaagatgtg gaagatttcg agctggaccg tgtccgcttc gttaatcaac    180

acctgtgtgg ttcccatctg gtcgaagcgc tgtatttggt ttgcggtgag cgcggtttct    240

tttacacgaa accgacccgt cgctatccgg gcgacgtgaa gcgtggtatc gtggaacagt    300

gttgcaccag catttgcagc ctgtaccagc tggagaacta ttgtaactaa               350
```

<210> SEQ ID NO 49
<211> LENGTH: 113
<212> TYPE: PRT
<213> ORGANISM: Artificial Sequence
<220> FEATURE:
<223> OTHER INFORMATION: CPBpro variant lispro proinsulin polypeptide
PN2.8

<400> SEQUENCE: 49

```
Met His His Ser Gly Glu His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Val Glu Asp Phe Glu Leu Gln
        35                  40                  45

Asp Ser Arg Val Arg Phe Val Asn Gln His Leu Cys Gly Ser His Leu
    50                  55                  60

Val Glu Ala Leu Tyr Leu Val Cys Gly Glu Arg Gly Phe Phe Tyr Thr
```

-continued

```
65                  70                  75                  80

Lys Pro Thr Arg Arg Tyr Pro Gly Asp Val Lys Arg Gly Ile Val Glu
                85                  90                  95

Gln Cys Cys Thr Ser Ile Cys Ser Leu Tyr Gln Leu Glu Asn Tyr Cys
            100                 105                 110

Asn


<210> SEQ ID NO 50
<211> LENGTH: 356
<212> TYPE: DNA
<213> ORGANISM: Artificial Sequence
<220> FEATURE:
<223> OTHER INFORMATION: Polynucleotide encoding CPBpro variant lispro
      proinsulin polypeptide PN2.8

<400> SEQUENCE: 50

aggaggtaaa aaaaatgcac cactctggcg aacatgaagt ttttgttgag aatgatatta     60

gcctgcacga actggcaagc acccaaatcg atttctggcc ggacatcgaa gttgactttc    120

gtgtgaaagc cgaagatgtg gaagatttcg agctgcagga cagccgtgtc cgcttcgtta    180

atcaacacct gtgtggttcc catctggtcg aagcgctgta tttggtttgc ggtgagcgcg    240

gtttctttta cacgaaaccg acccgtcgct atccgggcga cgtgaagcgt ggtatcgtgg    300

aacagtgttg caccagcatt tgcagcctgt accagctgga gaactattgt aactaa        356


<210> SEQ ID NO 51
<211> LENGTH: 113
<212> TYPE: PRT
<213> ORGANISM: Artificial Sequence
<220> FEATURE:
<223> OTHER INFORMATION: CPBpro variant lispro proinsulin polypeptide
      PN2.9

<400> SEQUENCE: 51

Met His His His His His His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Val Glu Asp Phe Glu Leu Gln
        35                  40                  45

Asp Ser Arg Val Arg Phe Val Asn Gln His Leu Cys Gly Ser His Leu
    50                  55                  60

Val Glu Ala Leu Tyr Leu Val Cys Gly Glu Arg Gly Phe Phe Tyr Thr
65                  70                  75                  80

Lys Pro Thr Arg Arg Tyr Pro Gly Asp Val Lys Arg Gly Ile Val Glu
                85                  90                  95

Gln Cys Cys Thr Ser Ile Cys Ser Leu Tyr Gln Leu Glu Asn Tyr Cys
            100                 105                 110

Asn


<210> SEQ ID NO 52
<211> LENGTH: 356
<212> TYPE: DNA
<213> ORGANISM: Artificial Sequence
<220> FEATURE:
<223> OTHER INFORMATION: Polynucleotide encoding CPBpro variant lispro
      proinsulin polypeptide PN2.9

<400> SEQUENCE: 52

aggaggtaaa aaaaatgcac caccatcacc atcacgaagt ctttgttgag aatgacatta     60
```

```
gcctgcacga actggcatct acccaaatcg atttctggcc ggacatcgaa gttgactttc    120

gtgtgaaagc cgaagatgtg gaagatttcg agctgcagga cagccgtgtc cgcttcgtta    180

atcaacacct gtgtggttcc catctggtcg aagcgctgta tttggtttgc ggtgagcgcg    240

gtttctttta cacgaaaccg acccgtcgct atccgggcga cgtgaagcgt ggtatcgtgg    300

aacagtgttg caccagcatt tgcagcctgt accagctgga gaactattgt aactaa        356
```

```
<210> SEQ ID NO 53
<211> LENGTH: 118
<212> TYPE: PRT
<213> ORGANISM: Artificial Sequence
<220> FEATURE:
<223> OTHER INFORMATION: CPBpro variant lispro proinsulin polypeptide
      PN2.10

<400> SEQUENCE: 53

Met His His Ser Gly Glu His Glu Lys Val Phe Arg Val Glu Asn Asp
1               5                   10                  15

Ile Ser Leu His Glu Leu Ala Ser Thr Gln Ile Asp Phe Trp Lys Pro
            20                  25                  30

Asp Ile His Val Asp Phe Arg Val Lys Ala Glu Asp Leu Val Glu Asp
        35                  40                  45

Phe Leu Glu Gln Glu Leu Gln Arg Val Arg Phe Val Asn Gln His Leu
    50                  55                  60

Cys Gly Ser His Leu Val Glu Ala Leu Tyr Leu Val Cys Gly Glu Arg
65                  70                  75                  80

Gly Phe Phe Tyr Thr Lys Pro Thr Arg Arg Tyr Pro Gly Asp Val Lys
                85                  90                  95

Arg Gly Ile Val Glu Gln Cys Cys Thr Ser Ile Cys Ser Leu Tyr Gln
            100                 105                 110

Leu Glu Asn Tyr Cys Asn
        115
```

```
<210> SEQ ID NO 54
<211> LENGTH: 371
<212> TYPE: DNA
<213> ORGANISM: Artificial Sequence
<220> FEATURE:
<223> OTHER INFORMATION: Polynucleotide encoding CPBpro variant lispro
      proinsulin polypeptide PN2.10

<400> SEQUENCE: 54

aggaggtaaa aaaaatgcac cactctggcg aacatgaaaa ggtttttcgc gttgagaatg     60

atattagcct gcacgaactg gcaagcaccc aaatcgattt ctggaaaccg gacatccatg    120

tggactttcg tgtgaaagcc gaagatttgg tcgaagattt cctggagcaa gagctgcagc    180

gtgtccgctt cgttaatcaa cacctgtgtg gttcccatct ggtcgaagcg ctgtatttgg    240

tttgcggtga gcgcggtttc ttttacacga aaccgacccg tcgctatccg ggcgacgtga    300

agcgtggtat cgtggaacag tgttgcacca gcatttgcag cctgtaccag ctggagaact    360

attgtaacta a                                                         371
```

```
<210> SEQ ID NO 55
<211> LENGTH: 104
<212> TYPE: PRT
<213> ORGANISM: Artificial Sequence
<220> FEATURE:
<223> OTHER INFORMATION: CPBpro variant glargine proinsulin polypeptide
      PN3.13
```

<400> SEQUENCE: 55

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Glu Val Arg Phe Val Asn Gln
35 40 45

His Leu Cys Gly Ser His Leu Val Glu Ala Leu Tyr Leu Val Cys Gly
50 55 60

Glu Arg Gly Phe Phe Tyr Thr Pro Lys Thr Arg Arg Tyr Pro Gly Asp
65 70 75 80

Val Lys Arg Gly Ile Val Glu Gln Cys Cys Thr Ser Ile Cys Ser Leu
85 90 95

Tyr Gln Leu Glu Asn Tyr Cys Gly
100

<210> SEQ ID NO 56
<211> LENGTH: 329
<212> TYPE: DNA
<213> ORGANISM: Artificial Sequence
<220> FEATURE:
<223> OTHER INFORMATION: Polynucleotide encoding CPBpro variant glargine proinsulin polypeptide PN3.13

<400> SEQUENCE: 56
aggaggtaaa aaaaatgcac caccatcacc atcacgaagt ctttgttgag aatgacatta 60
gcctgcacga actggcatct acccaaatcg atttctggcc ggacatcgaa gttgactttc 120
gtgtgaaagc cgaagatgag gtccgcttcg ttaatcaaca cctgtgtggt tcccatctgg 180
tcgaagcgct gtatttggtt tgcggtgagc gcggtttctt ttacacgccg aaaactcgcc 240
gttatccggg tgacgtgaag cgtggtatcg tggaacagtg ttgcaccagc atttgcagcc 300
tgtaccagct ggagaactat tgtggctaa 329

<210> SEQ ID NO 57
<211> LENGTH: 570
<212> TYPE: DNA
<213> ORGANISM: Artificial Sequence
<220> FEATURE:
<223> OTHER INFORMATION: Polynucleotide encoding Saccharomyces cerevisiae (strain S288c) Erv1p

<400> SEQUENCE: 57
atgaaagcga ttgataagat gaccgataat ccaccgcaag aaggtctgag cggccgtaaa 60
atcatctacg acgaagatgg caaaccgtgt cgtagctgca acaccctgct ggactttcaa 120
tatgtgacgg gtaagatttc caatggcctg aaaaacctga gcagcaatgg caagctggcc 180
ggtacgggtg ctttgaccgg tgaggcgtct gaactgatgc ctggtagccg tacgtaccgc 240
aaggttgatc cgccggacgt tgagcagctg ggtcgctcca gctggacttt gctgcatagc 300
gtcgcggcga gctacccggc acagccgacc gaccagcaaa agggtgagat gaaacagttt 360
ctgaacattt tctcgcacat ctatccgtgc aattggtgtg ccaaagactt tgaaaagtat 420
atccgtgaga atgcgccgca agtggagagc cgcgaagaac tgggccgttg gatgtgtgag 480
gcacacaaca aagtcaacaa aaagctgcgt aaaccgaagt tcgattgcaa cttctgggag 540
aagcgctgga aagacggctg ggatgagtaa 570

<210> SEQ ID NO 58
<211> LENGTH: 13
<212> TYPE: PRT
<213> ORGANISM: Homo sapiens

<400> SEQUENCE: 58

Gln Cys Cys Thr Ser Ile Cys Ser Leu Tyr Gln Leu Glu
1 5 10

<210> SEQ ID NO 59
<211> LENGTH: 12
<212> TYPE: PRT
<213> ORGANISM: Homo sapiens

<400> SEQUENCE: 59

Phe Val Asn Gln His Leu Gly Ser His Leu Val Glu
1 5 10

<210> SEQ ID NO 60
<211> LENGTH: 4
<212> TYPE: PRT
<213> ORGANISM: Homo sapiens

<400> SEQUENCE: 60

Asn Tyr Cys Gly
1

<210> SEQ ID NO 61
<211> LENGTH: 8
<212> TYPE: PRT
<213> ORGANISM: Homo sapiens

<400> SEQUENCE: 61

Ala Leu Tyr Leu Val Cys Gly Glu
1 5

<210> SEQ ID NO 62
<211> LENGTH: 108
<212> TYPE: PRT
<213> ORGANISM: Artificial Sequence
<220> FEATURE:
<223> OTHER INFORMATION: CPBpro variant glargine proinsulin polypeptide
PN3.15

<400> SEQUENCE: 62

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Glu Val Asp Pro Asp Pro Arg
35 40 45

Phe Val Asn Gln His Leu Cys Gly Ser His Leu Val Glu Ala Leu Tyr
50 55 60

Leu Val Cys Gly Glu Arg Gly Phe Phe Tyr Thr Pro Lys Thr Arg Arg
65 70 75 80

Tyr Pro Gly Asp Val Lys Arg Gly Ile Val Glu Gln Cys Cys Thr Ser
85 90 95

Ile Cys Ser Leu Tyr Gln Leu Glu Asn Tyr Cys Gly
100 105

<210> SEQ ID NO 63
<211> LENGTH: 359
<212> TYPE: DNA

<213> ORGANISM: Artificial Sequence
<220> FEATURE:
<223> OTHER INFORMATION: Polynucleotide encoding CPBpro variant glargine proinsulin polypeptide PN3.15

<400> SEQUENCE: 63

```
aggaggtaaa aaaaatgcac caccatcacc atcacgaagt ctttgttgag aatgacatta     60

gcctgcacga actggcatct acccaaatcg atttctggcc ggacatcgaa gttgactttc    120

gtgtgaaagc cgaagatgag gtcgatcctg atccgcgctt cgttaatcaa cacctgtgtg    180

gttcccatct ggtcgaagcg ctgtatttgg tttgcggtga gcgcggtttc ttttacacgc    240

cgaaaactcg ccgttatccg ggtgacgtga agcgtggtat cgtggaacag tgttgcacca    300

gcatttgcag cctgtaccag ctggagaact attgtggcta agtctagata actagttga     359
```

<210> SEQ ID NO 64
<211> LENGTH: 108
<212> TYPE: PRT
<213> ORGANISM: Artificial Sequence
<220> FEATURE:
<223> OTHER INFORMATION: CPBpro variant glargine proinsulin polypeptide PN3.16

<400> SEQUENCE: 64

```
Met His His His His His His Glu Val Phe Val Glu Asn Asp Ile Ser
1               5                   10                  15

Leu His Glu Leu Ala Ser Thr Gln Ile Asp Phe Trp Pro Asp Ile Glu
            20                  25                  30

Val Asp Phe Arg Val Lys Ala Glu Asp Glu Val Gly Asp Pro Gly Arg
        35                  40                  45

Phe Val Asn Gln His Leu Cys Gly Ser His Leu Val Glu Ala Leu Tyr
    50                  55                  60

Leu Val Cys Gly Glu Arg Gly Phe Phe Tyr Thr Pro Lys Thr Arg Arg
65                  70                  75                  80

Tyr Pro Gly Asp Val Lys Arg Gly Ile Val Glu Gln Cys Cys Thr Ser
                85                  90                  95

Ile Cys Ser Leu Tyr Gln Leu Glu Asn Tyr Cys Gly
            100                 105
```

<210> SEQ ID NO 65
<211> LENGTH: 359
<212> TYPE: DNA
<213> ORGANISM: Artificial Sequence
<220> FEATURE:
<223> OTHER INFORMATION: Polynucleotide encoding CPBpro variant glargine proinsulin polypeptide PN3.16

<400> SEQUENCE: 65

```
aggaggtaaa aaaaatgcac caccatcacc atcacgaagt ctttgttgag aatgacatta     60

gcctgcacga actggcatct acccaaatcg atttctggcc ggacatcgaa gttgactttc    120

gtgtgaaagc cgaagatgag gtcggagatc ctgggcgctt cgttaatcaa cacctgtgtg    180

gttcccatct ggtcgaagcg ctgtatttgg tttgcggtga gcgcggtttc ttttacacgc    240

cgaaaactcg ccgttatccg ggtgacgtga agcgtggtat cgtggaacag tgttgcacca    300

gcatttgcag cctgtaccag ctggagaact attgtggcta agtctagata actagttga     359
```

<210> SEQ ID NO 66
<211> LENGTH: 111
<212> TYPE: PRT
<213> ORGANISM: Artificial Sequence
<220> FEATURE:
<223> OTHER INFORMATION: CPBpro variant glargine proinsulin polypeptide PN3.17

<400> SEQUENCE: 66

Met His His His His His His Glu Val Phe Val Glu Asn Asp Ile Ser
1 5 10 15

Leu His Glu Leu Ala Ser Thr Gln Ile Asp Phe Trp Pro Asp Ile Glu
20 25 30

Val Asp Phe Arg Val Lys Ala Glu Asp Glu Val Gly Gly Asp Pro Gly
35 40 45

Gly Gly Arg Phe Val Asn Gln His Leu Cys Gly Ser His Leu Val Glu
50 55 60

Ala Leu Tyr Leu Val Cys Gly Glu Arg Gly Phe Phe Tyr Thr Pro Lys
65 70 75 80

Thr Arg Arg Tyr Pro Gly Asp Val Lys Arg Gly Ile Val Glu Gln Cys
85 90 95

Cys Thr Ser Ile Cys Ser Leu Tyr Gln Leu Glu Asn Tyr Cys Gly
100 105 110

<210> SEQ ID NO 67
<211> LENGTH: 368
<212> TYPE: DNA
<213> ORGANISM: Artificial Sequence
<220> FEATURE:
<223> OTHER INFORMATION: Polynucleotide encoding CPBpro variant glargine proinsulin polypeptide PN3.17

<400> SEQUENCE: 67
aggaggtaaa aaaaatgcac caccatcacc atcacgaagt ctttgttgag aatgacatta 60
gcctgcacga actggcatct acccaaatcg atttctggcc ggacatcgaa gttgactttc 120
gtgtgaaagc cgaagatgag gtcggaggcg atcctggcgg agggcgcttc gttaatcaac 180
acctgtgtgg ttcccatctg gtcgaagcgc tgtatttggt ttgcggtgag cgcggtttct 240
tttacacgcc gaaaactcgc cgttatccgg gtgacgtgaa gcgtggtatc gtggaacagt 300
gttgcaccag catttgcagc ctgtaccagc tggagaacta ttgtggctaa gtctagataa 360
ctagttga 368

<210> SEQ ID NO 68
<211> LENGTH: 103
<212> TYPE: PRT
<213> ORGANISM: Artificial Sequence
<220> FEATURE:
<223> OTHER INFORMATION: Variant glargine proinsulin polypeptide PN3.62

<400> SEQUENCE: 68

Met His His His His His His Glu Val Phe Val Glu Asn Asp Ile Ser
1 5 10 15

Leu Arg Phe Val Asn Gln His Leu Cys Gly Ser His Leu Val Glu Ala
20 25 30

Leu Tyr Leu Val Cys Gly Glu Arg Gly Phe Phe Tyr Thr Pro Lys Thr
35 40 45

Arg Arg Glu Ala Glu Asp Leu Gln Val Gly Gln Val Glu Leu Gly Gly
50 55 60

Gly Pro Gly Ala Gly Ser Leu Gln Pro Leu Ala Leu Glu Gly Ser Leu
65 70 75 80

Gln Arg Gly Ile Val Glu Gln Cys Cys Thr Ser Ile Cys Ser Leu Tyr
85 90 95

```
Gln Leu Glu Asn Tyr Cys Gly
            100


<210> SEQ ID NO 69
<211> LENGTH: 77
<212> TYPE: PRT
<213> ORGANISM: Artificial Sequence
<220> FEATURE:
<223> OTHER INFORMATION: Variant glargine proinsulin polypeptide PN3.116

<400> SEQUENCE: 69

Met His His His His His His Glu Val Phe Val Glu Asn Asp Ile Ser
1               5                   10                  15

Leu Arg Phe Val Asn Gln His Leu Cys Gly Ser His Leu Val Glu Ala
            20                  25                  30

Leu Tyr Leu Val Cys Gly Glu Arg Gly Phe Phe Tyr Thr Pro Lys Thr
        35                  40                  45

Arg Arg Asp Asp Asn Leu Glu Arg Gly Ile Val Glu Gln Cys Cys Thr
    50                  55                  60

Ser Ile Cys Ser Leu Tyr Gln Leu Glu Asn Tyr Cys Gly
65                  70                  75


<210> SEQ ID NO 70
<211> LENGTH: 93
<212> TYPE: PRT
<213> ORGANISM: Artificial Sequence
<220> FEATURE:
<223> OTHER INFORMATION: Variant glargine proinsulin polypeptide PN3.165

<400> SEQUENCE: 70

Met His His His His His His Arg Phe Val Asn Gln His Leu Cys Gly
1               5                   10                  15

Ser His Leu Val Glu Ala Leu Tyr Leu Val Cys Gly Glu Arg Gly Phe
            20                  25                  30

Phe Tyr Thr Pro Lys Thr Arg Arg Glu Ala Glu Asp Leu Gln Val Gly
        35                  40                  45

Gln Val Glu Leu Gly Gly Gly Pro Gly Ala Gly Ser Leu Gln Pro Leu
    50                  55                  60

Ala Leu Glu Gly Ser Leu Gln Arg Gly Ile Val Glu Gln Cys Cys Thr
65                  70                  75                  80

Ser Ile Cys Ser Leu Tyr Gln Leu Glu Asn Tyr Cys Gly
                85                  90


<210> SEQ ID NO 71
<211> LENGTH: 94
<212> TYPE: PRT
<213> ORGANISM: Artificial Sequence
<220> FEATURE:
<223> OTHER INFORMATION: Variant glargine proinsulin polypeptide PN3.172

<400> SEQUENCE: 71

Met His His His His His His Glu Val Phe Val Glu Asn Asp Ile Ser
1               5                   10                  15

Leu Arg Phe Val Asn Gln His Leu Cys Gly Ser His Leu Val Glu Ala
            20                  25                  30

Leu Tyr Leu Val Cys Gly Glu Arg Gly Phe Phe Tyr Thr Pro Lys Thr
        35                  40                  45

Arg Arg Glu Ala Glu Asp Leu Gln Val Gly Gln Val Glu Leu Gly Gly
    50                  55                  60
```

-continued

```
Gly Pro Gly Ala Gly Ser Leu Gln Arg Gly Ile Val Glu Gln Cys Cys
65                  70                  75                  80

Thr Ser Ile Cys Ser Leu Tyr Gln Leu Glu Asn Tyr Cys Gly
                85                  90


<210> SEQ ID NO 72
<211> LENGTH: 84
<212> TYPE: PRT
<213> ORGANISM: Artificial Sequence
<220> FEATURE:
<223> OTHER INFORMATION: Variant glargine proinsulin polypeptide PN3.185

<400> SEQUENCE: 72

Met His His His His His His Arg Phe Val Asn Gln His Leu Cys Gly
1               5                   10                  15

Ser His Leu Val Glu Ala Leu Tyr Leu Val Cys Gly Glu Arg Gly Phe
            20                  25                  30

Phe Tyr Thr Pro Lys Thr Arg Arg Glu Ala Glu Asp Leu Gln Val Gly
        35                  40                  45

Gln Val Glu Leu Gly Gly Gly Pro Gly Ala Gly Ser Leu Gln Arg Gly
    50                  55                  60

Ile Val Glu Gln Cys Cys Thr Ser Ile Cys Ser Leu Tyr Gln Leu Glu
65                  70                  75                  80

Asn Tyr Cys Gly


<210> SEQ ID NO 73
<211> LENGTH: 23
<212> TYPE: PRT
<213> ORGANISM: Artificial Sequence
<220> FEATURE:
<223> OTHER INFORMATION: Artificial variant of the human C-peptide:
      amino acids 3-25 of SEQ ID NO:13

<400> SEQUENCE: 73

Glu Ala Glu Asp Leu Gln Val Gly Gln Val Glu Leu Gly Gly Gly Pro
1               5                   10                  15

Gly Ala Gly Ser Leu Gln Arg
            20


<210> SEQ ID NO 74
<211> LENGTH: 6
<212> TYPE: PRT
<213> ORGANISM: Artificial Sequence
<220> FEATURE:
<223> OTHER INFORMATION: Artificial C-peptide: amino acids 3-8 of SEQ ID
      NO:14

<400> SEQUENCE: 74

Asp Asp Asn Leu Glu Arg
1               5
```

C-PEPTIDES AND PROINSULIN POLYPEPTIDES COMPRISING THE SAME

REFERENCE TO RELATED APPLICATIONS

This application is a continuation of International Application No. PCT/US2019/052998, filed 25 Sep. 2019, which claims the benefit of priority of U.S. Provisional Application No. 62/735,861, filed on 25 Sep. 2018, the entire disclosures of which are incorporated by reference herein.

REFERENCE TO THE SEQUENCE LISTING

This application includes a sequence listing submitted electronically, in a file entitled "AbSci-005PCTCON1_ST25.txt", created on 30 Apr. 2020 and having a size of 63 kilobytes (KB), which is incorporated by reference herein.

FIELD OF THE INVENTION

The present invention is in the general technical fields of molecular biology and biotechnological manufacturing. More particularly, the present invention is in the technical field of recombinant protein production.

BACKGROUND OF THE INVENTION

Efficient expression of recombinant proteins or other gene products requires the use of a system, the various aspects of which—expression construct(s), host cell strain, growth conditions, and purification methods—all work together to make the desired product in sufficient quantities, while minimizing the expenditure of materials and time.

Many expression systems that are currently used for industrial production of recombinant products rely on expensive mammalian cell culture, or utilize the secretion of proteins into the periplasm of bacterial cells, which is more limited in the quantity of product per cell and is more time-consuming than expression of gene products in bacterial cytoplasm. In many expression systems developed by others, in which bacterial cytoplasm is used as the preferred cellular compartment for recombinant expression, it is common for the desired proteins to be produced as insoluble inclusion bodies (see for example Chung et al., "Recombinant production of biologically active giant grouper (*Epinephelus lanceolatus*) growth hormone from inclusion bodies of *Escherichia coli* by fed-batch culture", Protein Expr Purif 2015 June; 110: 79-88; doi: 10.1016/j.pep.2015.02.012; Epub 2015 Feb. 19). To recover some soluble and correctly folded protein from inclusion bodies, it has been necessary to perform additional refolding steps (Yamaguchi and Miyazaki, "Refolding techniques for recovering biologically active recombinant proteins from inclusion bodies", Biomolecules 2014 Feb. 20; 4(1): 235-251; doi: 10.3390/biom4010235; Review). For proteins containing disulfide bonds, these refolding steps typically include the use of reducing agents to convert to thiol groups any inappropriately formed disulfide bonds, particularly intermolecular disulfide bonds that could be contributing to the aggregation of protein into insoluble inclusion bodies.

Improved expression systems and methods of using them to more efficiently produce gene products such as recombinant proteins in a properly folded and soluble form, and in a manner that is capable of scaling up to commercial production levels, are clearly needed.

SUMMARY OF THE INVENTION

The present invention provides methods of purifying proteins and other gene products, expressed in the form of solubilizable complexes that yield properly folded and active gene product when solubilized, without requiring the use of a reducing agent. An advantage of the invention is the ability to collect the solubilizable complexes of gene product in the form of a solubilizable pellet, allowing undesirable components of host cell lysate to be discarded in the supernatant. When the solubilizable complexes of gene product are present in a host cell lysate, for example, this mixture can be considered a suspension in that the solubilizable complexes can be sedimented into a pellet by centrifugation or other means, and separated from a predominantly liquid fraction of the host cell lysate. As used herein, the term "solution" encompasses mixtures that can exhibit the properties of a suspension. Further aspects of the invention relate to polypeptide prosequences that can be used in the expression and purification of proteins.

An aspect of the invention is a method for producing one or more gene products comprising: providing a first solution comprising at least one gene product that was expressed in a host cell, wherein at least some of said at least one gene product in the first solution can be sedimented by centrifugation (in salt conditions of 200 mM NaCl at pH 7.4 and 4 degrees C.) at a force of: 900×g, or at between 900×g and 7,000×g, or at 7,000×g, to form a solubilizable pellet; and placing at least some of said at least one gene product in a solubilization solution. The above method of the invention can be utilized according to any aspect of the method of the invention as expressed in the following paragraphs, in any combination thereof:

- The method of the invention wherein said at least one gene product is a polypeptide that forms at least one disulfide bond.
- The method of the invention wherein said at least one gene product is a polypeptide that lacks a signal peptide.
- The method of the invention wherein said at least one gene product comprises a polypeptide selected from the group consisting of (a) leptin, metreleptin, growth hormone, human growth hormone, a polypeptide comprising the amino acid sequence of a mature chain of insulin, and (b) a fragment of any of the polypeptides of (a).
- The method of the invention wherein said at least one gene product comprises a polypeptide comprising the amino acid sequence of a mature insulin chain and an amino acid sequence selected from the group consisting of: (a) any of SEQ ID NOs 12-14 and 37; and (b) an amino acid sequence that shares at least 70% (or at least 80%, or at least 90%) amino acid sequence identity across at least 50% (or at least 60%, or at least 70%, or at least 80%, or at least 90%) of the length of any of the amino acid sequences of (a).
- The method of the invention wherein said at least one gene product comprises a polypeptide comprising an amino acid sequence selected from the group consisting of: (a) any of SEQ ID NOs 27-36; and (b) an amino acid sequence that shares at least 70% (or at least 80%, or at least 90%) amino acid sequence identity across at least 50% (or at least 60%, or at least 70%, or at least 80%, or at least 90%) of the length of any of the amino acid sequences of (a).
- The method of the invention wherein at least one gene product comprises a polypeptide comprising an Asp- Pro amino acid sequence; and this method of the invention further comprising cleavage of said propeptide at the Asp-Pro amino acid sequence.

The method of the invention wherein the first solution is a lysate of said host cell; and this method of the invention wherein the lysate of said host cell was produced by contacting the host cell with lysozyme, or wherein the lysate of said host cell was produced by mechanical lysis.

The method of the invention wherein the host cell is a prokaryotic cell; and this method of the invention wherein the host cell is an *Escherichia coli* cell.

The method of the invention wherein the host cell has been modified to have a more oxidizing cytoplasm; and this method of the invention wherein the modification to said host cell results in defective expression of at least one gene selected from the group consisting of trxB, gor, gshA, and gshB; and this method of the invention wherein said host cell further comprises a mutation in the ahpC gene.

The method of the invention wherein the host cell comprises one or more expression constructs; and this method of the invention wherein said at least one expression construct comprises at least one inducible promoter; and this method of the invention wherein said at least one inducible promoter is selected from the group consisting of an arabinose-inducible promoter, a propionate-inducible promoter, a rhamnose-inducible promoter, a xylose-inducible promoter, a lactose-inducible promoter, and a promoter inducible by phosphate depletion, and/or wherein said host cell has a reduced level of gene function of at least one gene encoding a protein that metabolizes the inducer of at least one of said at least one inducible promoter; and this method of the invention wherein the at least one gene is selected from the group consisting of araA, araB, araD, prpB, prpD, rhaA, rhaB, rhaD, xylA, and xylB.

The method of the invention further comprising subjecting the first solution to centrifugation; and this method of the invention wherein the centrifugation is at a force of: 900×g, or between 900×g and 25,000×g, or between 900×g and 7,000×g, or between 2,000×g and 20,000×g, or at 3,300×g, or between 3,300×g and 20,000×g, or at 7,000×g, or between 7,000×g and 20,000×g; and this method of the invention wherein said first solution is separated into a soluble fraction and a pellet, wherein said pellet comprises at least some of said at least one gene product; and this method of the invention further comprising recovering at least some of said at least one gene product from said pellet; and this method of the invention wherein at least some of said at least one gene product present in said pellet is placed in a solubilization solution.

The method of the invention wherein said solubilization solution comprises at least one chaotropic agent; and this method of the invention wherein said at least one chaotropic agent is selected from the group consisting of n-butanol, ethanol, guanidinium chloride, guanidine hydrochloride, lithium perchlorate, lithium acetate, magnesium chloride, phenol, 2-propanol, sodium dodecyl sulfate, thiourea, and urea; and this method of the invention wherein said at least one chaotropic agent is selected from the group consisting of urea at a concentration between 2M and 10M and guanadine hydrochloride at a concentration between 2M and 8M, or is urea at a concentration between 7M and 8M.

The method of the invention further comprising reducing the concentration of said at least one chaotropic agent in the solubilization solution; and this method of the invention wherein the concentration of said at least one chaotropic agent in the solubilization solution is reduced to 50% or less of its initial concentration in the solubilization solution, and/or wherein the initial concentration of said at least one chaotropic agent in the solubilization solution is urea at a concentration between 7M and 8M and the concentration of said at least one chaotropic agent is reduced to urea at a concentration between 3M and 4M; and this method of the invention wherein the reduction of the concentration of said at least one chaotropic agent in the solubilization solution is accomplished by a method selected from the group consisting of dialysis, dilution, and diafiltration; and this method of the invention further comprising incubating the solubilization solution comprising a reduced concentration of said at least one chaotropic agent for a period of time selected from the group consisting of at least one hour, two hours, five hours, 10 hours, 12 hours, 15 hours, between 12 and 24 hours, 24 hours, between 24 and 72 hours, 36 hours, 48 hours, 72 hours, between 72 and 120 hours, and 120 hours.

The method of the invention further comprising recovering at least some of said at least one gene product from said solubilization solution; and this method of the invention wherein the amount of said at least one gene product recovered from said solubilization solution is at least 50%, or at least 60%, or at least 70%, or at least 80% of the total amount of said at least one gene product present in said first solution, and/or wherein at least some of the said at least one gene product recovered from said solubilization solution has a property selected from the group consisting of properly formed disulfide bonds and gene product activity; and this method of the invention wherein at least 50%, or at least 60%, or at least 70%, or at least 80%, or at least 85%, or at least 90% of the at least one gene product recovered from said solubilization solution has properly formed disulfide bonds.

The method of the invention further comprising chromatographic purification of said at least one gene product; and this method of the invention wherein the chromatographic purification is immobilized metal affinity chromatography (IMAC); and this method of the invention wherein the chromatographic purification utilizes a Ni-NTA column.

The method of the invention wherein said at least one gene product is not contacted with a reducing agent.

A further aspect of the invention is a polypeptide comprising an amino acid sequence selected from the group consisting of: (a) any of SEQ ID NOs 12-14 and 27-36; and (b) an amino acid sequence that shares at least 70% (or at least 80%, or at least 90%) amino acid sequence identity across at least 50% (or at least 60%, or at least 70%, or at least 80%, or at least 90%) of the length of any of the amino acid sequences of (a).

| | | | |
|---|---|---|---|
| M: | Molecular weight markers | | |
| Lane 1: | Total protein (5X) | no DTT | (non-reduced) |
| Lane 2: | Total protein (5X) | +DTT | (reduced) |
| Lane 3: | Solubilized pellet (5X) | no DTT | (non-reduced) |
| Lane 4: | Solubilized pellet (5X) | +DTT | (reduced) |
| Lane 5: | Solubilized pellet (10X) | no DTT | (non-reduced) |
| Lane 6: | Solubilized pellet (10X) | +DTT | (reduced) |

Figure 2:
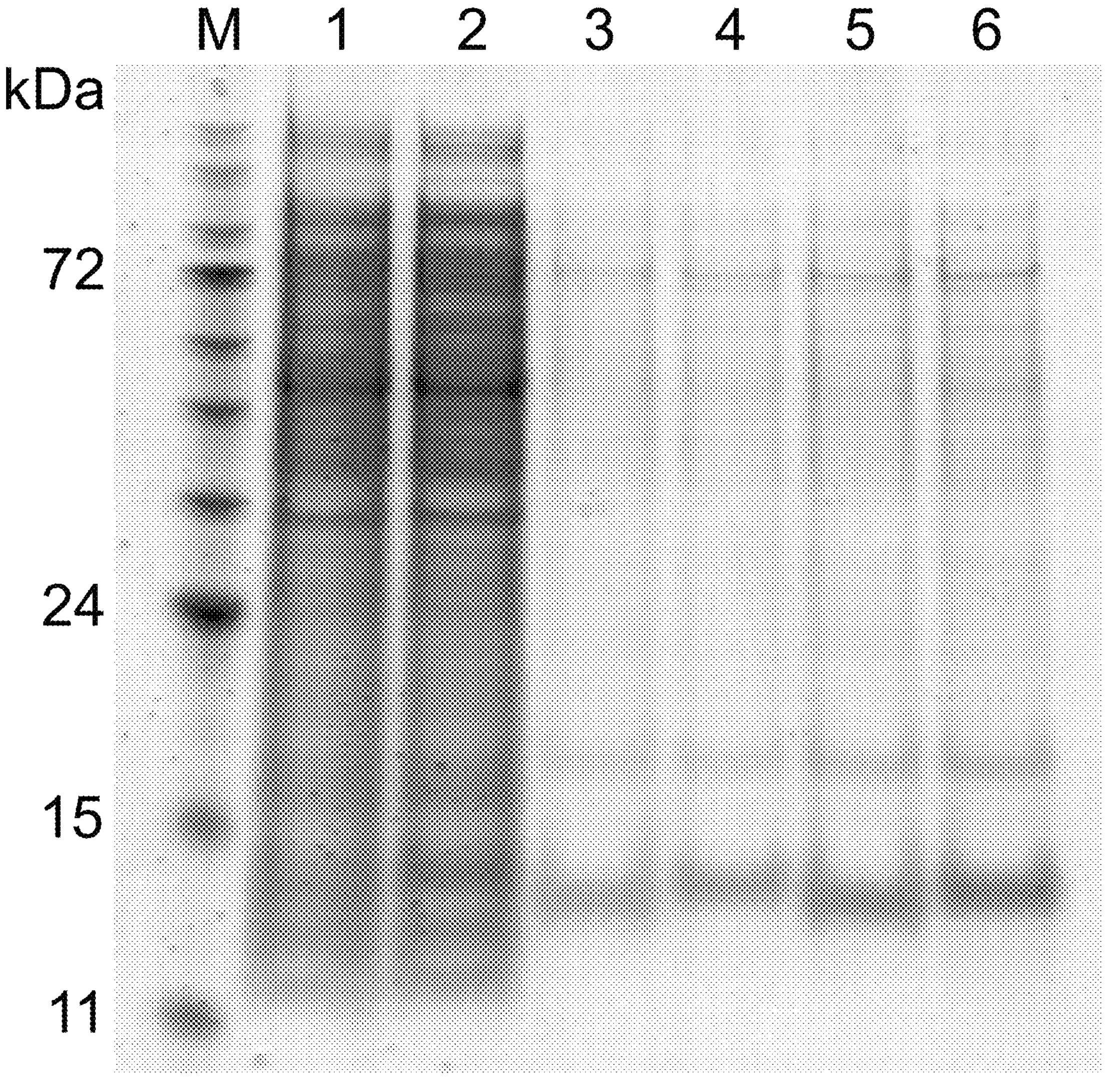
FIG. 2 shows that CPBpro_lispro proinsulin, expressed and solubilized according to the methods of the invention, contains disulfide bonds. CPBpro_lispro proinsulin solubilized with 8M urea was analyzed by polyacrylamide gel electrophoresis on a 12% Bis-Tris gel. Host cells were lysed at a concentration five times ('5×') or ten times ('10×') greater than that of the host cell culture.

Treating the solubilized CPBpro_lispro proinsulin with the reducing agent DTT caused the solubilized CPBpro_lispro proinsulin to migrate at a slightly slower rate on the gel, indicating that the DTT treatment reduced disulfide bonds present in the non-reduced solubilized CPBpro_lispro proinsulin. FIG. 2 also shows that pelleting solubilizable CPBpro_lispro proinsulin complexes allows the majority of the potentially contaminating proteins present in the host cell lysate (Lanes 1 and 2) to be removed from the solubilizable pellet, resulting in a significantly purified preparation of solubilized CPBpro_lispro proinsulin (Lanes 3 through 6).

Figure 3:
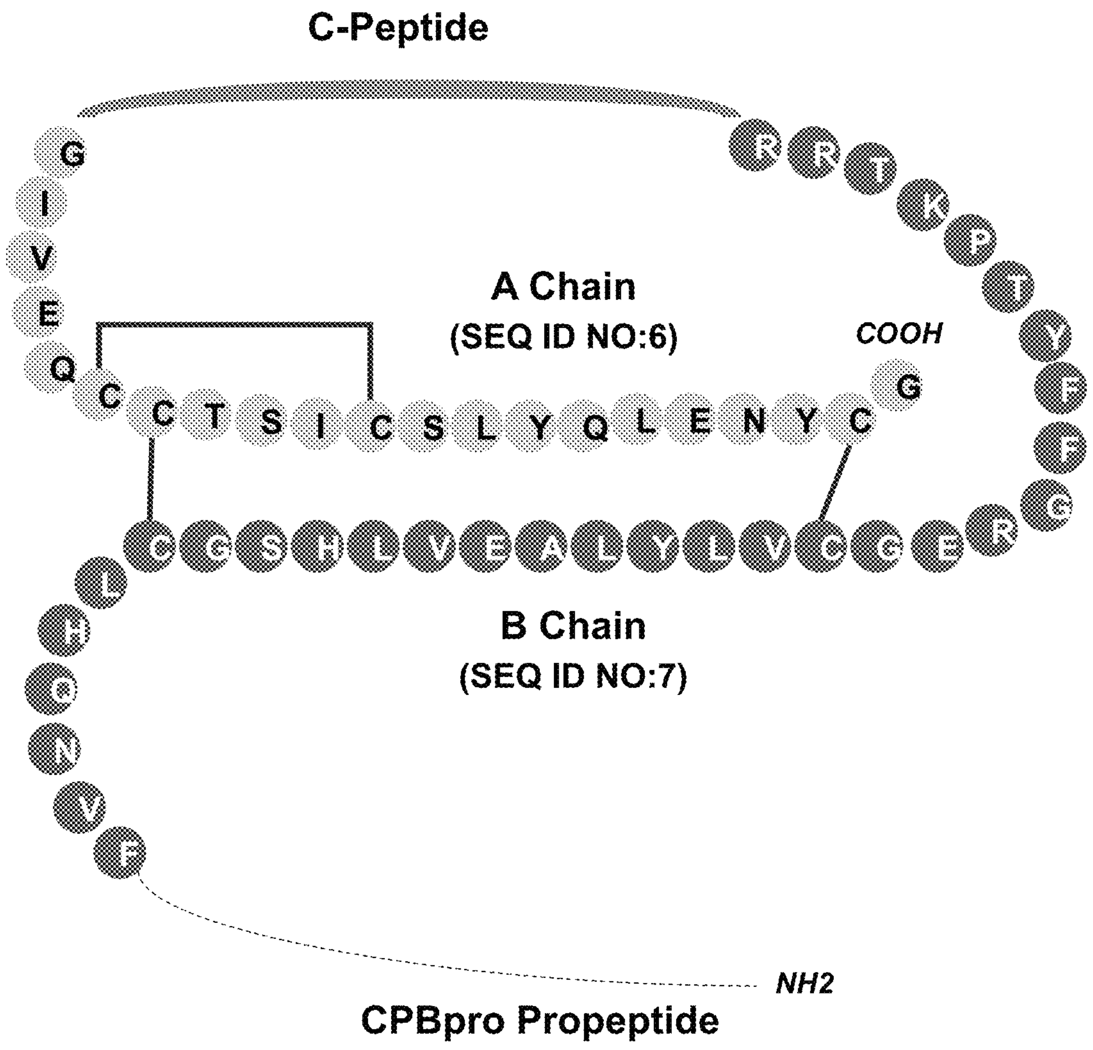

FIG. 3 is a schematic representation of a CPBpro_glargine proinsulin polypeptide. The amino acids of the A and B chains are shown as light gray and dark gray circles, respectively. The N-terminal CPBpro propeptide is shown as a dashed line; the C-peptide (or 'connecting peptide') that connects the A and B chains is shown as a gray arch. The solid dark gray lines between cysteine residues in the A and B chains, and connecting two cysteines within the A chain, represent the disulfide bonds present in correctly folded insulin glargine.

Figure 4:
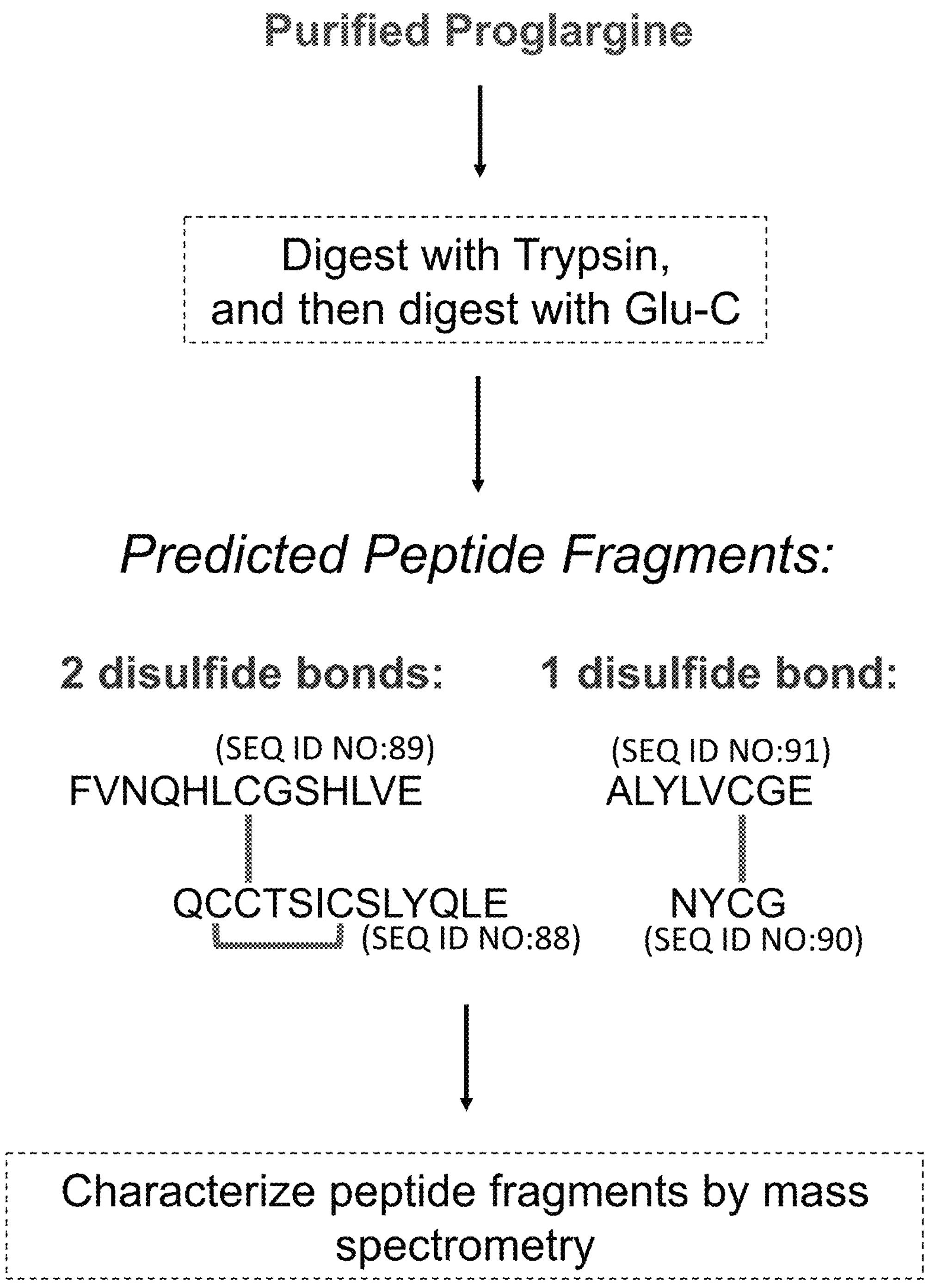

FIG. 4 is a schematic diagram representing the digestion of purified CPBpro_glargine proinsulin with trypsin and with glutamyl endopeptidase ('Glu-C') to generate cross-linked peptide fragments for characterization by mass spectometry. Disulfide bonds are represented by solid dark gray lines connecting cysteine residues.

Figure 5:
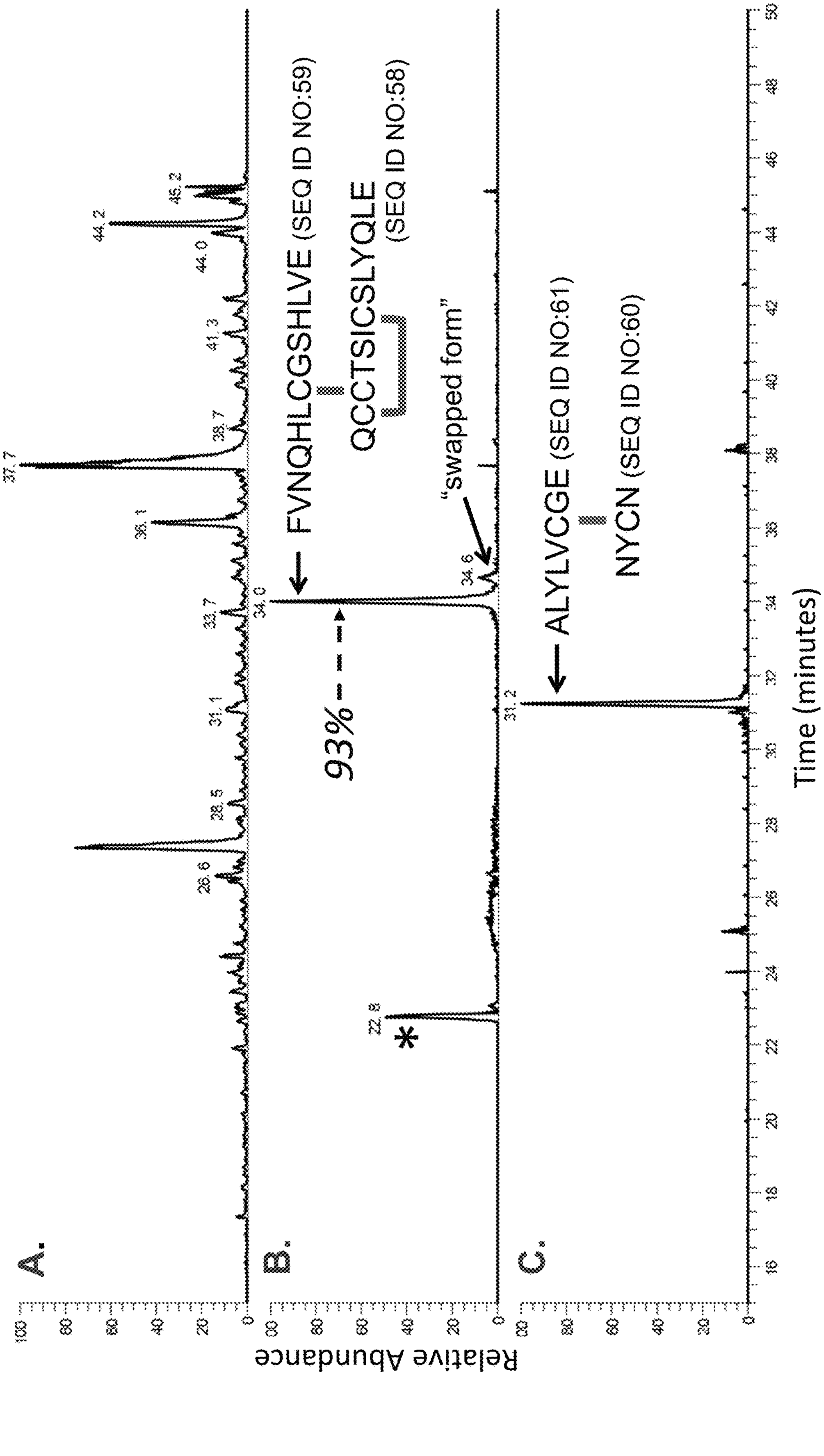

FIG. 5 is a set of three mass spectrometry chromatograms showing that 93% of the CPBpro_glargine proinsulin, purified only by solubilization from pelleted solubilizable complexes, has the correct formation of disulfide bonds and is therefore properly folded. Panel A: base peak chromatogram (non-reduced); Panel B: extracted ion chromatogram (non-reduced, +/−5 ppm) showing peaks corresponding to the peptide fragment with two disulfide bonds; Panel C: extracted ion chromatogram (non-reduced, +/−5 ppm) showing a peak corresponding to the peptide fragment with one disulfide bond. Arrows indicate the peak corresponding to the indicated peptide fragment, as determined by comparison to the chromatogram produced by an insulin glargine standard. The arrow labeled "swapped form" indicates a minor peak corresponding to the conformation where the cysteines at positions A6 and A7 of mature insulin (see FIG. 4) have "swapped" disulfide bonding partners. *: The asterisk marks a peak that is not in the correct charge state to be from CPBpro_glargine proinsulin.

DETAILED DESCRIPTION OF THE INVENTION

The problem of producing gene products such as recombinant proteins at commercial scale and in active form is addressed by providing the methods for protein expression and purification described herein. We have found that gene products such as polypeptides, when expressed in host cells to sufficient gene product density and in a manner that permits the gene product to be properly folded when expressed, and to have any disulfide bonds properly formed, will form solubilizable complexes that are easily purified away from other cell components and then solubilized to produce properly folded and presumably active gene product. These methods of the invention, directed to the production of gene product in the form of such solubilizable complexes, and the subsequent purification of properly folded gene product, has the advantage of not requiring a procedure involving contacting the gene product with a reducing agent.

As another aspect of the invention, methods are provided for the direct solubilization of polypeptides produced by host cells in the form of solubilizable complexes, without an initial centrifugation step to separate the insoluble and soluble fractions following cell lysis, and allowing for the purification of properly folded and/or active polypeptides that form disulfide bonds without the need for contacting such polypeptides with a reducing agent.

The proper folding of a gene product, such as a gene product comprising one or more polypeptides, is consistent with any disulfide bonds in that gene product being formed in the proper location within that gene product. Therefore, determining whether a gene product is properly folded can involve characterization of any disulfide bonds present in the gene product, as described further in Examples 2C and 8, to assess whether those disulfide bonds are properly formed. A properly formed disulfide bond is one that, when assayed, is a covalent bond joining two sulfur atoms, and that when present within a polypeptide or between two polypeptides, is a covalent bond that links (or connects) the sulfur atoms of two sulfur-containing amino acid residues (such as cysteine or Cys residues) that are linked by a disulfide bond in the desired form of the gene product comprising the polypeptide(s). For example, for glargine proinsulin as shown in FIG. 3, the three properly formed disulfide bonds are those that connect the Cys residues at positions 6 and 11 of SEQ ID NO:6, at position 7 of SEQ ID NO:6 and position 7 of SEQ ID NO:7, and at position 20 of SEQ ID NO:6 and position 19 of SEQ ID NO:7.

Active gene products include any gene products with measurable activity of the type associated with the desired form of the gene product. For example, an active insulin gene product can have measurable insulin receptor binding activity, or measurable anti-insulin antibody binding activity, or any other type of activity associated with the desired form of the insulin gene product.

Recovery of properly folded and/or active forms of proteins from inclusion bodies typically includes treatment with at least one reducing agent. The term 'reducing agent', as used herein, includes chemical substances (not proteins) with reducing potentials that are more negative than −0.26 V at pH 7.0 and 25 degrees C., such as DTE (dithioerythritol), DTT (dithiothreitol), and TCEP (tris(2-carboxyethyl)-phosphine); the term 'reducing agent' therefore does not include L-cysteine ('L-cys') or glutathione. Unlike recovery of gene product from inclusion bodies, the solubilization methods disclosed herein—which do not involve the use of reducing agents—result in substantially greater recovery of gene product, for example recovery of at least 50%, 60%, 70%, or 80% of the total gene product material present in the host cell lysate, as calculated by the methods described in Example 7. Given the high yields of gene product (5-20 g/L)

achieved in the cell lysate, the solubilization methods described herein (as in Examples 1-3), can result in yields of 4-16 g/L of gene product.

In order for the host cell to produce gene product(s) in the form of solubilizable complexes, it is most advantageous to utilize a suitable combination of the following aspects I-IV of gene product expression, as described in detail herein:

I. The gene product(s) to be produced, including any transporters, cofactors, chaperones, and/or tags or propeptides to be used in expression of the desired gene product(s).

II. The expression construct(s) to be used for expression of the gene product(s).

III. The host cells to be used to express the expression construct(s) encoding the gene product(s).

IV. The conditions for host cell growth and the induction of expression.

Section V. describes solubilization and purification methods of the invention.

The following patent publications and application(s), all of which are expressly incorporated by reference herein, provide additional examples of gene products, expression constructs, host cells, and growth and induction conditions that can be employed in the production of solubilizable complexes suitable for the purification methods of the invention: U.S. Pat. No. 9,617,335B2, "Inducible Coexpression System"; WO2016205570A1, "Vectors for Use in an Inducible Coexpression System"; and International Application PCT/US2016/067064, "Cytoplasmic Expression System".

I. Products Made by the Methods of the Invention

There is broad versatility in utilizing the gene expression and gene product purification methods of the present invention in numerous expression applications, and in the properties of the products.

Gene products produced by the methods of the invention can comprise any, or more than one, of the following: 1-antitrypsin; 2C4; activin; addressins; alkaline phosphatase; anti-CD11a; anti-CD18; anti-CD20; anti-clotting factors such as Protein C; anti-HER-2 antibody; anti-IgE; anti-IgG; anti-VEGF; antibodies and antibody fragments; antibodies to ErbB2 domain(s) such as 2C4 (WO 01/00245 hybridoma ATCC HB-12697), which binds to a region in the extracellular domain of ErbB2 (e.g., any one or more residues in the region from about residue 22 to about residue 584 of ErbB2, inclusive); Apo2 ligand (Apo2L); atrial naturietic factor; BDNF; beta-lactamase; bombesin; bone morphogenetic protein (BMP); botulinum toxin; brain IGF-I; calcitonin; cardiotrophins (cardiac hypertrophy factor) such as cardiotrophin-1 (CT-1); CD proteins such as CD-3, CD-4, CD-8, and CD-19; clotting factors such as factor VIIIC, factor IX, tissue factor, and von Willebrands factor; colony stimulating factors (CSFs), e.g., M-CSF, GM-CSF, and G-CSF; cytokines; decay-accelerating factor; des(1-3)-IGF-I (brain IGF-I); DNase; enkephalinase; epidermal growth factor (EGF); erythropoietin; fibroblast growth factor such as aFGF and bFGF; follicle-stimulating hormone; glucagon; gp120; ghrelin; growth hormone, including human growth hormone or bovine growth hormone; growth-hormone releasing factor; hemopoietic growth factor; homing receptors; HSA; IGF-I; IGF-II; immunotoxins; inhibin; insulin chains (insulin A-chain, insulin B-chain) or proinsulin; insulin-like growth factor binding proteins; insulin-like growth factor-I and -II (IGF-I and IGF-II); integrin; interferon such as interferon-alpha, -beta, and -gamma; interleukins (ILs), e.g., IL-1 to IL-10; leptin; lipoproteins; lung surfactant; luteinizing hormone; metreleptin; mouse gonadotropin-associated peptide; mullerian-inhibiting substance; nerve growth factor (NGF); neurotrophic factor such as brain-derived neurotrophic factor (BDNF), neurotrophin-3, -4, -5, or -6 (NT-3, NT-4, NT-5, or NT-6); osteoinductive factors; parathyroid hormone; plasminogen activator, such as urokinase or human urine or tissue-type plasminogen activator (t-PA); platelet-derived growth factor (PDGF); prorelaxin; protein A or D; receptors for hormones or growth factors; regulatory proteins; relaxin A-chain; relaxin B-chain; rennin; rheumatoid factors; serum albumin, such as human serum albumin (HSA) or bovine serum albumin (BSA); superoxide dismutase; surface-membrane proteins; T-cell receptors; TGF-beta; thrombin; thrombopoietin; thyroid-stimulating hormone; transforming growth factor (TGF) such as TGF-alpha and TGF-beta, including TGF-1, TGF-2, TGF-3, TGF-4, or TGF-5; transport proteins; tumor necrosis factor-alpha and -beta; urokinase; vascular endothelial growth factor (VEGF); viral antigens such as, for example, a portion of the AIDS envelope; fragments of any of the above; and any of the above or a fragment thereof covalently bound to one or more of the proteins above or fragments thereof or functional domains such as: an antibody Fc domain, an antibody single-chain variable fragment (scFv), a domain with enzymatic activity (such as a glycoside hydrolase domain or a kinase domain), an EVH1 (Ena/Vasp homology, or WH1) domain, a PAS (Per-Arnt-Sim) domain, a PDZ domain, a POU (Pit-1, Oct, Unc-86) domain, an SPR (Spread, Sprouty) domain, a VWFC (Von Willebrand factor, type C or VWC) domain, or a zinc-finger domain (for example, a RING-finger domain).

Gene products produced by the methods of the invention can include any, or more than one, of the following insulin polypeptides. An insulin polypeptide produced by the methods of the invention comprises in some embodiments the amino acid sequence of a mature A chain or of a mature B chain of insulin, and in other embodiments comprises both a mature A chain and a mature B chain. A proinsulin polypeptide comprises a mature A chain of insulin and a mature B chain of insulin. Insulin polypeptide chains in certain embodiments comprise one or more of any of the naturally occurring amino acid sequences of insulins, or fragments thereof, and in other embodiments comprise one or more insulin analogue amino acid sequences, or fragments thereof, and in further embodiments comprise combinations of naturally occurring insulin amino acid sequences and/or insulin analogue amino acid sequences. Examples of naturally occurring insulin amino acid sequences and insulin analogue amino acid sequences are shown in Table 1.

Table 1. Insulin Chain Amino Acid Sequences

A: mature A chain; B: mature B chain;

Underlining: differences from native human insulin; *: modified residue

TABLE 1

Insulin Chain Amino Acid Sequences

| Name: | Description: | Sequence: |
|---|---|---|
| Insulin (regular) | Native human insulin | A: GIVEQCCTSICSLYQLENYCN (SEQ ID NO: 1)<br>B: FVNQHLCGSHLVEALYLVCGE RGFFYTPKT (SEQ ID NO: 2) |

TABLE 1-continued

Insulin Chain Amino Acid Sequences

| Name: | Description: | Sequence: |
|---|---|---|
| Isophane insulin | Neutral protamine Hagedorn insulin; formulated to be intermediate-acting | A: GIVEQCCTSICSLYQLENYCN (SEQ ID NO: 1) B: FVNQHLCGSHLVEALYLVCGE RGFFYTPKT (SEQ ID NO: 2) |
| Insulin lispro | Insulin analogue, rapid-acting | A: GIVEQCCTSICSLYQLENYCN (SEQ ID NO: 1) B: FVNQHLCGSHLVEALYLVCGE RGFFYTKPT (SEQ ID NO: 3) |
| Insulin aspart | Insulin analogue, fast-acting | A: GIVEQCCTSICSLYQLENYNC (SEQ ID NO: 1) B: FVNQHLCGSHLVEALYLVCGE RGFFYTDKT (SEQ ID NO: 4) |
| Insulin glulisine | Insulin analogue, rapid-acting | A: GIVEQCCTSICSLYQLENYCN (SEQ ID NO: 1) B: FVKQHLCGSHLVEALYLVCGE RGFFYTPET (SEQ ID NO: 5) |
| Insulin glargine | Insulin analogue, slow-release, long-acting | A: GIVEQCCTSICSLYQLENYCG (SEQ ID NO: 6) B: FVNQHLCGSHLVEALYLVCGE RGFFYTPKTRR (SEQ ID NO: 7) |
| Insulin degludec | Insulin analogue, long-acting | A: GIVEQCCTSICSLYQLENYCN (SEQ ID NO: 1) B: FVNQHLCGSHLVEALYLVCGE RGFFYTPK* (SEQ ID NO: 8) |
| Insulin detemir | Insulin analogue, long-acting | A: GIVEQCCTSICSLYQLENYCN (SEQ ID NO: 1) B: FVNQHLCGSHLVEALYLVCGE RGFFYTPK* (SEQ ID NO: 9) |

A: mature A chain;
B: mature B chain;
Underlining: differences from native human insulin;
*: modified residue Preproinsulin polypeptides can comprise the following components, preferably in the following N-terminal to C-terminal order: a prepeptide, which can be a signal peptide that is cleaved off during protein expression by the host cell signal peptidase; a propeptide; the B-chain; a C-peptide (or 'connecting peptide'); and the A-chain. Preproinsulin polypeptides can also comprise the A- and B-chains in a different N-terminal to C-terminal order, for example: a prepeptide; a propeptide; the A-chain; a C-peptide; and the B-chain. For proinsulin polypeptides that are to be expressed in the cytoplasm of host cells, a prepeptide comprising a signal sequence is not present. A diagram of a proinsulin glargine polypeptide is shown in FIG. 3. Examples of C-peptides include the C-peptide of human insulin (amino acids 55 through 89 of NCBI Reference Sequence NP_001278826.1, SEQ ID NO:10), and an artificial C-peptide RRYPGDVKR (SEQ ID NO:11) (Chang et al., "Human insulin production from a novel mini-proinsulin which has high receptor-binding activity", Biochem J 1998 Feb. 1; 329 (Pt 3): 631-635). Additional C-peptide amino acid sequences that can be used in proinsulin polypeptides are artificial variants of the human C-peptide (SEQ ID NOs 12 and 13), and an artificial C-peptide RRDDNLER (SEQ ID NO:14). C-peptide amino acid sequences are generally presented herein as including the terminal arginine and lysine residues that are typically cleaved off when the proinsulin polypeptide is converted to mature insulin through a tryptic digestion process. An exception is the C-peptide of proinsulin glargine as shown in FIG. 3: because the mature B-chain of insulin glargine has two arginine (R) residues, these arginine residues are depicted in FIG. 3 as being part of the mature B-chain of insulin glargine rather than as part of the C-peptide.

Gene products produced by the methods of the invention can include leptin and/or metreleptin polypeptides. An example of a leptin polypeptide, also called metreleptin, is shown in SEQ ID NO:15, and corresponds to mature human leptin with a methionine residue at its N-terminus. Other examples of leptin polypeptides comprise an amino acid sequence lacking the N-terminal methionine residue, such as amino acids 2 through 147 of SEQ ID NO:15. A common isoform of leptin has a methionine residue at position 74 of SEQ ID NO:15 instead of a valine residue. A leptin polypeptide produced by the methods of the invention comprises in some embodiments the amino acid sequence of a leptin polypeptide with a methionine residue at its N-terminus (metreleptin), and in other embodiments with a tag, linker, or other propeptide amino acid sequence (as described further below) added to the N-terminus of the leptin polypeptide, in some embodiments with, and in other embodiments without, inclusion of the methionine at the N-terminus of the metreleptin amino acid sequence.

Signal Peptides.

Polypeptide gene products produced by the methods of the invention can have or lack signal peptides. In certain embodiments of the invention, polypeptide gene products lack signal peptides because it is advantageous for such gene products to be retained in the oxidizing cytoplasm of the host cell. Signal peptides (also termed signal sequences, leader sequences, or leader peptides) are characterized structurally by a stretch of hydrophobic amino acids, approximately five to twenty amino acids long and often around ten to fifteen amino acids in length, that has a tendency to form a single alpha-helix. This hydrophobic stretch is often immediately preceded by a shorter stretch enriched in positively charged amino acids (particularly lysine). Signal peptides that are to be cleaved from the mature polypeptide typically end in a stretch of amino acids that is recognized and cleaved by signal peptidase. Signal peptides that direct insertion of the polypeptide gene product into membranes, sometimes referred to as signal anchor sequences, can lack the amino acid sequence that is cleaved by signal peptidase and in that case are retained in the polypeptide gene product. Signal peptides can often be characterized functionally by the ability to direct transport of a polypeptide, either co-translationally or post-translationally, out of the cytoplasm and, for example, through the plasma membrane of prokaryotes (or the inner membrane of grain negative bacteria like *E. coli*), or into the endoplasmic reticulum of eukaryotic cells. The degree to which a signal peptide enables a polypeptide to be transported into the periplasmic space of a host cell like *E. coli*, for example, can be determined by separating periplasmic proteins from proteins retained in the cytoplasm, using a method such as that provided in Example 9 below.

Tags and Other Polypeptide Sequences that can be Used with Gene Products.

Tags.

Gene products to be expressed by the methods of the invention can be designed to include molecular moieties that aid in the purification and/or detection of the gene products. Many such moieties are known in the art; as one example, a polypeptide gene product can be designed to include a polyhistidine 'tag' sequence—a run of six or more histidines, preferably six to ten histidine residues, and most preferably six histidines ('6×His')—at its N- or C-terminus. The presence of a polyhistidine sequence on the end of a polypeptide allows it to be bound by cobalt- or nickel-based affinity media, and separated from other polypeptides. The polyhistidine tag sequence can be removed by exopeptidases.

Additional tags, expressed at the N-terminal end of the amino acid sequence of a polypeptide gene product produced by the methods of the invention, comprise in certain embodiments: (1) the self-cleaving N-terminal portions ($N^{pro}$) of polyproteins from pestiviruses such as Hog cholera virus (strain Alfort) (SEQ ID NO:16), also called classical swine fever virus (CSFV), and from border disease virus (BDV) and bovine viral diarrhea virus (BVDV), and fragments thereof; and/or (2) small ubiquitin-related modifier (SUMO) (SEQ ID NO:17, SwissProt P55853.1) Any N-terminal tag may itself be further tagged at its N-terminus with a polyhistidine tag such as 6×His, allowing for initial purification of the tagged polypeptide on a nickel column, followed by self-cleavage of tags such as $N^{pro}$, or enzymatic cleavage of the SUMO N-terminal tag by SUMO protease, respectively, and elution of the freed polypeptide from the column. In one embodiment of this method, the SUMO protease polypeptides are also fusion proteins comprising 6×His tags, allowing for a two-step purification: in the first step, the expressed 6×His-SUMO-tagged polypeptide is purified by binding to a nickel column, followed by elution from the column. In the second step, the SUMO tags on the purified polypeptides are cleaved by the 6×His-tagged SUMO protease, and the SUMO protease—polypeptide reaction mixture is run through a second nickel column, which retains the SUMO protease but allows the now untagged polypeptide to flow through.

As another example, fluorescent protein sequences can be expressed as part of a polypeptide gene product, with the amino acid sequence for the fluorescent protein preferably added at the N- or C-terminal end of the amino acid sequence of the polypeptide gene product. The resulting fusion protein fluoresces when exposed to light of certain wavelengths, allowing the presence of the fusion protein to be detected visually. A well-known fluorescent protein is the green fluorescent protein of *Aequorea victoria*, and many other fluorescent proteins are commercially available, along with nucleotide sequences encoding them.

Linkers.

Linkers are polypeptides that are used to connect two other polypeptides. Examples of linker polypeptides that form alpha-helices are provided as SEQ ID NO:18 and SEQ ID NO:19 (Amet et al., "Insertion of the designed helical linker led to increased expression of Tf-based fusion proteins", Pharm Res 2009 March; 26(3): 523-528; doi: 10.1007/s11095-008-9767-0; Epub 2008 Nov. 11).

Cleavage Sequences.

Cleavage sequences are discrete amino acid sequences that can be acted upon by chemical reagents or enzymes to effect cleavage of the polypeptide containing the cleavage sequence. One or more of these sequences can be introduced between a tag or propeptide sequence and the amino acid sequence of a polypeptide gene product, to allow the tag or propeptide to be cleaved off during the process of purification of the gene product. Examples of cleavage sequences include the amino sequences DP and GGDPGGG (SEQ ID NO:20, which can be cleaved by treatment with formic acid at the bond between D (Asp) and P (Pro). Certain acid-cleavable sequences are present within particular propeptides described below (SEQ ID NOs 33-35). Additional examples are amino acid sequences cleavable by proteases such as TEV (tobacco etch virus) protease (cleavage sequence ENLYFQGG (SEQ ID NO:21)), enterokinase (cleavage sequence DDDDKG (SEQ ID NO:22)), and thrombin (cleavage sequence LVPRGS (SEQ ID NO:23)).

Propeptides.

The propeptides described herein can be attached to polypeptide gene products, either N-terminal or C-terminal to the amino acid sequence of a polypeptide gene product, or both, and attached either directly to the amino acid sequence of a polypeptide gene product, or with other polypeptide sequences such as linkers or tags placed between the propeptide and the polypeptide gene product. Examples of polypeptides that can be used as propeptides include mammalian carboxypeptidase B precursor proteins (described further below) and maltose binding protein or 'MBP' (UniProtKB/Swiss-Prot: POAEX9.1, SEQ ID NO:24), which has a signal sequence; amino acids 2-26 of SEQ ID NO:24 can be removed to generate a propeptide that will remain localized in the cell cytoplasm. Another polypeptide that has been used as a propeptide is the family 9 carbohydrate-binding module from *Thermotoga maritima* xylanase 10a or 'CBM9' (SEQ ID NO:25, amino acids 700-868 of UniProtKB/Swiss-Prot: Q60037, Notenboom et al., "Crystal structures of the family 9 carbohydrate-binding module from *Thermotoga maritima* xylanase 10A in native and ligand-bound forms", Biochemistry 2001 May 29; 40(21): 6248-6256).

Carboxypeptidase B Propeptide (CPBpro).

The typical mammalian carboxypeptidase B precursor protein has a signal peptide at its N-terminus, followed by a propeptide of 95 amino acids having an arginine residue at its C-terminus; this propeptide which is also termed the carboxypeptidase B activation domain is cleaved from the remainder of the carboxypeptidase B enzyme (EC 3.4.17.2) by tryptic hydrolysis, activating the enzyme (Coll et al., "Three-dimensional structure of porcine procarboxypeptidase B: a structural basis of its inactivity", EMBO J 1991 January; 10(1): 1-9). The amino acid sequence of human carboxypeptidase B precursor protein or CPBpro is provided as SEQ ID NO:26.

The terms 'CPBpro' and 'CPBpro propeptides' are used herein to refer to carboxypeptidase B propeptides, including the novel variants disclosed herein. CPBpro propeptides can be used in the production of recombinant polypeptides, fused for example at the C-terminal arginine residue of the CPBpro propeptide to the desired N-terminal residue of the polypeptide of interest: following expression of the CPBpro polypeptide, the CPBpro propeptide can be cleaved from the polypeptide of interest by trypsin to generate the desired N-terminus. Examples of variant CPBpro propeptides include SEQ ID NOs 27-36, and a further propeptide is provided having the amino acid sequence of SEQ ID NO:37.

Formation of Solubilizable Gene Products.

In certain instances, expression of gene products using the expression methods described herein results in the formation of solubilizable gene product complexes without the need for the addition of tags or other polypeptides to the gene product. For example, in small-volume experiments, the coexpression of metreleptin (SEQ ID NO:15) with the Erv1p sulfhydryl oxidase (SEQ ID NO:38, described below) according to expression methods described herein resulted in most (about 70%) of the expressed metreleptin forming solubilizable complexes; similar coexpression of Erv1p with a gene product (SEQ ID NO:39) formed by addition of a CPBpro variant propeptide (SEQ ID NO:27) to metreleptin (SEQ ID NO:15) resulted in a larger portion of the gene product (about 84%) forming solubilizable complexes. For optimization of expression of gene product(s) in solubilizable complexes, the gene product(s) can first be expressed without modification, and the amount of solubilizable complexes produced can be determined. The effect of the addition of various polypeptide sequences (tags, propeptides, optionally in combination, and optionally in further combination with linker and/or cleavage sequences) to polypeptide gene product(s) can then be assessed, preferably in small-volume expression experiments, to determine whether a larger portion of the desired gene product(s) is then expressed as solubilizable complexes.

Disulfide Bonds.

Gene products produced by the methods of the invention are in some instances polypeptides that form disulfide bonds. The numbers and locations of disulfide bonds formed by a polypeptide can be determined by methods such as that of Example 8 below. The number of disulfide bonds for a gene product such as a polypeptide is the total number of intramolecular and intermolecular bonds formed by that gene product when it is present in a functional product. For example, a light chain of a human IgG antibody typically has three disulfide bonds (two intramolecular bonds and one intermolecular bond), and a heavy chain of a human IgG antibody typically has seven disulfide bonds (four intramolecular bonds and three intermolecular bonds). In certain embodiments of the invention, a gene product produced by methods of the invention is a polypeptide that forms at least one and fewer than twenty disulfide bonds, or at least two and fewer than seventeen disulfide bonds, or at least seventeen and fewer than fifty disulfide bonds, or at least three and fewer than ten disulfide bonds, or at least three and fewer than eight disulfide bonds, or is a polypeptide that forms a number of disulfide bonds selected from the group consisting of one, two, three, four, five, six, seven, eight, and nine disulfide bonds.

Glycosylation.

Gene products produced by the methods of the invention may be glycosylated or unglycosylated. In one embodiment of the invention, the gene products are polypeptides. Glycosylated polypeptides are polypeptides that comprise a covalently attached glycosyl group, and include polypeptides comprising all the glycosyl groups normally attached to particular residues of that polypeptide (fully glycosylated polypeptides), partially glycosylated polypeptides, polypeptides with glycosylation at one or more residues where glycosylation does not normally occur (altered glycosylation), and polypeptides glycosylated with at least one glycosyl group that differs in structure from the glycosyl group normally attached to one or more specified residues (modified glycosylation). An example of modified glycosylation is the production of "defucosylated" or "fucose-deficient" polypeptides, polypeptides lacking fucosyl moieties in the glycosyl groups attached to them, by expression of polypeptides in host cells lacking the ability to fucosylate polypeptides. Unglycosylated polypeptides are polypeptides that do not comprise a covalently bound glycosyl group. An unglycosylated polypeptide can be the result of deglycosylation of a polypeptide, or of production of an aglycosylated polypeptide. Deglycosylated polypeptides can be obtained by enzymatically deglycosylating glycosylated polypeptides, whereas aglycosylated polypeptides can be produced by expressing polypeptides in host cells that do not have the capability to glycosylate polypeptides, such as prokaryotic cells or cells in which the function of at least one glycosylation enzyme has been eliminated or reduced. In a particular embodiment, the expressed polypeptides are aglycosylated, and in a more specific embodiment, the aglycosylated polypeptides are expressed in prokaryotic cells such as *E. coli.*

Other Modifications of Gene Products.

Gene products produced by the methods of the invention may be covalently linked to other types of molecules. Examples of molecules that may be covalently linked to gene products, without limiting the scope of the invention, include polypeptides (such as those present in receptors, ligands, cytokines, growth factors, polypeptide hormones, DNA-binding domains, protein interaction domains such as PDZ domains, kinase domains, antibodies, and fragments of any such polypeptides); water-soluble polymers (such as polyethylene glycol (PEG), carboxymethylcellulose, dextran, polyvinyl alcohol, polyoxyethylated polyols (such as glycerol), polyethylene glycol propionaldehyde, and similar compounds, derivatives, or mixtures thereof); and cytotoxic agents (such as chemotherapeutic agents, growth-inhibitory agents, toxins (such as enzymatically active toxins of bacterial, fungal, plant, or animal origin, or fragments thereof), and radioactive isotopes).

Chaperones.

In some embodiments, desired gene products are coexpressed with other gene products, such as chaperones, that are beneficial to the production of the desired gene product. Chaperones are proteins that assist the non-covalent folding or unfolding, and/or the assembly or disassembly, of other gene products, but do not occur in the resulting monomeric or multimeric gene product structures when the structures are performing their normal biological functions (having completed the processes of folding and/or assembly). Chaperones can be expressed from an inducible promoter or a constitutive promoter within an expression construct, or can be expressed from the host cell chromosome; preferably, expression of chaperone protein(s) in the host cell is at a sufficiently high level to produce coexpressed gene products that are properly folded and/or assembled into the desired product. Examples of chaperones present in *E. coli* host cells are the folding factors DnaK/DnaJ/GrpE, DsbC/DsbG, GroEL/GroES, IbpA/IbpB, Skp, Tig (trigger factor), and FkpA, which have been used to prevent protein aggregation of cytoplasmic or periplasmic proteins. DnaK/DnaJ/GrpE, GroEL/GroES, and ClpB can function synergistically in assisting protein folding and therefore expression of these chaperones in combinations has been shown to be beneficial for protein expression (Makino et al., "Strain engineering for improved expression of recombinant proteins in bacteria", Microb Cell Fact 2011 May 14; 10: 32). When expressing eukaryotic proteins in prokaryotic host cells, a eukaryotic chaperone protein, such as protein disulfide isomerase (PDI) from the same or a related eukaryotic species, is in certain embodiments of the invention coexpressed or inducibly coexpressed with the desired gene product.

One chaperone that can be expressed in host cells is a protein disulfide isomerase from *Humicola insolens*, a soil hyphomycete (soft-rot fungus). An amino acid sequence of *Humicola insolens* PDI is shown as SEQ ID NO:40; it lacks the signal peptide of the native protein so that it remains in the host cell cytoplasm. The nucleotide sequence encoding PDI was optimized for expression in *E. coli*; the expression construct for PDI is shown as SEQ ID NO:41. SEQ ID NO:41 contains a GCTAGC NheI restriction site at its 5' end, an AGGAGG ribosome binding site at nucleotides 7 through 12, the PDI coding sequence at nucleotides 21 through 1478, and a GTCGAC SalI restriction site at its 3' end. The nucleotide sequence of SEQ ID NO:41 was designed to be inserted immediately downstream of a promoter, such as an inducible promoter. The NheI and SalI restriction sites in SEQ ID NO:41 can be used to insert it into a vector multiple cloning site, such as that of the pSOL expression vector (SEQ ID NO:42), described in published US patent application US2015353940A1, which is incorporated by reference in its entirety herein. Other PDI polypeptides can also be expressed in host cells, including PDI polypeptides from a variety of species (*Saccharomyces cerevisiae* (UniProtKB P17967), *Homo sapiens* (UniProtKB P07237), *Mus musculus* (UniProtKB P09103), *Caenorhabditis elegans* (UniProtKB Q17770 and Q17967), *Arabdopsis thaliana* (UniProtKB O48773, Q9XI01, Q9SRG3, Q9LJU2, Q9MAU6, Q94F09, and Q9T042), *Aspergillus niger* (UniProtKB Q12730) and also modified forms of such PDI polypeptides. In certain embodiments of the invention, a PDI polypeptide expressed in host cells of the invention shares at least 70%, or 80%, or 90%, or 95% amino acid sequence identity across at least 50% (or at least 60%, or at least 70%, or at least 80%, or at least 90%) of the length of SEQ ID NO:40, where amino acid sequence identity is determined according to Example 11.

Cellular Transport of Cofactors.

When using the expression systems of the invention to produce gene products that require cofactors for function, it is helpful to use a host cell capable of synthesizing the cofactor from available precursors, or taking it up from the environment. Common cofactors include ATP, coenzyme A, flavin adenine dinucleotide (FAD), $NAD^+$/NADH, and heme. Polynucleotides encoding cofactor transport polypeptides and/or cofactor synthesizing polypeptides can be introduced into host cells, and such polypeptides can be constitutively expressed, or inducibly coexpressed with the gene products to be produced by methods of the invention.

II. Expression Constructs.

Expression constructs are polynucleotides designed for the expression of one or more gene products of interest. Certain gene products of interest are 'heterologous' gene products, that are derived from species that are different from that of the host cell in which they are expressed, and/or are heterologous gene products that are not natively expressed from the promoter(s) utilized within the expression construct, and/or are modified gene products that have been designed to include differences from naturally occurring forms of such gene products. Expression constructs comprising polynucleotides encoding heterologous and/or modified gene products, or comprising a combination of polynucleotides that were derived from organisms of different species, or comprising polynucleotides that have been modified to differ from naturally occurring polynucleotides, are not naturally occurring molecules. Expression constructs can be integrated into a host cell chromosome, or maintained within the host cell as polynucleotide molecules replicating independently of the host cell chromosome, such as plasmids or artificial chromosomes. An example of an expression construct is a polynucleotide resulting from the insertion of one or more polynucleotide sequences into a host cell chromosome, where the inserted polynucleotide sequences alter the expression of chromosomal coding sequences. An expression vector is a plasmid expression construct specifically used for the expression of one or more gene products. One or more expression constructs can be integrated into a host cell chromosome or be maintained on an extrachromosomal polynucleotide such as a plasmid or artificial chromosome. In certain embodiments of the invention, the expression construct is the pSOL expression vector (SEQ ID NO:42).

Expression constructs can comprise certain polynucleotide elements, such as origins of replication, selectable markers, promoters such as constitutive or inducible promoters (described further below), ribosome binding sites, and multiple cloning sites. Examples of these polynucleotide elements are well known in the art, and further descriptions of them can be found in the following patent publications and application(s), all of which are expressly incorporated by reference herein: U.S. Pat. No. 9,617,335B2 and WO2014025663A1, "Inducible Coexpression System"; WO2016205570A1, "Vectors for Use in an Inducible Coexpression System"; and International Application PCT/US2016/067064, "Cytoplasmic Expression System".

Inducible Promoter.

As described further below, there are several different inducible promoters that can be included in expression constructs as part of the expression systems of the invention. Preferred inducible promoters share at least 80% polynucleotide sequence identity (more preferably, at least 90% identity, and most preferably, at least 95% identity) to at least 30 (more preferably, at least 40, and most preferably, at least 50) contiguous bases of a promoter polynucleotide sequence as defined in Table 1 of WO2014025663A1, where percent polynucleotide sequence identity is determined using the methods of Example 11. Under 'standard' inducing conditions (see Example 10), preferred inducible promoters have at least 75% (more preferably, at least 100%, and most preferably, at least 110%) of the strength of the corresponding 'wild-type' inducible promoter of *E. coli* K-12 substrain MG1655, as determined using the quantitative PCR method of De Mey et al. "Promoter knock-in: a novel rational method for the fine tuning of genes", BMC Biotechnol 2010 Mar. 24; 10: 26 (see WO2014025663A1, Example 8A). Within the expression construct, an inducible promoter is placed 5' to (or 'upstream of') the coding sequence for the gene product that is to be inducibly expressed, so that the presence of the inducible promoter will direct transcription of the gene product coding sequence in a 5' to 3' direction relative to the coding strand of the polynucleotide encoding the gene product. The gene products expressed from the inducible promoters within expression constructs are not the gene products natively expressed from these inducible promoters; rather, they are heterologous gene products, with the result that the expression constructs comprising heterologous gene products expressed from inducible promoters are necessarily artificial constructs not found in nature.

Inducible Promoters.

The following is a description of inducible promoters that can be used in expression constructs for expression of gene products, along with some of the genetic modifications that can be made to host cells that contain such expression constructs. Examples of these inducible promoters and related genes are, unless otherwise specified, those derived from *Escherichia coli* (*E. coli*) strain MG1655 (American Type Culture Collection deposit ATCC 700926), which is a substrain of *E. coli* K-12 (American Type Culture Collection deposit ATCC 10798). Table 1 of International Application PCT/US13/53562 (published as WO2014025663A1) lists the genomic locations, in *E. coli* MG1655, of the nucleotide sequences for these examples of inducible promoters and related genes; the WO2014025663A1 publication is incorporated by reference in its entirety herein. Nucleotide and other genetic sequences, referenced by genomic location as in Table 1 of WO2014025663A1, are expressly incorporated by reference herein. Additional information about *E. coli* promoters, genes, and strains described herein can be found in many public sources, including the online EcoliWiki resource, located at ecoliwiki.net.

Arabinose Promoter.

(As used herein, 'arabinose' means L-arabinose.) Several *E. coli* operons involved in arabinose utilization are inducible by arabinose—araBAD, araC, araE, and araFGH—but the terms 'arabinose promoter' and 'ara promoter' are typically used to designate the araBAD promoter. Several additional terms have been used to indicate the *E. coli* araBAD promoter, such as $P_{ara}$, $P_{araB}$, $P_{araBAD}$, and $P_{BAD}$. The use herein of 'ara promoter' or any of the alternative terms given above, means the *E. coli* araBAD promoter. As can be seen from the use of another term, 'araC-araBAD promoter', the araBAD promoter is considered to be part of a bidirectional promoter, with the araBAD promoter controlling expression of the araBAD operon in one direction, and the araC promoter, in close proximity to and on the opposite strand from the araBAD promoter, controlling expression of the araC coding sequence in the other direction. The AraC protein is both a positive and a negative transcriptional regulator of the araBAD promoter. In the absence of arabinose, the AraC protein represses transcription from $P_{BAD}$, but in the presence of arabinose, the AraC protein, which alters its conformation upon binding arabinose, becomes a positive regulatory element that allows transcription from $P_{BAD}$. The araBAD operon encodes proteins that metabolize L-arabinose by converting it, through the intermediates L-ribulose and L-ribulose-phosphate, to D-xylulose-5-phosphate. For the purpose of maximizing induction of expression from an arabinose-inducible promoter, it is useful to eliminate or reduce the function of AraA, which catalyzes the conversion of L-arabinose to L-ribulose, and optionally to eliminate or reduce the function of at least one of AraB and AraD, as well. Eliminating or reducing the ability of host cells to decrease the effective concentration of arabinose in the cell, by eliminating or reducing the cell's ability to convert arabinose to other sugars, allows more arabinose to be available for induction of the arabinose-inducible promoter. The genes encoding the transporters which move arabinose into the host cell are araE, which encodes the low-affinity L-arabinose proton symporter, and the araFGH operon, which encodes the subunits of an ABC superfamily high-affinity L-arabinose transporter. Other proteins which can transport L-arabinose into the cell are certain mutants of the LacY lactose permease: the LacY(A177C) and the LacY(A177V) proteins, having a cysteine or a valine amino acid instead of alanine at position 177, respectively (Morgan-Kiss et al., "Long-term and homogeneous regulation of the *Escherichia coli* araBAD promoter by use of a lactose transporter of relaxed specificity", Proc Natl Acad Sci USA 2002 May 28; 99(11): 7373-7377). In order to achieve homogenous induction of an arabinose-inducible promoter, it is useful to make transport of arabinose into the cell independent of regulation by arabinose. This can be accomplished by eliminating or reducing the activity of the AraFGH transporter proteins and altering the expression of araE so that it is only transcribed from a constitutive promoter. Constitutive expression of araE can be accomplished by eliminating or reducing the function of the native araE gene, and introducing into the cell an expression construct which includes a coding sequence for the AraE protein expressed from a constitutive promoter. Alternatively, in a cell lacking AraFGH function, the promoter controlling expression of the host cell's chromosomal araE gene can be changed from an arabinose-inducible promoter to a constitutive promoter. In similar manner, as additional alternatives for homogenous induction of an arabinose-inducible promoter, a host cell that lacks AraR function can have any functional AraFGH coding sequence present in the cell expressed from a constitutive promoter. As another alternative, it is possible to express both the araE gene and the araFGH operon from constitutive promoters, by replacing the native araE and araFGH promoters with constitutive promoters in the host chromosome. It is also possible to eliminate or reduce the activity of both the AraE and the AraFGH arabinose transporters, and in that situation to use a mutation in the LacY lactose permease that allows this protein to transport arabinose. Since expression of the lacY gene is not normally regulated by arabinose, use of a LacY mutant such as LacY(A177C) or LacY(A177V), will not lead to the 'all or none' induction phenomenon when the arabinose-inducible promoter is induced by the presence of arabinose. Because the LacY(A177C) protein appears to be more effective in transporting arabinose into the cell, use of polynucleotides encoding the LacY(A177C) protein is preferred to the use of polynucleotides encoding the LacY (A177V) protein.

Propionate Promoter.

The 'propionate promoter' or 'prp promoter' is the promoter for the *E. coli* prpBCDE operon, and is also called $P_{prpB}$. Like the ara promoter, the prp promoter is part of a bidirectional promoter, controlling expression of the prpBCDE operon in one direction, and with the prpR promoter controlling expression of the prpR coding sequence in the other direction. The PrpR protein is the transcriptional regulator of the prp promoter, and activates transcription from the prp promoter when the PrpR protein binds 2-methylcitrate ('2-MC'). Propionate (also called propanoate) is the ion, $CH_3CH_2COO^-$, of propionic acid (or 'propanoic acid'), and is the smallest of the 'fatty' acids having the general formula $H(CH_2)_nCOOH$ that shares certain properties of this class of molecules: producing an oily layer when salted out of water and having a soapy potassium salt. Commercially available propionate is generally sold as a monovalent cation salt of propionic acid, such as sodium propionate ($CH_3CH_2COONa$), or as a divalent cation salt, such as calcium propionate ($Ca(CH_3CH_2COO)_2$). Propionate is membrane-permeable and is metabolized to 2-MC by conversion of propionate to propionyl-CoA by PrpE (propionyl-CoA synthetase), and then conversion of propionyl-CoA to 2-MC by PrpC (2-methylcitrate synthase). The other proteins encoded by the prpBCDE operon, PrpD (2-methylcitrate dehydratase) and PrpB (2-methylisocitrate lyase), are involved in further catabolism of 2-MC into smaller products such as pyruvate and succinate. In order to maximize induction of a propionate-inducible promoter by propionate added to the cell growth medium, it is therefore desirable to have a host cell with PrpC and PrpE activity, to convert propionate into 2-MC, but also having eliminated or reduced PrpD activity, and optionally eliminated or reduced PrpB activity as well, to prevent 2-MC from being metabolized. Another operon encoding proteins involved in 2-MC biosynthesis is the scpA-argK-scpBC operon, also called the sbm-ygfDGH operon. These genes encode proteins required for the conversion of succinate to propionyl-CoA, which can then be converted to 2-MC by PrpC. Elimination or reduction of the function of these proteins would remove a parallel pathway for the production of the 2-MC inducer, and thus might reduce background levels of expression of a propionate-inducible promoter, and increase sensitivity of the propionate-inducible promoter to exogenously supplied propionate. It has been found that a deletion of sbm-ygfD-ygfG-ygfH-ygfI, introduced into *E. coli* BL21(DE3) to create strain JSB (Lee and Keasling, "A propionate-inducible expression system for enteric bacteria", Appl Environ Microbiol 2005 November; 71(11): 6856-6862), was helpful in reducing background expression in the absence of exogenously supplied inducer, but this deletion also reduced overall expression from the prp promoter in strain JSB. It should be noted, however, that the deletion sbm-ygfD-ygfG-ygfH-ygfI also apparently affects ygfI, which encodes a putative LysR-family transcriptional regulator of unknown function. The genes sbm-ygfDGH are transcribed as one operon, and ygfI is transcribed from the opposite strand. The 3' ends of the ygfH and ygfI coding sequences overlap by a few base pairs, so a deletion that takes out all of the sbm-ygfDGH operon apparently takes out ygfI coding function as well. Eliminating or reducing the function of a subset of the sbm-ygfDGH gene products, such as YgfG (also called ScpB, methylmalonyl-CoA decarboxylase), or deleting the majority of the sbm-ygfDGH (or scpA-argK-scpBC) operon while leaving enough of the 3' end of the ygfH (or scpC) gene so that the expression of ygfI is not affected, could be sufficient to reduce background expression from a propionate-inducible promoter without reducing the maximal level of induced expression.

Rhamnose Promoter.

(As used herein, 'rhamnose' means L-rhamnose.) The 'rhamnose promoter' or 'rha promoter', or $P_{rhaSR}$, is the promoter for the *E. coli* rhaSR operon. Like the ara and pip promoters, the rha promoter is part of a bidirectional promoter, controlling expression of the rhaSR operon in one direction, and with the rhaBAD promoter controlling expression of the rhaBAD operon in the other direction. The rha promoter, however, has two transcriptional regulators involved in modulating expression: RhaR and RhaS. The RhaR protein activates expression of the rhaSR operon in the presence of rhamnose, while RhaS protein activates expression of the L-rhamnose catabolic and transport operons, rhaBAD and rhaT, respectively (Wickstrum et al., "The AraC/XylS family activator RhaS negatively autoregulates rhaSR expression by preventing cyclic AMP receptor protein activation", J Bacteriol 2010 January; 192(1): 225-232). Although the RhaS protein can also activate expression of the rhaSR operon, in effect RhaS negatively autoregulates this expression by interfering with the ability of the cyclic AMP receptor protein (CRP) to coactivate expression with RhaR to a much greater level. The rhaBAD operon encodes the rhamnose catabolic proteins RhaA (L-rhamnose isomerase), which converts L-rhamnose to L-rhamnulose; RhaB (rhamnulokinase), which phosphorylates L-rhamnulose to form L-rhamnulose-1-P; and RhaD (rhamnulose-1-phosphate aldolase), which converts L-rhamnulose-1-P to L-lactaldehyde and DHAP (dihydroxyacetone phosphate). To maximize the amount of rhamnose in the cell available for induction of expression from a rhamnose-inducible promoter, it is desirable to reduce the amount of rhamnose that is broken down by catalysis, by eliminating or reducing the function of RhaA, or optionally of RhaA and at least one of RhaB and RhaD. *E. coli* cells can also synthesize L-rhamnose from alpha-D-glucose-1-P through the activities of the proteins RmlA, RmlB, RmlC, and RmlD (also called RfbA, RfbB, RfbC, and RfbD, respectively) encoded by the rmlBDACX (or rfbBDACX) operon. To reduce background expression from a rhamnose-inducible promoter, and to enhance the sensitivity of induction of the rhamnose-inducible promoter by exogenously supplied rhamnose, it could be useful to eliminate or reduce the function of one or more of the RmlA, RmlB, RmlC, and RmlD proteins. L-rhamnose is transported into the cell by RhaT, the rhamnose permease or L-rhamnose:proton symporter. As noted above, the expression of RhaT is activated by the transcriptional regulator RhaS. To make expression of RhaT independent of induction by rhamnose (which induces expression of RhaS), the host cell can be altered so that all functional RhaT coding sequences in the cell are expressed from constitutive promoters. Additionally, the coding sequences for RhaS can be deleted or inactivated, so that no functional RhaS is produced. By eliminating or reducing the function of RhaS in the cell, the level of expression from the rhaSR promoter is increased due to the absence of negative autoregulation by RhaS, and the level of expression of the rhamnose catalytic operon rhaBAD is decreased, further increasing the ability of rhamnose to induce expression from the rha promoter.

Xylose Promoter.

(As used herein, 'xylose' means D-xylose.) The xylose promoter, or 'xyl promoter', or $P_{xylA}$, means the promoter for the *E. coli* xylAB operon. The xylose promoter region is similar in organization to other inducible promoters in that the xylAB operon and the xylFGHR operon are both expressed from adjacent xylose-inducible promoters in opposite directions on the *E. coli* chromosome (Song and Park, "Organization and regulation of the D-xylose operons in *Escherichia coli* K-12: XylR acts as a transcriptional activator", J Bacteriol. 1997 November; 179(22): 7025-7032). The transcriptional regulator of both the $P_{xylA}$ and $P_{xylF}$ promoters is XylR, which activates expression of these promoters in the presence of xylose. The xylR gene is expressed either as part of the xylFGHR operon or from its own weak promoter, which is not inducible by xylose, located between the xylH and xylR protein-coding sequences. D-xylose is catabolized by XylA (D-xylose isomerase), which converts D-xylose to D-xylulose, which is then phosphorylated by XylB (xylulokinase) to form D-xylulose-5-P. To maximize the amount of xylose in the cell available for induction of expression from a xylose-inducible promoter, it is desirable to reduce the amount of xylose that is broken down by catalysis, by eliminating or reducing the function of at least XylA, or optionally of both XylA and XylB. The xylFGHR operon encodes XylF, XylG, and XylH, the subunits of an ABC superfamily high-affinity D-xylose transporter. The xylE gene, which encodes the *E. coli* low-affinity xylose-proton symporter, represents a separate operon, the expression of which is also inducible by xylose. To make expression of a xylose transporter independent of induction by xylose, the host cell can be altered so that all functional xylose transporters are expressed from constitutive promoters. For example, the xylFGHR operon could be altered so that the xylFGH coding sequences are deleted, leaving XylR as the only active protein expressed from the xylose-inducible $P_{xylF}$ promoter, and with the xylE coding sequence expressed from a constitutive promoter rather than its native promoter. As another example, the xylR coding sequence is expressed from the $P_{xylA}$ or the $P_{xylF}$ promoter in an expression construct, while either the xylFGHR operon is deleted and xylE is constitutively expressed, or alternatively an xylFGH operon (lacking the xylR coding sequence since that is present in an expression construct) is expressed from a constitutive promoter and the xylE coding sequence is deleted or altered so that it does not produce an active protein.

Lactose Promoter.

The term 'lactose promoter' refers to the lactose-inducible promoter for the lacZYA operon, a promoter which is also called lacZp1; this lactose promoter is located at ca. 365603-365568 (minus strand, with the RNA polymerase binding ('−35') site at ca. 365603-365598, the Pribnow box ('−10') at 365579-365573, and a transcription initiation site at 365567) in the genomic sequence of the *E. coli* K-12 substrain MG1655 (NCBI Reference Sequence NC_000913.2, 11 Jan. 2012). In some embodiments, expression systems of the invention can comprise a lactose-inducible promoter such as the lacZYA promoter. In other embodiments, the expression systems of the invention comprise one or more inducible promoters that are not lactose-inducible promoters.

Alkaline Phosphatase Promoter.

The terms 'alkaline phosphatase promoter' and 'phoA promoter' refer to the promoter for the phoApsiF operon, a promoter which is induced under conditions of phosphate starvation. The phoA promoter region is located at ca. 401647-401746 (plus strand, with the Pribnow box ('−10') at 401695-401701 (Kikuchi et al., "The nucleotide sequence of the promoter and the amino-terminal region of alkaline phosphatase structural gene (phoA) of *Escherichia coli*", Nucleic Acids Res 1981 Nov. 11; 9(21): 5671-5678)) in the genomic sequence of the *E. coli* K-12 substrain MG1655 (NCBI Reference Sequence NC_000913.3, 16 Dec. 2014). The transcriptional activator for the phoA promoter is PhoB, a transcriptional regulator that, along with the sensor protein PhoR, forms a two-component signal transduction system in *E. coli*. PhoB and PhoR are transcribed from the phoBR operon, located at ca. 417050-419300 (plus strand, with the PhoB coding sequence at 417,142-417,831 and the PhoR coding sequence at 417,889-419,184) in the genomic sequence of the *E. coli* K-12 substrain MG1655 (NCBI Reference Sequence NC_000913.3, 16 Dec. 2014). The phoA promoter differs from the inducible promoters described above in that it is induced by the lack of a substance—intracellular phosphate—rather than by the addition of an inducer. For this reason the phoA promoter is generally used to direct transcription of gene products that are to be produced at a stage when the host cells are depleted for phosphate, such as the later stages of fermentation. In some embodiments, expression systems of the invention can comprise a phoA promoter. In other embodiments, the expression systems of the invention comprise one or more inducible promoters that are not phoA promoters.

III. Host Cells.

Expression constructs encoding gene products of interest are expressed in host cells to produce the gene products of interest. Host cells can be any cell capable of comprising such expression constructs and expressing them. Particularly suitable host cells are capable of growth at high cell density in fermentation culture, and can produce gene products in oxidizing host cell cytoplasm through highly controlled inducible gene expression. Host cells with these qualities are produced by combining some or all of the following characteristics. (1) The host cells are genetically modified to have an oxidizing cytoplasm, through increasing the expression or function of oxidizing polypeptides in the cytoplasm, and/or by decreasing the expression or function of reducing polypeptides in the cytoplasm. Specific examples of such genetic alterations are provided herein. Optionally, host cells can also be genetically modified to express chaperones and/or cofactors that assist in the production of the desired gene product(s), and/or to glycosylate polypeptide gene products. (2) The host cells comprise one or more expression constructs designed for the expression of one or more gene products of interest; in certain embodiments, at least one expression construct comprises an inducible promoter and a polynucleotide encoding a gene product to be expressed from the inducible promoter. (3) The host cells contain additional genetic modifications designed to improve certain aspects of gene product expression from the expression construct(s). In particular embodiments, the host cells (A) have an alteration of gene function of at least one gene encoding a transporter protein for an inducer of at least one inducible promoter, and as another example, wherein the gene encoding the transporter protein is selected from the group consisting of araE, araF, araG, araH, rhaT, xylF, xylG, and xylH, or particularly is araE, or wherein the alteration of gene function more particularly is expression of araE from a constitutive promoter; and/or (B) have a reduced level of gene function of at least one gene encoding a protein that metabolizes an inducer of at least one inducible promoter, and as further examples, wherein the gene encoding a protein that metabolizes an inducer of at least one said inducible promoter is selected from the group consisting of araA, araB, araD, prpB, prpD, rhaA, rhaB, rhaD, xylA, and xylB; and/or (C) have a reduced level of gene function of at least one gene encoding a protein involved in biosynthesis of an inducer of at least one inducible promoter, which gene in further embodiments is selected from the group consisting of scpA/sbm, argK/ygfD, scpB/ygfG, scpC/ygfH, rmlA, rmlB, rmlC, and rmlD.

Examples of host cells are provided that allow for the efficient and cost-effective production of gene products, including multimeric products. Host cells can include, in addition to isolated cells in culture, cells that are part of a multicellular organism, or cells grown within a different organism or system of organisms. In certain embodiments of the invention, the host cells are microbial cells such as yeasts (*Saccharomyces, Schizosaccharomyces*, etc.) or bacterial cells, or are gram-positive bacteria or grain-negative bacteria, or are *E. coli*, or are an *E. coli* B strain, or are *E. coli* (B strain) EB0001 cells (also called *E. coli* ASE(DGH) cells), or are *E. coli* (B strain) EB0002 cells. In growth experiments with *E. coli* host cells having oxidizing cytoplasm, specifically the *E. coli* B strains SHuffle® Express (NEB Catalog No. C3028H) and SHuffle® T7 Express (NEB Catalog No. C3029H) and the *E. coli* K strain SHuffle® T7 (NEB Catalog No. C3026H), we have determined that these *E. coli* B strains with oxidizing cytoplasm are able to grow to much higher cell densities than the most closely corresponding *E. coli* K strain.

Prokaryotic Host Cells.

In some embodiments of the invention, expression constructs designed for expression of gene products are provided in host cells, such as prokaryotic host cells. Prokaryotic host cells can include archaea (such as *Haloferax volcanii, Sulfolobus solfataricus*), Gram-positive bacteria (such as *Bacillus subtilis, Bacillus licheniformis, Brevibacillus choshinensis, Lactobacillus brevis, Lactobacillus buchneri, Lactococcus lactis*, and *Streptomyces lividans*), or Gram-negative bacteria, including Alphaproteobacteria (*Agrobacterium tumefaciens, Caulobacter crescentus, Rhodobacter sphaeroides*, and *Sinorhizobium meliloti*), Betaproteobacteria (*Alcaligenes eutrophus*), and Gammaproteobacteria (*Acinetobacter calcoaceticus, Azotobacter vinelandii, Escherichia coli, Pseudomonas aeruginosa*, and *Pseudomonas putida*). Preferred host cells include Gammaproteobacteria of the family Enterobacteriaceae, such as *Enterobacter, Erwinia, Escherichia* (including *E. coli*), *Klebsiella, Pro-*

*teus*, *Salmonella* (including *Salmonella typhimurium*), *Serratia* (including *Serratia marcescans*), and *Shigella*.

Eukaryotic Host Cells.

Many additional types of host cells can be used for the expression systems of the invention, including eukaryotic cells such as yeast (*Candida shehatae, Kluyveromyces lactis, Kluyveromyces fragilis*, other *Kluyveromyces* species, *Pichia pastoris, Saccharomyces cerevisiae, Saccharomyces pastorianus* also known as *Saccharomyces carlsbergensis, Schizosaccharomyces pombe, Dekkera/Brettanomyces* species, and *Yarrowia lipolytica*); other fungi (*Aspergillus nidulans, Aspergillus niger, Neurospora crassa, Penicillium, Tolypocladium, Trichoderma reesia*); insect cell lines (*Drosophila melanogaster* Schneider 2 cells and *Spodoptera frugiperda* Sf9 cells); and mammalian cell lines including immortalized cell lines (Chinese hamster ovary (CHO) cells, HeLa cells, baby hamster kidney (BHK) cells, monkey kidney cells (COS), human embryonic kidney (HEK, 293, or HEK-293) cells, and human hepatocellular carcinoma cells (Hep G2)). The above host cells are available from the American Type Culture Collection.

Alterations to Host Cell Gene Functions.

Certain alterations can be made to the gene functions of host cells comprising inducible expression constructs, to promote efficient and homogeneous induction of the host cell population by an inducer. Preferably, the combination of expression constructs, host cell genotype, and induction conditions results in at least 75% (more preferably at least 85%, and most preferably, at least 95%) of the cells in the culture expressing gene product from each induced promoter, as measured by the method of Khlebnikov et al. "Regulatable arabinose-inducible gene expression system with consistent control in all cells of a culture", J Bacteriol 2000 December; 182(24): 7029-7034, as described in WO2014025663A1, Example 8B. For host cells other than *E. coli*, these alterations can involve the function of genes that are structurally similar to an *E. coli* gene, or genes that carry out a function within the host cell similar to that of the *E. coli* gene. Alterations to host cell gene functions include eliminating or reducing gene function by deleting the gene protein-coding sequence in its entirety, or deleting a large enough portion of the gene, inserting sequence into the gene, or otherwise altering the gene sequence so that a reduced level of functional gene product is made from that gene. Alterations to host cell gene functions also include increasing gene function by, for example, altering the native promoter to create a stronger promoter that directs a higher level of transcription of the gene, or introducing a missense mutation into the protein-coding sequence that results in a more highly active gene product. Alterations to host cell gene functions include altering gene function in any way, including for example, altering a native inducible promoter to create a promoter that is constitutively activated. In addition to alterations in gene functions for the transport and metabolism of inducers, as described herein with relation to inducible promoters, and/or an altered expression of chaperone proteins, it is also possible to alter the reduction-oxidation environment of the host cell.

Host Cell Reduction-Oxidation Environment.

In bacterial cells such as *E. coli*, proteins that need disulfide bonds are typically exported into the periplasm where disulfide bond formation and isomerization is catalyzed by the Dsb system, comprising DsbABCD and DsbG. Increased expression of the cysteine oxidase DsbA, the disulfide isomerase DsbC, or combinations of the Dsb proteins, which are all normally transported into the periplasm, has been utilized in the expression of heterologous proteins that require disulfide bonds (Makino et al., "Strain engineering for improved expression of recombinant proteins in bacteria", Microb Cell Fact 2011 May 14; 10: 32). It is also possible to express cytoplasmic forms of these Dsb proteins, such as a cytoplasmic version of DsbA and/or of DsbC ('cDsbA' or 'cDsbC'), that lacks a signal peptide and therefore is not transported into the periplasm. Cytoplasmic Dsb proteins such as cDsbA and/or cDsbC are useful for making the cytoplasm of the host cell more oxidizing and thus more conducive to the formation of disulfide bonds in heterologous proteins produced in the cytoplasm. The host cell cytoplasm can also be made less reducing and thus more oxidizing by altering the thioredoxin and the glutaredoxin/glutathione enzyme systems directly: mutant strains defective in glutathione reductase (gor) or glutathione synthetase (gshB), together with thioredoxin reductase (trxB), render the cytoplasm oxidizing. These strains are unable to reduce ribonucleotides and therefore cannot grow in the absence of exogenous reductant, such as dithiothreitol (DTT). Suppressor mutations (such as ahpC* and $ahpC^4$, Lobstein et al., "SHuffle, a novel *Escherichia coli* protein expression strain capable of correctly folding disulfide bonded proteins in its cytoplasm", Microb Cell Fact 2012 May 8; 11: 56; doi: 10.1186/1475-2859-11-56) in the gene ahpC, which encodes the peroxiredoxin AhpC, convert it to a disulfide reductase that generates reduced glutathione, allowing the channeling of electrons onto the enzyme ribonucleotide reductase and enabling the cells defective in gor and trxB, or defective in gshB and trxB, to grow in the absence of DTT. A different class of mutated forms of AhpC can allow strains, defective in the activity of gamma-glutamylcysteine synthetase (gshA) and defective in trxB, to grow in the absence of DTT; these include AhpC V164G, AhpC S71F, AhpC E173/S71F, AhpC E171Ter, and AhpC dup162-169 (Faulkner et al., "Functional plasticity of a peroxidase allows evolution of diverse disulfide-reducing pathways", Proc Natl Acad Sci USA 2008 May 6; 105(18): 6735-6740, Epub 2008 May 2). In such strains with oxidizing cytoplasm, exposed protein cysteines become readily oxidized in a process that is catalyzed by thioredoxins, in a reversal of their physiological function, resulting in the formation of disulfide bonds. Other proteins that may be helpful to reduce the oxidative stress effects in host cells of an oxidizing cytoplasm are HPI (hydroperoxidase I) catalase-peroxidase encoded by *E. coli* katG and HPII (hydroperoxidase II) catalase-peroxidase encoded by *E. coli* katE, which disproportionate peroxide into water and $O_2$ (Farr and Kogoma, "Oxidative stress responses in *Escherichia coli* and *Salmonella typhimurium*", Microbiol Rev. 1991 December; 55(4): 561-585; Review). Increasing levels of KatG and/or KatE protein in host cells through induced coexpression or through elevated levels of constitutive expression is an aspect of some embodiments of the invention.

Another alteration that can be made to host cells is to express the sulfhydryl oxidase Erv1p from the inner membrane space of yeast mitochondria in the host cell cytoplasm, which has been shown to increase the production of a variety of complex, disulfide-bonded proteins of eukaryotic origin in the cytoplasm of *E. coli*, even in the absence of mutations in gor or trxB (Nguyen et al., "Pre-expression of a sulfhydryl oxidase significantly increases the yields of eukaryotic disulfide bond containing proteins expressed in the cytoplasm of *E. coli*" Microb Cell Fact 2011 Jan. 7; 10: 1).

Host cells comprising expression constructs preferably also express cDsbA and/or cDsbC and/or Erv1p; are deficient in trxB gene function; are also deficient in the gene function of gor, gshB, and/or gshA; optionally have increased levels of katG and/or katE gene function; and optionally express an appropriate mutant form of AhpC so that the host cells can be grown in the absence of DTT.

Glycosylation of Polypeptide Gene Products.

Host cells can have alterations in their ability to glycosylate polypeptides. For example, eukaryotic host cells can have eliminated or reduced gene function in glycosyltransferase and/or oligosaccharyltransferase genes, impairing the normal eukaryotic glycosylation of polypeptides to form glycoproteins. Prokaryotic host cells such as *E. coli*, which do not normally glycosylate polypeptides, can be altered to express a set of eukaryotic or prokaryotic genes that provide a glycosylation function (DeLisa et al., "Glycosylated protein expression in prokaryotes", WO2009089154A2, 2009 Jul. 16).

Available Host Cell Strains with Altered Gene Functions.

To create preferred strains of host cells to be used in the expression systems and methods of the invention, it is useful to start with a strain that already comprises desired genetic alterations, examples of which are provided in Table 2.

TABLE 2

Host Cell Strains

| Strain: | Genotype: | Source or Reference: |
|---|---|---|
| *E. coli* Origami ™ 2 | Δ(ara-leu)7697 ΔlacX74 ΔphoA PvuII phoR araD139 ahpC galE galK rpsL F'[lac$^+$ lacI$^q$ pro] gor522::Tn10 trxB (Str$^R$, Tet$^R$) | Merck (EMD Millipore Chemicals) Catalog No. 71344 |
| *E. coli* SHuffle ® Express | fhuA2 [lon] ompT ahpC gal λatt::pNEB3-r1-cDsbC (Spec, lacI) ΔtrxB sulA11 R(mcr-73::miniTn10--Tet$^S$)2 [dcm] R(zgb-210::Tn10 --Tet$^S$) endA1 Δgor Δ(mcrC-mrr)114::IS10 | New England Biolabs Catalog No. C3028H |
| EB0001 | ΔaraBAD fhuA2 [lon] ompT ahpC$^Δ$ gal λatt::pNEB3-r1-cDsbC (Spec, lacI) ΔtrxB sulA11 R(mcr-73::miniTn10--Tet$^S$)2 [dcm) R(zgb-210::Tn10--Tet$^S$) ΔaraEp::J23104 ΔscpA-argK-scpBC endA1 rpsL-Arg43 Δgor Δ(mcrC-mrr)114::IS10 | WO2016205570A1 |
| EB0002 | ΔaraBAD fhuA2 prpD [lon] ompT ahpC$^Δ$ gal λatt::pNEB3-r1-cDsbC (Spec, lacI) ΔtrxB sulA11 R(mcr-73::miniTn10--Tet$^S$)2 [dcm] R(zgb-210::Tn10--Tet$^S$) ΔaraEp::J23104 ΔscpA-argK-scpBC endA1 rpsL-Arg43 Δgor Δ(mcrC-mrr)114::IS10 | WO2016205570A1 |

Methods of Altering Host Cell Gene Functions.

There are many methods known in the art for making alterations to host cell genes in order to eliminate, reduce, or change gene function. Methods of making targeted disruptions of genes in host cells such as *E. coli* and other prokaryotes have been described (Muyrers et al., "Rapid modification of bacterial artificial chromosomes by ET-recombination", Nucleic Acids Res 1999 Mar. 15; 27(6): 1555-1557; Datsenko and Wanner, "One-step inactivation of chromosomal genes in *Escherichia coli* K-12 using PCR products", Proc Natl Acad Sci USA 2000 Jun. 6; 97(12): 6640-6645), and kits for using similar Red/ET recombination methods are commercially available (for example, the Quick & Easy *E. coli* Gene Deletion Kit from Gene Bridges GmbH, Heidelberg, Germany). In one embodiment of the invention, the function of one or more genes of host cells is eliminated or reduced by identifying a nucleotide sequence within the coding sequence of the gene to be disrupted, such as one of the *E. coli* K-12 substrain MG1655 coding sequences incorporated herein by reference to the genomic location of the sequence, and more specifically by selecting two adjacent stretches of 50 nucleotides each within that coding sequence. The Quick & Easy *E. coli* Gene Deletion Kit is then used according to the manufacturer's instructions to insert a polynucleotide construct containing a selectable marker between the selected adjacent stretches of coding sequence, eliminating or reducing the normal function of the gene. Red/ET recombination methods can also be used to replace a promoter sequence with that of a different promoter, such as a constitutive promoter, or an artificial promoter that is predicted to promote a certain level of transcription (De Mey et al., "Promoter knock-in: a novel rational method for the fine tuning of genes", BMC Biotechnol 2010 Mar. 24; 10: 26). The function of host cell genes can also be eliminated or reduced by RNA silencing methods (Man et al., "Artificial trans-encoded small non-coding RNAs specifically silence the selected gene expression in bacteria", Nucleic Acids Res 2011 April; 39(8): e50, Epub 2011 Feb. 3). Further, known mutations that alter host cell gene function can be introduced into host cells through traditional genetic methods.

IV. Methods for Growing Host Cells

Small-Volume Growth.

Host cells used to carry out the methods of the invention can be grown in small volumes for the purpose of testing growth or induction conditions, or for the production of multiple different gene products, etc. The nature of the experiments to be performed will determine the volume that the host cells are to be grown in, such as one mL up to one liter, or between 5 mL and 500 mL, or any convenient volume. In certain embodiments, the vessel in which the host cells are grown is moved repeatedly in order to agitate the growth medium and thus provide oxygen to the host cells. Host cells are grown in a medium containing suitable nutrients and any antibiotics required to select for the retention by the host cells of expression constructs that provide antibiotic resistance. Examples of the small-volume growth of host cells are provided in Example 1. To determine the appropriate amount of inducer to be used to induce expression of inducible expression constructs present in cells, experiments such as those described in Example 10 can advantageously be performed with host cells grown in small volumes such as in multiwell plates.

Fermentation.

The fermentation processes involved in the production of recombinant proteins will use a mode of operation which falls within one of the following categories: (1) discontinuous (batch process) operation, (2) continuous operation, and (3) semi-continuous (fed-batch) operation. A batch process is characterized by inoculation of the sterile culture medium (batch medium) with microorganisms at the start of the process, cultivated for a specific reaction period. During cultivation, cell concentrations, substrate concentrations (carbon source, nutrient salts, vitamins, etc.) and product concentrations change. Good mixing ensures that there are no significant local differences in composition or temperature of the reaction mixture. The reaction is non-stationary and cells are grown until the growth-limiting substrate (generally the carbon source) has been consumed.

Continuous operation is characterized in that fresh culture medium (feed medium) is added continuously to the fermentor and spent media and cells are drawn continuously from the fermentor at the same rate. In a continuous operation, growth rate is determined by the rate of medium addition, and the growth yield is determined by the concentration of the growth limiting substrate (i.e. carbon source). All reaction variables and control parameters remain constant in time and therefore a time-constant state is established in the fermentor followed by constant productivity and output.

Semi-continuous operation can be regarded as a combination of batch and continuous operation. The fermentation is started off as a batch process and when the growth-limiting substrate has been consumed, a continuous feed medium containing glucose and minerals is added in a specified manner (fed-batch). In other words, this operation employs both a batch medium and a feed medium to achieve cell growth and efficient production of the desired protein. No cells are added or taken away during the cultivation period and therefore the fermentor operates batchwise as far as the microorganisms are concerned. While the present invention can be utilized in a variety of processes, including those mentioned above, a particular utilization is in conjunction with a fed-batch process.

In each of the above processes, cell growth and product accumulation can be monitored indirectly by taking advantage of a correlation between metabolite formation and some other variable, such as medium pH, optical density, color, and titrable acidity. For example, optical density provides an indication of the accumulation of insoluble cell particles and can be monitored on-stream using a micro-OD unit coupled to a display device or a recorder, or off-line by sampling. Optical density readings at 600 nanometers (OD600) are used as a means of determining dry cell weight.

High-cell-density fermentations are generally described as those processes which result in a yield of >30 g cell dry weight/liter ($OD_{600}$>60) at a minimum, and in certain embodiments result in a yield of >40 g cell dry weight/liter ($OD_{600}$>80). All high-cell-density fermentation processes employ a concentrated nutrient media that is gradually metered into the fermentor in a “fed-batch” process. A concentrated nutrient feed media is required for high-cell-density processes in order to minimize the dilution of the fermentor contents during feeding. A fed-batch process is required because it allows the operator to control the carbon source feeding, which is important because if the cells are exposed to concentrations of the carbon source high enough to generate high cell densities, the cells will produce so much of the inhibitory biproduct, acetate, that growth will stop (Majewski and Domach, “Simple constrained-optimization view of acetate overflow in *E. coli*”, Biotechnol Bioeng 1990 Mar. 25; 35(7): 732-738).

Acetic acid and its deprotonated ion, acetate, together represent one of the main inhibitory byproducts of bacterial growth and recombinant protein production in bioreactors. At pH 7, acetate is the most prevalent form of acetic acid. Any excess carbon energy source may be converted to acetic acid when the amount of the carbon energy source greatly exceeds the processing ability of the bacterium. Research has shown that saturation of the tricarboxylic acid cycle and/or the electron transport chain is the most likely cause of the acetic acid accumulation. The choice of growth medium may affect the level of acetic acid inhibition; cells grown in defined media may be affected by acetic acid more than those grown in complex media. Replacement of glucose with glycerol may also greatly decrease the amount of acetic acid produced. It is believed that glycerol produces less acetic acid than glucose because its rate of transport into a cell is much slower than that of glucose. However, glycerol is more expensive than glucose, and may cause the bacteria to grow more slowly. The use of reduced growth temperatures can also decrease the speed of carbon source uptake and growth rate thus decreasing the production of acetic acid. Bacteria produce acetic acid not only in the presence of an excess carbon energy source or during fast growth, but also under anaerobic conditions. When bacteria such as *E. coli* are allowed to grow too fast, they may exceed the oxygen delivery ability of the bioreactor system which may lead to anaerobic growth conditions. To prevent this from happening, a slower constant growth rate may be maintained through nutrient limitation. Other methods for reducing acetic acid accumulation include genetic modification to prevent acetic acid production, addition of acetic acid utilization genes, and selection of strains with reduced acetic acid. *E. coli* BL21(DE3) is one of the strains that has been shown to produce lower levels of acetic acid because of its ability to use acetic acid in its glyoxylate shunt pathway.

Various larger-scale fed-batch fermentors are available for production of recombinant proteins. Larger fermentors have at least 1000 liters of capacity, preferably about 1000 to 100,000 liters of capacity (i.e. working volume), leaving adequate room for headspace. These fermentors use agitator impellers or other suitable means to distribute oxygen and nutrients, especially glucose (the preferred carbon/energy source). Small-scale fermentation refers generally to fermentation in a fermentor that is no more than approximately 100 liters in volumetric capacity, and in some specific embodiments no more than approximately 10 liters.

Standard reaction conditions for the fermentation processes used to produce recombinant proteins generally involve maintenance of pH at about 5.0 to 8.0 and cultivation temperatures ranging from 20 to 50 degrees C. for microbial host cells such as *E. coli*. In one embodiment of the present invention which utilizes *E. coli* as the host system, fermentation is performed at an optimal pH of about 7.0 and an optimal cultivation temperature of about 30 degrees C.

The standard nutrient media components in these fermentation processes generally include a source of energy, carbon, nitrogen, phosphorus, magnesium, and trace amounts of iron and calcium. In addition, the media may contain growth factors (such as vitamins and amino acids), inorganic salts, and any other precursors essential to product formation. The media may contain a transportable organophosphate such as a glycerophosphate, for example an alpha-glycerophosphate and/or a beta-glycerophosphate, and as a more specific example, glycerol-2-phosphate and/or glycerol-3-phosphate. The elemental composition of the host cell being cultivated can be used to calculate the proportion of each component required to support cell growth. The component concentrations will vary depending upon whether the process is a low-cell-density or a high-cell-density process. For example, the glucose concentrations in low-cell-density batch fermentation processes range from 1 to 5 g/L, while high-cell-density batch processes use glucose concentrations ranging from 45 g/L to 75 g/L. In addition, growth media may contain modest concentrations (for example, in the range of 0.1-5 mM, or 0.25 mM, 0.5 mM, 1 mM, 1.5 mM, or 2 mM) of protective osmolytes such as betaine, dimethylsulfoniopropionate, and/or choline.

One or more inducers can be introduced into the growth medium to induce expression of the gene product(s) of interest. Induction can be initiated during the exponential growth phase, for example, such as toward the end of the exponential growth phase but before the culture reaches maximum cell density, or at earlier or later times during fermentation. When expressing the gene product(s) of interest from one or more promoters inducible by depletion of nutrients such as phosphate, induction will occur when that nutrient has been sufficiently depleted from the growth medium, without the addition of an exogenous inducer.

During exponential growth of host cells, the metabolic rate is directly proportional to availability of oxygen and a carbon/energy source; thus, reducing the levels of available oxygen or carbon/energy sources, or both, will reduce metabolic rate. Manipulation of fermentor operating parameters, such as agitation rate or back pressure, or reducing $O_2$ pressure, modulates available oxygen levels and can reduce host cell metabolic rate. Reducing concentration or delivery rate, or both, of the carbon/energy source(s) has a similar effect. Furthermore, depending on the nature of the expression system, induction of expression can lead to a decrease in host cell metabolic rate. Finally, upon reaching maximum cell density, the growth rate stops or decreases dramatically. Reduction in host cell metabolic rate can result in more controlled expression of the gene product(s) of interest, including the processes of protein folding and assembly. Host cell metabolic rate can be assessed by measuring cell growth rates, either specific growth rates or instantaneous growth rates (by measuring optical density (OD) such as OD600 and or optionally by converting OD to biomass). The approximate biomass (cell dry weight) at each assayed point is calculated: approximate biomass (g)=($OD_{600}$÷2)×volume (L). Desirable growth rates are, in certain embodiments of the invention, in the range of 0.01 to 0.7, or are in the range of 0.05 to 0.3, or are in the range of 0.1 to 0.2, or are approximately 0.15 (0.15 plus-or-minus 10%), or are 0.15.

Fermentation Equipment.

The following are examples of equipment that can be used to grow host cells; many other configurations of fermentation systems are commercially available. Host cells can be grown in a New Brunswick BioFlo/CelliGen 115 water jacketed fermentor (Eppendorf North America, Hauppauge, N.Y.), 1 L vessel size with a 2× Rushton impeller and a BioFlo/CelliGen 115 Fermentor/Bioreactor controller; temperature, pH, and dissolved oxygen (DO) are monitored. It is also possible to grow host cells in a four-fold configurable DASGIP system (Eppendorf North America, Hauppauge, N.Y.) comprising four 60- to 250-ml DASbox fermentation vessels, each with a 2× Rushton impeller, a DASbox exhaust condenser, and a DASbox feeding and monitoring module (which includes a temperature sensor, a pH/redox sensor, and a dissolved oxygen sensor). Suitable fermentation equipment also includes NLF 22 30L lab fermentors (Bioengineering, Inc., Somerville, Mass.), with 30-L capacity and 20-L maximum working volume in a stainless steel vessel; two Rushton impellers, sparged with air only; and a control system running BioSCADA software that allows for tracking and control of all relevant parameters including pH, DO, exhaust $O_2$, exhaust $CO_2$, temperature, and pressure.

V. Solubilization and Purification Methods.

The gene products expressed by the methods described herein can be purified using any of a variety of purification methods. When gene products are expressed in such a way as to produce solubilizable complexes, as described herein and as in particular embodiments described in Examples 1 and 2, a highly advantageous purification method can be used to efficiently produce properly folded and active gene product, without the need for additional refolding steps. Example 3 describes a further 'direct solubilization' method for purifying gene products expressed as solubilizable complexes, including gene products that form disulfide bonds, without the need for centrifugation following lysis to separate the soluble and insoluble fractions, and without the use of reducing agents. Methods for purifying solubilizable gene product complexes in these ways are outlined schematically in FIG. 1 and are described in more detail below.

Collecting Host Cells by Centrifugation.

Host cells comprising expression constructs are grown and the expression of the gene product of interest is induced as described further herein, resulting in the production of solubilizable complexes of the gene product of interest within the host cell. After the growth and induction periods are complete, the host cells are collected by centrifugation at 4,000×g at 4 degrees C. for 10 minutes, for example. The host cells can be frozen at this point and stored for later purification.

Lysis of Host Cells.

The resulting pellet of intact host cells is then lysed using one of several alternative methods. The pellet of host cells is resuspended in a nondenaturing lysis buffer, such as phosphate-buffered saline (PBS) or Tris-buffered saline (TBS) supplemented with from 0 mM to 300 mM NaCl or with 2.5 mM L-cysteine, pH 9.5. After resuspension in lysis buffer, the host cells can be lysed by methods including enzymatic or chemical lysis, mechanical lysis, and/or a freeze-thaw method. For enzymatic lysis, the lysis can be accomplished by adding recombinant lysozyme, benzonase, and octyl glucoside to the lysis buffer. For mechanical lysis, the resuspended host cells are passed one or more times through a microfluidizer, such as a Microfluidics model LV1 microfluidizer for volumes up to 60 ml, or a Microfluidics model M-110Y microfluidizer for volumes greater than 60 mL (Microfluidics International Corp., Westwood, Mass.), or a PandaPLUS 2000 table-top homogenizer or a GEA Niro (GEA North America, Columbia, Md.). For the freeze-thaw method, the cell suspension is frozen at −80 degrees C. and then thawed at a temperature between 25 and 37 degrees C.

Following Lysis, the Lysed Cell Mixture is Optionally Centrifuged to Pellet the Solubilizable Gene Product Complexes.

The speed and time of this centrifugation step can vary from 3,300 to 20,000×g and from 30 to 60 minutes. Using a higher speed can result in a pellet of the solubilizable gene product complex that is more difficult to resuspend. The lower the speed that is used in this centrifugation step, the longer the duration of centrifugation that is needed to complete the separation of the solubilizable gene product complex from the supernatant. It is possible to vary the salt concentration and/or the pH of the cell lysate to alter the centrifugation or other conditions needed to separate the solubilizable gene product complexes from other components in the cell lysate.

One significant advantage to collecting the gene product of interest in this way is that the majority of potentially contaminating host cell proteins and other molecules will remain in the supernatant and be removed from the pelleted solubilizable gene product complex, which is then a preparation highly enriched for the gene product of interest. Alternatively, if the supernatant remaining after pelleting of the solubillizable complexes retains sufficient gene product, the gene product in this supernatant can be solubilized as described for the direct solubilization method, and/or further purified. If analysis of the pelleted material indicates that a significant number of cells survive lysis and are being spun down with the solubilizable gene product complexes, it is possible to use a dense and/or viscous solution, such as high-concentration sucrose solution, as a "cushion" in the centrifugation procedure to separate out the intact cells from the solubilizable gene product complexes. When mechanical lysis is used, the lysed cell mixture can be passed through the microfluidizer multiple times (for example, four or five times). When the above centrifugation procedure is omitted in a direct solubilization method, the cell lysate is mixed with reagents to create the conditions for solubilization of the solubilizable gene product complexes, as described below.

The Gene Product is Released from the Solubilizable Complexes by Placement in a Solubilization Solution, Resulting in Solubilized Gene Product.

The gene product, either in a pellet resulting from centrifugation, or in the cell lysate, is solubilized as follows. Solubilization solutions preferably contain one or more chaotropic agent, such as n-butanol, ethanol, guanidinium chloride, guanidine hydrochloride, lithium perchlorate, lithium acetate, magnesium chloride, phenol, 2-propanol, sodium dodecyl sulfate, thiourea, or urea. Exemplary solubilization solutions can contain 7M to 8M urea in PBS or TRIS at pH 9.5, optionally with 2.5 mM L-cysteine, or alternatively 6M guanidine hydrochloride in PBS at pH 7.5; effective solubilization experiments have used solubilization buffers at pH values ranging from 6.5 to 11.0. Experiments for determining alternative buffer compositions to be used for solubilization are described in Example 5. The pellet may optionally be washed prior to resuspension. After addition of solubilization buffer to the pellet, it is more effective to mechanically agitate the tube containing the pellet, for example by the use of a plate vortexer for at least 10 minutes, than to resuspend the pellet by hand using a pipette tip. Reversible chemical modification of the gene product, for example citraconylation of the free lysine residues and primary amino groups, can alter the solubility of the gene product.

Optional Clarification of Solubilized Gene Product by Centrifugation.

Figure 1:
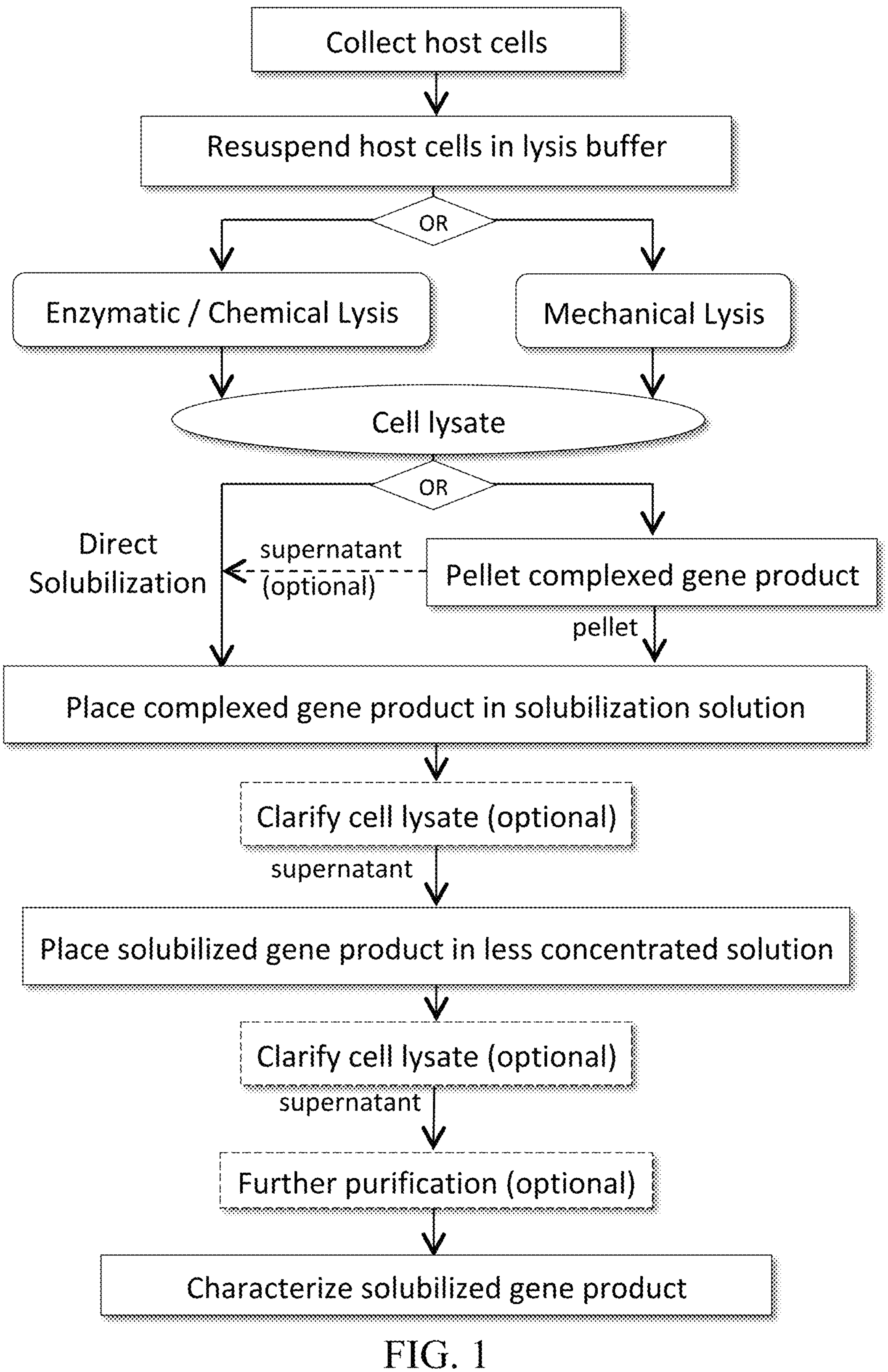
FIG. 1 is a flowchart summarizing methods for purifying solubilizable gene product complexes produced by the methods of the invention.

As shown in FIG. 1, the solution of solubilized gene product can optionally be clarified by centrifugation, such as at 7,000×g for 1 hour at 16 degrees C. The supernatant, which contains solubilized gene product, is retained after centrifugation. A clarification procedure can be performed before and/or after placing the solubilized gene product into a solution that is less concentrated than the solubilization solution, as described below.

Placing the Solubilized Gene Product into a Solution that is Less Concentrated than the Solubilization Solution.

For samples of protein gene products that are to be analyzed by peptide mapping, the solubilized gene product is typically placed in a solution having a two- to ten-fold reduced concentration of denaturant, using methods such as dialysis, dilution, or diafiltration, as the presence of 7M to 8M urea or 6M guanidine hydrochloride inhibits the cleavage efficiency of a number of proteases. For example, following solubilization in 7M to 8M urea in PBS or TRIS, pH 6.5 to 9.5, optionally with 2.5 mM L-cysteine, the samples containing gene product can be placed in 2M to 4M urea in PBS or TRIS, pH 6.5 to 9.5, optionally with 2.5 mM L-cysteine, and incubated for a period of 10 to 120 hours, for example at 16 degrees C. with shaking.

Optional Formation of Solution with a Higher Concentration of Gene Product.

For purposes such as storage, further purification, or characterization, the solution of solubilized gene product can be reconcentrated to result in a solution with a higher concentration of gene product. This can be accomplished by running the solution over a chromatography column and eluting into the desired buffer, as described below, or by spin desalting or diafiltration as described below, or by other known methods. Another alternative is the use of a precipitation method such as ammonium sulfate precipitation to precipitate the gene product; the gene product can optionally be washed before resuspension of the pellet in the desired buffer at the desired concentration.

Gene Products with Cleavage Sequences can Optionally be Cleaved by Chemical or Enzymatic Treatment.

Gene products that comprise, for example, sequences that are cleaved by enzymes such as trypsin, and/or sequences such as the 'DP' (Asp-Pro) chemical cleavage sequence described above and in Example 2, can be cleaved by the appropriate enzymatic or chemical treatment prior to use or further purification.

The Solubilized Gene Product can Optionally be Additionally Purified.

For example, gene products that include a 6×His tag can be purified by immobilized metal affinity chromatography (IMAC), such as the use of a nickel-nitrilotriacetic acid (Ni-NTA) column to specifically retain the 6×His-tagged gene product of interest while other molecules flow through. IMAC exploits interactions between histidine residues and divalent metal ions, most commonly Ni2+; other metal ions including Cu2+, Co2+, Fe2+, and Zn2+ have also been shown to have affinity for His residues. The metal ions are typically immobilized on the matrix via various metal-chelator systems, including iminodiacetic acid (IDA) and the more commonly used nitrilotriacetic acid (NTA). A wide variety of matrices are commercially available such as nickel-nitrilotriacetic acid (Ni-NTA), Ni Sepharose, and copper-carboxylmethylaspartate (CO-CMA). The column can be equilibrated with a buffer such as 50 mM Tris, 3 M urea, 0.5 M NaCl, 25 mM imidazole, pH 8.0. After binding of the 6×HIs-tagged gene product, a wash step with a buffer containing a low concentration of imidazole (0 mM, or 10 to 50 mM), or a buffer with a pH higher or lower than that of the binding buffer, can be included to remove nonspecific proteins that are weakly bound to the column during sample loading. For example, a wash buffer of 50 mM Tris, 100 mM NaCl, pH 10 can be used. The 6×His-tagged gene product can be eluted from the matrix using a buffer containing imidazole at a concentration of at least 100 mM imidazole, or 250 to 500 mM imidazole, or 500 mM imidazole. It is also possible to elute the gene products of interest by lowering the buffer pH, and/or by including chelating agents such as EDTA (at a concentration of 50 to 200 mM, or 100 mM) in the elution buffer. For example, an elution buffer of 50 mM Tris, 100 mM NaCl, 100 mM imidazole, pH 10 can be used. Purification methods for gene products that include a polyhistidine tag are further described in Bornhorst and Falke, "Purification of proteins using polyhistidine affinity tags", Methods Enzymol 2000; 326: 245-254, which is incorporated by reference herein. In the purification by IMAC of 6×His-tagged CPBpro proinsulin proteins from solubilizable complexes, using either Ni-NTA Superflow (QIAgen, Germantown, Md.) or HisTrap HP Ni Sepharose columns (GE Healthcare, Pittsburgh, Pa.), this method allowed for purification of the proinsulin gene product to greater than 90% purity.

For samples lacking a 6×His tag, or for procedures where use of such a tag is not necessary, cation or anion exchange chromatography, such as the use of DEAE resins, and/or reversed-phase or high-performance liquid chromatography (RPLC or HPLC), can be employed to further separate the gene product of interest from other contaminants or from the unwanted product(s) of chemical or enzymatic treatment.

Chemical or enzymatic procedures can optionally be performed on gene products that are retained by a solid substrate such as a column: for example, trypsin cleavage of proinsulin gene products for preparative or analytical purposes, also called transversion of proinsulin to mature insulin, as described below in Example 3C.

Chromatography procedures such as IMAC can also be used to elute the solubilized complexes into buffers other than those used to solubilize the complexes, for example, into 250 mM up to 500 mM imidazole in PBS pH 7.5, optionally followed by spin desalting to exchange the elution buffer for a more preferred buffer, as described in Example 2D. Methods for removing undesirable buffer components such as salts include dialysis, diafiltration (using, for example, centrifugal concentrators or tangential flow filtration), and gel filtration using, for example, polyacrylamide beads (Bio-Rad, Hercules, Calif.), Sephadex resin (GE Healthcare, Pittsburgh, Pa.), and/or other chromatography resins such as size-exclusion resins (Zeba™ Spin Desalting Columns, ThermoFisher Scientific Inc., Waltham, Mass.).

The Solubilized Gene Product can be Chemically and/or Structurally Characterized.

For protein gene products containing disulfide bonds, the proper folding of the protein produced by the methods of the invention can be inferred from the presence of correctly formed disulfide bonds. The identification and characterization of disulfide bonds can be achieved using peptide mapping methods in which chemical or enzymatic treatment of the protein is used to produce peptide fragments. Separation and identification of these fragments is accomplished by liquid chromatography-mass spectrometry (LC-MS) analysis; peptide mapping and LC-MS methods are described further in Example 8 below. Peptide mapping and LC-MS analysis can also identify differences in protein primary structure such as point mutations and post-translational modifications (PTMs).

The number and presence of oxidized disulfide bonds can be verified for intact protein samples. Protein gene products can be treated with a reducing agent, such as dithiothreitol (DTT), and/or a sulfhydryl-reactive reagent, such as iodoacetamide (IAA). LC-MS analysis of reduced and/or alkylated samples will result in a mass increase of 2 Da per disulfide bond reduction and a mass increase of 57 Da per alkylation of each free thiol. The protein gene product can be characterized not only on the formation of the correct number of disulfides, but also on the correct bridging arrangement or "disulfide structure." This procedure consists of proteolytic cleavage, separation of the resulting peptides by high-performance liquid chromatography (HPLC), and mass spectrometry (MS) analysis of the peptides represented by HPLC peaks. To generate proteolytic peptide products, the protein gene product can be fragmented via chemical agents, such as cyanogen bromide, and/or enzymatic agents, such as trypsin, pepsin, lysyl endopeptidase (Lys-C), glutamyl endopeptidase (Glu-C), and peptidyl-Asp metallo-endopeptidase (Asp-N). For the protein gene product proinsulin, a sequential proteolytic cleavage reaction can be performed using Glu-C and trypsin, where the order of protease addition can be interchanged (i.e. Glu-C then trypsin, or trypsin then Glu-C). The protease digestion reaction can be carried out at a temperature range of 25 to 37 degrees C. for 4 to 16 hours, with a substrate to enzyme ratio ranging from 12 to 200 micrograms of proinsulin per microgram of protease. Proteolytic cleavage efficiency and specificity can be improved through the addition of commercially available surfactants, such as ProteaseMax™ (Promega, Madison, Wis.) and RapiGest SF (Waters, Milford, Mass.), and/or low concentrations of organic solvents, such as 10-20% acetonitrile.

As described further in Example 2C and as shown in FIG. 5, LC-MS analysis demonstrated that approximately 93% of the solubilized protein gene product had properly formed disulfide bonds, without a further refolding or purification step following solubilization. Other methods that can be used for characterization of solubilized gene product include gel electrophoresis, activity assays, and high-performance liquid chromatography (HPLC) separation via analytical reversed phase or size exclusion chromatography (SEC).

Example 1

Use of CPBpro Variant Propeptides in the Production of Lispro Proinsulin

A. Preparation of Expression Constructs for CPBpro_lispro Proinsulin

In these experiments, certain CPBpro variants were used as propeptides in the small-scale expression of lispro proinsulin polypeptides. Expression constructs comprising polynucleotides encoding the CPBpro proinsulin polypeptides shown in Table 3 and optimized for expression in *E. coli* were synthesized by ATUM (Newark, Calif.). The first column of Table 3 provides the protein number (PN) and SEQ ID NO for each complete CPBpro proinsulin polypeptide amino acid sequence. The polynucleotides encoding each of the CPBpro proinsulin polypeptides, presented from the RBS sequence through the termination codon, have SEQ ID NOs 44, 46, 48, 50, 52, and 54, respectively. The second through fifth columns of Table 3 indicate the amino acid sequences of each portion of each CPBpro proinsulin polypeptide: the N-terminal CPBpro propeptide sequence, and then following in N-to-C order, the lispro insulin B chain (as shown in Table 1), the C-peptide, and the lispro insulin A chain (as shown in Table 1).

TABLE 3

CPBpro lispro proinsulin polypeptides

| PN, SEQ ID NO: | CPBpro variant residues | Insulin B chain | C-peptide | Insulin A chain |
|---|---|---|---|---|
| PN2.5; SEQ ID NO: 43 | MHHHHHHEVFVENDISLHELASTQIDFWPDIEVDFRVKAEDEVR (SEQ ID NO: 27) | SEQ ID NO: 3 | RRYPGDVKR (SEQ ID NO: 11) | SEQ ID NO: 1 |
| PN2.6; SEQ ID NO: 45 | MHHSGEHEVFVENDISLHELASTQIDFWPDIEVDFRVKAEDVEDFELDRVR (SEQ ID NO: 28) | SEQ ID NO: 3 | RRYPGDVKR (SEQ ID NO: 11) | SEQ ID NO: 1 |

TABLE 3-continued

| CPBpro lispro proinsulin polypeptides | | | | |
|---|---|---|---|---|
| PN, SEQ ID NO: | CPBpro variant residues | Insulin B chain | C-peptide | Insulin A chain |
| PN2.7; SEQ ID NO: 47 | MHHHHHHEVFVENDISLHELASTQIDFWPDIEVD FRVKAEDVEDFELDRVR (SEQ ID NO: 29) | SEQ ID NO: 3 | RRYPGDVKR (SEQ ID NO: 11) | SEQ ID NO: 1 |
| PN2.8; SEQ ID NO: 49 | MHHSGEHEVFVENDISLHELASTQIDFWPDIEVD FRVKAEDVEDFELQDSRVR (SEQ ID NO: 30) | SEQ ID NO: 3 | RRYPGDVKR (SEQ ID NO: 11) | SEQ ID NO: 1 |
| PN2.9; SEQ ID NO: 51 | MHHHHHHEVFVENDISLHELASTQIDFWPDIEVD FRVKAEDVEDFELQDSRVR (SEQ ID NO: 31) | SEQ ID NO: 3 | RRYPGDVKR (SEQ ID NO: 11) | SEQ ID NO: 1 |
| PN2.10; SEQ ID NO: 53 | MHHSGEHEKVFRVENDISLHELASTQIDFWKPDI HVDFRVKAEDLVEDFLEQELQRVR (SEQ ID NO: 32) | SEQ ID NO: 3 | RRYPGDVKR (SEQ ID NO: 11) | SEQ ID NO: 1 |

The polynucleotides encoding each of the CPBpro proinsulin polypeptides were located downstream of the araBAD promoter in the pSOL expression vector (SEQ ID NO:42). These expression constructs each also contained the coding sequence for protein disulfide isomerase (PDI, SEQ ID NO:41) downstream of the prpBCDE promoter within the pSOL expression vector.

B. Transformation of Host Cells and Expression of CPBpro_lispro Proinsulin

The pSOL:CPBpro-lispro/PDI expression constructs were transformed into EB0001 cells as follows; the genotype of EB0001 cells is shown in Table 2. Chemically competent (CaCl-treated) EB0001 cells were thawed on ice for 10 minutes. DNA (1 microliter from each expression construct DNA stock) was added to a cold, sterile eppendorf tube. EB0001 cells (100 microliters) were added to each tube of DNA and the mixture was incubated on ice for 30 minutes. The tubes were heat-shocked at 42 degrees C. for 20 seconds and allowed to rest on ice for 5 minutes. The transformed cells recovered in 900 microliters SOC outgrowth medium (New England Biolabs catalog number B9020S) at 37 degrees C. for one hour with 275 RPM shaking. After the recovery period, the cells were pelleted at 3.8 k×g for 2 minutes and resuspended in about a 100-microliter volume of recovery medium remaining from the supernatant, then plated onto agar plates containing 50 micrograms/mL kanamycin. The transformed plated cells were grown for 18 hours at 37 degrees C. For each transformation, three colonies were picked from the plate and cultured in LB medium with 50 micrograms/mL kanamycin at 30 degrees C., with shaking at 275 RPM overnight until reaching stationary phase (OD600>2.0). Glycerol stocks were made by adding 750 microliters of the overnight culture to 750 microliters 40% glycerol. Glycerol stocks were stored at −80 degrees C.

Host cell cultures for expression of CPBpro_lispro proinsulin were started by stabbing glycerol stocks and inoculating 0.1 L of LB medium containing 50 micrograms/mL kanamycin in 0.5-L non-baffled flasks. The cells were grown overnight at 30 degrees C. with shaking at 275 RPM until the OD600 reached 2. The host cell cultures were diluted to an OD600 of 0.2 in LB medium containing 50 micrograms/mL kanamycin, and grown in a total volume of 0.1 L in 0.5-L baffled flasks at 30 degrees C. with shaking at 275 RPM until the OD600 reached 0.6-0.8. At this time, the appropriate volume was pelleted (3800×g, 10 minutes) so that resuspension in M9 minimal medium containing 50 micrograms/mL kanamycin gave an OD600 of 0.7-0.75.

M9 Minimal Medium.

In a volume of 1.2 L, autoclave:

15.36 g sodium phosphate, dibasic, heptahydrate 3.6 g potassium phosphate, monobasic 0.6 g sodium chloride 1.2 g ammonium chloride 2.4 g casamino acids Adjust pH to 7.2 with KOH, autoclave at 121 degrees C. for 45 minutes, and allow to cool to room temperature; this creates an incomplete M9 minimal medium. To complete the medium: for each 10 mL incomplete medium, add the following volumes of filter-sterilized salts: 20 microliters 1M MgSO4; 1 microliter 1M CaCl2; 1 microliter 5 mg/mL FeSO4.

Cultures were transferred into 24-well deep-well plates. A 3-mL sample of host cell culture was added to each well, for each of the following induction conditions: 6 wells for each expression construct with 15 micromolar arabinose, and 6 wells for each construct with 45 micromolar arabinose. The host cells were induced at 27 or 30 degrees C. for 6 hours with 275 RPM shaking. The optical density of the host cells was measured after the induction period; the OD600 was between 1.0 and 1.2 in all the wells. Replicate samples (3×1 mL, 2×5 mL pellets) for each induction condition for each expression construct were collected by centrifugation at 3800×g for 7 minutes at room temperature.

The success of induction of the PN2.5, PN2.7, and PN2.9 expression constructs was confirmed using SDS-PAGE with coomassie blue staining. A 5-mL pellet for each induction condition for each expression construct was thawed on ice for 10 minutes. The host cells were lysed at a 6-fold concentration over culture concentration at harvest in GLB-OG lysis buffer, pH 7.4 (50 mM Tris pH 7.4, 200 mM NaCl, with 1% octylglucoside, 1× protease inhibitors; 2 U benzonase (EMD #70746) per mL culture, and 2.25 kU rLysozyme (EMD #71110) per mL culture). Lysis proceeded by incubating on ice for 10 minutes. After lysis, samples were split into two pools, one of which received total lysate prep, the other received soluble lysate prep. For the total lysate prep, after lysis 8M urea in 50 mM Tris pH 7.4, 200 mM NaCl was added to each sample at a 1:1 ratio and incubated at room temperature for 20 minutes prior to preparing to run the samples on a gel. For the soluble lysate prep, the samples were centrifuged at 20 k×g for 30 minutes at 4 degrees C., the supernatant (soluble fraction) was removed and added to 8M urea in 50 mM Tris pH 7.4, 200 mM NaCl at a 1:1 ratio and incubated at room temperature for 20 minutes prior to preparing to run the samples on a gel. Polyacrylamide gel electrophoresis (PAGE) was performed on the samples on a reducing 12% Bis-Tris gel in SDS-MES buffer, and the gel was stained with a coomassie blue stain. In the lanes with the total lysate prep, substantial bands of the expected size were seen for the PN2.5 (SEQ ID NO:43), PN2.7 (SEQ ID NO:47), and PN2.9 (SEQ ID NO:51) samples only: the CPBpro polypeptides in these samples all have a 6×His sequence immediately following the N-terminal methionine residue. However, no bands for PN2.5, PN2.7, and PN2.9 were observed in the soluble lysate prep, indicating that the substantial amounts of protein produced from the corresponding expression constructs was produced in an insoluble (and solubilizable) form. No expression was observed in any preparation for the PN2.6, PN2.8, and PN2.10 expression constructs, nor was there expression detected from the PN2.6 expression construct in follow-up experiments. While the cause of the absence of expression from the expression constructs encoding PN2.6, PN2.8, and PN2.10 has not been determined, these expression constructs share a common nucleotide sequence around the translation initiation site that differs from that in the expression constructs encoding PN2.5, PN2.7, and PN2.9, and it is possible that the message transcribed from the PN2.6, PN2.8, and PN2.10 expression constructs is not translated efficiently.

C. Solubilization and Characterization of CPBpro_lispro Proinsulin

Solubilization by 2M-6M Urea.

To determine conditions for solubilization of PN2.5 CPBpro_lispro proinsulin (SEQ ID NO:43), a 5-mL pellet of the host cells containing PN2.5 CPBpro_lispro proinsulin, produced in Example 1.B, was thawed on ice for 10 minutes. The host cells were lysed, at a 2-fold concentration over culture concentration at harvest, in GLB-OG lysis buffer pH 7.4 on ice for 10 minutes. The lysate was then divided into 12 samples and treated as follows; all of the following samples except the total lysate sample were centrifuged at 20 k×g at 4 degrees C. for 30 minutes:

Total lysate: no spin, no solubilization additives
No treatment: no solubilization additives
6M urea: addition of 8M urea in GLB
4M urea: addition of 5.3M urea in GLB
2M urea: addition of 2.66M urea in GLB
1M urea: addition of 1.33M urea in GLB
0.5 M urea: addition of 0.66M urea in GLB
4% Triton-X 100: addition of 5% Triton-X 100 in GLB
2% Triton-X 100: addition of 2.5% Triton-X 100 in GLB
1% Triton-X 100: addition of 1.25% Triton-X 100 in GLB
0.5% Triton-X 100: addition of 0.625% Triton-X 100 in GLB
0.25% Triton-X 100: addition of 0.3125% Triton-X 100 in GLB The amount of PN2.5 CPBpro_lispro proinsulin present in each sample was determined by automated capillary electrophoresis "Western blot" using the WES instrument (ProteinSimple, San Jose, Calif.), following the manufacturer's protocol and as generally described in Example 6. In preparation for analysis under reducing conditions, the total lysate, no treatment, and solubilized samples shown above were diluted 1:300 into 0.1×WES buffer (ProteinSimple) with DTT added (48 mM), bringing the samples to a final concentration of 0.0033×. The PN2.5 CPBpro_lispro proinsulin was detected by capillary electrophoresis on the WES instrument, using a mouse anti-lispro primary antibody and a HRP-conjugated goat anti-mouse secondary antibody, with exposures at 5, 15, 30, 60, 120, 240, and 480 seconds (only the 5-second exposure is used for quantitation). The Triton-X-only solubilization treatments were generally not successful in this experiment, solubilizing only around 10% or less of the total PN2.5 CPBpro_lispro proinsulin present in the samples, as indicated by the amount of PN2.5 CPBpro_lispro proinsulin detected in the total lysate. Solubilization with urea at a concentration of at least 2M was more successful: the amount of solubilized PN2.5 CPBpro_lispro proinsulin increased with increasing urea concentration, with 6M urea solubilizing about 70% of the PN2.5 CPBpro_lispro proinsulin present in the sample.

Characterization of the Size of Solubilizable CPBpro_Lispro Proinsulin Complexes.

Host cells containing solubilizable PN2.5 CPBpro_lispro proinsulin complexes were lysed as follows. To create a control "guanidine lysis" sample representing the total amount of protein generated by host cell lysis, a 1-mL pellet of the host cells containing PN2.5 CPBpro_lispro proinsulin, produced in Example 1.B, was thawed on ice for 10 minutes and resuspended in 500 microliters 6M guanidine HCl buffer, pH 8 (6M guanidine HCl, 100 mM NaPO4, 10 mM Tris Base, 10 mM imidazole, adjusted to pH 8 with 5M NaOH). The host cells were lysed by freezing at −80 degrees C. for one hour, and then thawing at room temperature for 30 minutes or until fully thawed. Host cells were also lysed in GLB-OG lysis buffer as described above and the lysate was centrifuged at 900×g at 4 degrees C. for 15 minutes to create a pellet fraction ('P1') and a supernatant ('S1') fraction. A portion of the S1 supernatant fraction was retained, and the remainder was centrifuged at 7000×g at 4 degrees C. for 30 minutes to create a pellet fraction ('P2') and a supernatant ('S2') fraction. A portion of the S2 supernatant fraction was retained, and the remainder was centrifuged at 20K×g at 4 degrees C. for 30 minutes to create a pellet fraction ('P3') and a supernatant ('S3') fraction. The P1 pellet was solubilized in 6M guanidine HCl buffer, pH 8. The guanidine lysis, solubilized P1, S1, S2, and S3 samples were analyzed by capillary electrophoresis on the WES instrument, under reducing conditions as described above. After the 900×g spin, the amount of PN2.5 CPBpro_lispro proinsulin detected in the S1 soluble fraction was about 42% of the "total lysis" amount detected in the guanidine lysis sample. The amount of PN2.5 CPBpro_lispro proinsulin detected from the solubilized P1 pellet was about 35% of the "total lysis" amount in the guanidine lysis sample, rather than the expected 58%, suggesting that loss of potentially recoverable PN2.5 CPBpro_lispro proinsulin occurred in some phase of the GLB-OG lysis, centrifugation, and solubilization procedure. Following the higher speed 7000×g and 20K×g spins, only a small amount (about 7%) of the PN2.5 CPBpro_lispro proinsulin was detected in the S2 and S3 soluble fractions, with the majority of the protein presumably ending up in the P2 and P3 pellets.

These results are consistent with a significant portion of the PN2.5 CPBpro_lispro proinsulin, perhaps about half of what was in the host cells, being present in complexes large enough to be spun down at 900×g, a relatively low centrifugation speed at which cell debris from lysed cells can be pelleted, but not soluble proteins (see Cube Biotech, "Screening detergents for optimal solubilization and purification of membrane proteins", 2013, retrieved from www.cube-biotech.com/files/protocols/Screening_Detergents.pdf on 2017 Mar. 29). Of the PN2.5 CPBpro_lispro proinsulin present in host cells that remained soluble during the 900×g spin, the vast majority of it was pelleted at an intermediate centrifugation speed of 7000×g, consistent with the remaining CPBpro_lispro proinsulin also being present in the host cells in the form of large solubilizable complexes.

Solubilization in 8M Urea and in 3.5M Urea/5% Triton-X.

To further evaluate solubilization conditions for preparation of PN2.5 CPBpro_lispro proinsulin (SEQ ID NO:43), EB0001 host cells comprising PN2.5 pSOL:CPBpro-lispro/PDI expression constructs were grown and induced with 15 micromolar arabinose as described in Example 1B. Following induction, 1-mL samples of the host cell culture were harvested by centrifugation at 3800×g at 4 degrees C. for 10 minutes. For lysis, host cell pellets were resuspended in GLB-OG lysis buffer pH 7.4 and lysis proceeded on ice for 15 minutes. Host cell lysate was centrifuged at 20K×g at 4 degrees C. for 15 minutes, and the resulting pellets were resuspended in either 8M urea in 1×Tris-buffered saline (TBS) pH 8.0, or 3.5M urea/5% triton-X in 1×TBS pH 8.0. Samples of the solubilized protein were prepared for PAGE by removing triton-X from the 3.5M urea/5% triton-X samples using a Pierce™ SDS PAGE Prep Kit (Thermo Fisher Scientific, Waltham, Mass.), and by preparing both a non-reduced (in LDS sample buffer, Thermo Fisher Scientific) and a reduced sample (in LDS sample buffer plus 100 mM DTT) to be analyzed by PAGE for each solubilization condition. The amount of solubilized PN2.5 CPBpro_lispro proinsulin in each sample was assessed by PAGE on a 12% Bis-Tris gel in SDS-MES buffer, and the gels were stained with a coomassie blue stain. Bands migrating as expected for the molecular weight of PN2.5 CPBpro_lispro proinsulin (12.25 kD) were clearly seen, with the samples solubilized in 8M urea producing significantly denser bands than those solubilized in 3.5M urea/5% triton-X buffer. This result indicates that under these conditions 8M urea is more effective than 3.5M urea/5% triton-X in solubilizing the proinsulin complexes.

CPBpro_lispro Proinsulin from Solubilizable Complexes has Disulfide Bonds and is Significantly Purified.

In order to determine whether the PN2.5 CPBpro_lispro proinsulin from solubilizable complexes has disulfide bonds or free thiol residues, the samples solubilized in 8M urea and prepared as described above were analyzed by PAGE on a 12% Bis-Tris gel in SDS-MES buffer, with the non-reduced and reduced pairs of samples run in adjacent lanes. The gel was stained with coomassie blue and is shown in FIG. 2. Treatment with DTT caused the reduced samples (Lanes 4 and 6) to run slightly more slowly than the corresponding non-reduced samples (Lanes 3 and 5), indicating the presence of disulfide bonds in the non-reduced PN2.5 CPBpro_lispro proinsulin. The difference in migration rates between the reduced and non-reduced CPBpro_lispro proinsulin was confirmed by analytical reversed-phase chromatography. FIG. 2 also shows that the solubilized PN2.5 CPBpro_lispro proinsulin (Lanes 3 through 6) was significantly purified as a result of removal of the soluble proteins in the total host cell lysate (Lanes 1 and 2) from the solubilizable CPBpro_lispro proinsulin pellet.

Solubilizable CPBpro_lispro Proinsulin Complexes Form Throughout Induction.

To further characterize the formation of the solubilizable CPBpro_lispro proinsulin complexes, an induction time course was performed with EB0001 host cells comprising the PN2.5 pSOL:CPBpro-lispro/PDI expression construct, which were grown and induced generally as described in Example 1B. In this experiment, induction was performed on host cell cultures in three volumes of 200 mL each in 1-L baffled flasks, with 15 micromolar arabinose as inducer, and with 1-mL samples taken at the 0-, 2-, 4-, and 6-hour timepoints after the initiation of induction. Host cells were harvested, lysis performed, and solubilizable pellets were resuspended in 8M urea in 1×Tris-buffered saline (TBS) pH 8.0 as described above, and analyzed by PAGE. Solubilizable CPBpro_lispro proinsulin complexes were present in host cells at each of the 2-, 4-, and 6-hour time points, as indicated by a band in each lane at the expected position. This result indicates that the solubilizable complexes are being formed in the host cells throughout the induction period, with sufficient CPBpro_lispro proinsulin present within the host cells to form solubilizable complexes after only two hours of induction.

Example 2

Use of CPBpro Variant Propeptides in the Production of Glargine Proinsulin

A. Host Cells for Expression of CPBpro_glargine Proinsulin

In these experiments, the CPBpro propeptide having the amino acid sequence of SEQ ID NO:27 ('His-CPB1') was used in the fermentation-scale expression of glargine proinsulin polypeptides. A polynucleotide encoding the His-CPB1 propeptide and optimized for expression in *E. coli* had previously been synthesized (see Example 1A). The sequence encoding His-CPB1 propeptide was cloned into an existing expression construct comprising a polynucleotide sequence encoding glargine proinsulin, similarly optimized for expression in *E. coli*, that had also been synthesized by ATUM (Newark, Calif.). The PN3.13 CPBpro_glargine proinsulin polypeptide (SEQ ID NO:55) has the His-CPB1 propeptide (SEQ ID NO:27) at its N-terminus, followed by the glargine insulin B chain (SEQ ID NO:7); a C-peptide corresponding to RRYPGDVKR (SEQ ID NO:11), except that the initial arginines (RR) of the C-peptide are indicated in this case as being at the end of the B-chain sequence of SEQ ID NO:7; and the glargine insulin A chain (SEQ ID NO:6). The structure of the PN3.13 CPBpro_glargine proinsulin polypeptide is shown schematically in FIG. 3, including the disulfide bonds found in insulin glargine. The polynucleotide encoding the PN3.13 CPBpro_glargine proinsulin polypeptide (SEQ ID NO:56) was inserted downstream of the araBAD promoter in the pSOL expression vector (SEQ ID NO:42). This expression construct also contained the coding sequence for Erv1p (SEQ ID NO:38), optimized for expression in *E. coli* (SEQ ID NO:57), downstream of the prpBCDE promoter within the pSOL expression vector. The pSOL:PN3.13-CPBpro-glargine/Erv1p expression construct was transformed into *E. coli* EB0001 cells, and glycerol stocks of the transformed host cells were prepared and stored at −80 degrees C., using the methods described in Example 1B.

B. Host Cell Growth and Induction of Expression of CPBpro_glargine Proinsulin

The EB0001(pSOL:PN3.13-CPBpro-glargine/Erv1p) host cells were grown in a DASGIP fermentation system (Eppendorf North America, Hauppauge, N.Y.) in one 250-ml DASbox fermentation vessel, bioreactor 1 ('BR1') (see 'Fermentation Equipment', above). The bioreactor was calibrated as follows: pH offset 0.80 pH; pH slope 104.15%; DO offset 0.01 nA; DO slope 66.72 nA.

Fermentation Media.

The 100-mL total volume of fermentation media, and the growth and induction feeds, were prepared as follows.

Fermentation medium; pre-sterilization components, concentration in g/L per 90 mL volume added to each bioreactor:

| | |
|---|---|
| Potassium phosphate (monobasic) | 14.8 |
| Potassium citrate tribasic (monohydrate) | 3.3 |
| Ammonium sulfate | 4.4 |
| Sodium chloride | 2.2 |
| Yeast extract | 11.1 |

Modified Korz trace metals (100× stock); combine components below, where final concentration is shown in g/L, and filter sterilize:

| | |
|---|---|
| $CoCl_2•6H_2O$ | 0.25 |
| $MnCl_2•4H_2O$ | 1.5 |
| $CuSO_4•5H_2O$ | 0.22 |
| $H_3BO_3$ | 0.3 |
| $Na_2MoO_4•2H_2O$ | 0.25 |
| $ZnSO_4•7H_2O$ | 1.7 |

Fermentation medium; post-sterilization components (sterile stock concentration), amount in mL added to reach total volume of ca. 100 mL in the bioreactor:

| | |
|---|---|
| Glucose (700 g/L) | 1.4 |
| EDTA (100x stock, 0.84 g/L) | 1.0 |
| Modified Korz trace metals (100x stock) | 1.0 |
| Ferrous ammonium sulfate (40 g/L) | 0.8 |
| 1:5 diluted magnesium sulfate heptahydrate (500 g/L) | 1.3 |
| Sterile Antifoam 204, 10% dissolved in 70% ethanol/30% $H_2O$ (Sigma-Aldrich, St. Louis, Missouri) | 0.3 |
| 1:10 diluted kanamycin (50 g/L) | 1.0 |
| Calcium chloride (200 g/L) | 1.0 |

Growth feed; components (sterile stock concentration), amount in mL that can be prepared for one bioreactor:

| | |
|---|---|
| Glucose (700 g/L) | 80 |
| EDTA (100x stock, 0.84 g/L) | 1.36 |
| Modified Korz trace metals (100x stock) | 1.44 |
| Ferrous ammonium sulfate (40 g/L) | 1.40 |
| Magnesium sulfate heptahydrate (500 g/L) | 4.0 |
| Kanamycin (50 g/L) | 0.08 |
| Yeast extract (250 g/L) | 2.8 |

Induction feed; components (sterile stock concentration), amount in mL that can be prepared for one bioreactor:

| | |
|---|---|
| Glycerol (700 g/L) | 80 |
| EDTA (100x stock, 0.84 g/L) | 1.36 |
| Modified Korz trace metals (100x stock) | 1.44 |
| Ferrous ammonium sulfate (40 g/L) | 1.40 |
| Magnesium sulfate heptahydrate (500 g/L) | 4.0 |
| Kanamycin (50 g/L) | 0.08 |
| Arabinose (500 g/L) | 0.97 |

10× Tremendous Broth ('10×TB'):

Add the following to 90 mL distilled $H_2O$: 12 g soytone, 24 g yeast extract. Adjust to 100 mL with distilled $H_2O$. Sterilize by autoclaving. Allow to cool to room temperature.

Fermentation Procedure.

A feeder culture of EB0001(pSOL:PN3.13-CPBpro-glargine/Erv1p) host cells was grown generally according to the methods described in Example 1B, but with overnight growth until the OD600 reached ca. 3, and with a larger second day inoculum into LB medium with 1% glucose in order to reach a final cell density of OD600 2.40 after 5.5 hours of growth. This feeder culture was used to inoculate the fermentation medium in the bioreactor: a 4.2-mL aliquot was added to the ca. 100 mL of medium so that the initial optical density reading (OD600) would be ca. 0.1.

The cells were grown under the growth stage conditions (30.0 degrees C., DO 30%, pH 7.0, growth feed containing 70% glucose at an initial feed rate of 0.6 mL/hr, for a set growth rate of 0.15/hr with a maximum feed rate of 3.2 mLs per hour) for 29 hours Immediately prior to the start of induction, 5 mL of 10× Tremendous Broth was added to the bioreactor. Induction was initiated; the fermentation conditions were set to the induction stage conditions: 30.0 degrees C., DO 30%, pH 7.0, and induction feed containing 70% glycerol at an induction feed coefficient of 2.1 mL per hour. The induction feed also contained the inducer L-arabinose, at a concentration calculated as follows from the total volume of components added to create the induction feed:

[*L*-arabinose] in induction feed: (0.97 mL×500 g/L)/ 89.25 mL=5.4 g/L

The host cells in the bioreactor were sampled at several time points during fermentation and induction; the optical densities of the growth culture at these time points, expressed in terms of elapsed fermentation time (EFT (hrs)) and elapsed induction time (EIT (hrs)) are shown below.

| EFT (hrs) | EIT (hrs) | Optical Density (OD600) |
|---|---|---|
| 0 | −29 | 0.1 |
| 28 | −1 | 133.2 |
| 29 | 0 | 130.8 |
| 38 | 9 | 147.2 |
| 41 | 12 | 148.0 |
| 44 | 15 | 154.4 |
| 47 | 18 | 150.4 |
| 50 | 21 | 150.8 |
| 53 | 24 | 148.4 |

The host cells in the 2-mL samples taken for optical density measurements at 9 hours or more after induction, and 125 microliters of 1:20-diluted host cells in PBS buffer, were harvested by centrifugation at 4300 RPM at 4 degrees C. for seven minutes and stored as dry frozen pellets at −80 degrees C.

C. Solubilization and Characterization of CPB-pro_glargine Proinsulin

To investigate whether the disulfide bonds present in solubilizable CPBpro_glargine proinsulin complexes are formed between the correct residues, solubilized CPB-pro_glargine proinsulin complexes were analyzed by liquid chromatography-mass spectrometry (LC-MS). Pellets of host cells which were grown, induced, and harvested from 1 mL of culture as described in Example 2B, were resuspended in 15 mL GLB-OG lysis buffer pH 7.4 and lysis proceeded on ice for 15 minutes. Host cell lysate was centrifuged at 20K×g at 4 degrees C. for 30 minutes, and the resulting pellets were resuspended in 5 mL 8M urea in 1× phosphate-buffered saline (PBS) pH 7.5.

The following procedures were performed in the enzymatic digestion and non-reduced disulfide mapping of CPB-pro_glargine proinsulin, and are schematically shown in FIG. 4. The starting samples contained solubilized CPB-pro_glargine proinsulin in 8M urea, PBS, pH 7.5 at a concentration of 0.63 mg/mL. To prepare the samples for enzymatic digestion, 25 microliters of 1M Tris pH 7.5, 165 microliters of deionized water, and 60 microliters of the CPBpro_glargine proinsulin sample were added to a 1.5-mL Eppendorf tube for each sample, generating a final concentration of the CPBpro_glargine proinsulin sample at 0.15 mg/mL (and a total of 37.5 micrograms of CPBpro_glargine proinsulin), and reducing the concentration of urea to ca. 1.9M. Sequencing-grade trypsin (Promega Corp., Madison, Wis.) was reconstituted at 0.1 mg/mL in 50 mM acetic acid. A 10-microliter volume (or 1 microgram) of trypsin was added to each sample tube and incubated at 37 degrees C. for four hours with shaking at 275 RPM. Pierce™ glutamyl endopeptidase ('Glu-C'), MS Grade (Thermo Fisher Scientific, Waltham, Mass.) was reconstituted in deionized water at 0.04 mg/mL and 5 microliters (or 0.2 micrograms) of Glu-C was added to each sample tube. The samples were incubated at 37 degrees C. for 16 hours with shaking at 275 RPM. A 5-microliter volume of 10% acetic acid was added to each tube to inactivate the proteases. At this point, samples can optionally be frozen at −80° C. prior to analysis. Samples can also optionally be analyzed by SDS-PAGE or reversed-phase LC to determine that digestion has occurred. Following the enzymatic digestion, the samples were centrifuged at 14K×g at 4 degrees C. for 5 minutes, and 20 microliters of the supernatant was transferred to the appropriate autosampler vial for use in the following MS analysis.

The Nano-LC MS/MS analysis was conducted on a recently calibrated Orbitrap Fusion™ Tribrid™ mass spectrometer and Dionex UltiMate™ 3000 RSLCnano System (Thermo Fisher Scientific) with a 60-minute method. An Acclaim™ Pepmap™ 100 C18 75 micrometer×25 cm×2 micrometer analytical column was used with an Acclaim™ Pepmap™ 100 C18 100 micrometer×2 cm×5 micrometer trapping column (Thermo Fisher Scientific). Buffer A consisted of 0.1% formic acid in LC-MS grade water, and buffer B consisted of 0.1% formic acid in LC-MS grade acetonitrile. A 200-ng amount of sample was injected onto the trap. A gradient was run as follows: 0-5 minutes 2% buffer B; 5-5.1 minutes 2-7.5% buffer B; 5.1-35 minutes 7.5-30% buffer B; 36-41 minutes 30-98% buffer B; and 42-60 minutes 2% buffer B. Samples were analyzed at 2400 V in the positive ion mode with an ion transfer tube temperature of 275 degrees C. using the EASY-Spray™ source (Thermo Fisher Scientific). MS1 scans were obtained from 400-1600 m/z at 120K resolution with an AGC (automatic gain control) of 400,000 and a maximum injection time of 50 ins. Targeted MS/MS was conducted at 742.8330 m/z (z=4) representing the following sequences: QCCTSICSLYQLE (SEQ ID NO:58) and FVNQHLGSHLVE (SEQ ID NO:59) with one interchain and one intrachain disulfide bond. Masses were calculated to four decimal points for calculations (eg. $H^+$=1.0073). Targeted MS/MS settings included a 3 m/z quadrupole isolation, HCD activation at 30%, and detection in the Orbitrap mass analyzer at 15K resolution from 100-2000 m/z with a maximum injection time of 250 ms and an AGC target of 50,000. Additional data-dependent or targeted MS/MS events can optionally be scheduled as desired, provided that a MS1 survey scan occurs at least every 2 seconds. The results of this liquid chromatography-mass spectrometry (LC-MS) analysis are shown in FIG. 5.

D. Further Purification and Solubility of CPBpro_glargine Proinsulin

Additional variant CPBpro_glargine proinsulins were prepared (PN3.15, PN3.16, and PN3.17), each having a propeptide portion corresponding to SEQ ID NOs 33, 34, and 35 respectively, with one or more acid-cleavable DP (Asp-Pro) sequences inserted before the arginine present at the C-terminal end of the propeptide. Modifications were made to the expression construct (SEQ ID NO:56) encoding PN3.13 CPBpro_glargine proinsulin (SEQ ID NO:55) to produce expression constructs (SEQ ID NOs 63, 65, and 67, respectively, shown from the ribosome binding site (RBS) to the termination codon, plus 18 bp of downstream nucleotide sequence) encoding PN3.15 CPBpro_glargine proinsulin (SEQ ID NO:62), PN3.16 CPBpro_glargine proinsulin (SEQ ID NO:64), and PN3.17 CPBpro_glargine proinsulin (SEQ ID NO:66), with each expression construct having the polynucleotide encoding CPBpro_glargine proinsulin located downstream of the araBAD promoter in the pSOL expression vector, and a polynucleotide (SEQ ID NO:57) encoding Erv1p (SEQ ID NO:38) downstream of the prpBCDE promoter, as described in Example 2A. These pSOL:PN3.15-CPBpro-glargine/Erv1p, pSOL:PN3.16-CPBpro-glargine/Erv1p, and pSOL:PN3.17-CPBpro-glargine/Erv1p expression constructs were transformed into *E. coli* EB0001 cells. The PN3.15, PN3.16, and PN3.17 CPBpro_glargine proinsulins were produced by fermentation essentially as described in Example 2B, with lysis of host cells followed by centrifugation at 20K×g at 4 degrees C. for 30 minutes. The resulting pellets, comprising solubilizable complexes of CPBpro_glargine proinsulin, were solubilized in 8M urea in 1× phosphate-buffered saline (PBS) pH 7.5.

A portion of the PN3.15 CPBpro_glargine proinsulin (SEQ ID NO:62) prepared from solubilizable complexes was loaded on a 5-mL Ni-NTA column, washed with 8M urea and 10 mM imidazole in 1×PBS pH 7.5, then eluted in 500 mM imidazole in 1×PBS pH 7.5. The PN3.15 CPBpro_glargine proinsulin was stable and soluble in the non-denaturing conditions of the Ni-NTA column purification and elution into 500 mM imidazole in 1×PBS at neutral pH 7.5. Following elution from the Ni-NTA column, PN3.15, PN3.16, and PN3.17 CPBpro_glargine proinsulin samples in 500 mM imidazole in 1×PBS pH 7.5 were each adjusted to pH 6 with formic acid to precipitate the purified CPBpro_glargine proinsulin 16K×g at 4 degrees C. for 10 minutes, and the pellets were resuspended in 0.1M acetic acid at pH 2 and incubated at 65 degrees C. for 12 hours to cleave each propeptide at the DP (Asp-Pro) sequence present in each of the PN3.15, PN3.16, and PN3.17 propeptides. Following incubation the samples were neutralized with 2M NH4HCO3 (ammonium bicarbonate) to a final pH between 7.0 and 8.0. Cleavage of the propeptides was observed by polyacrylamide gel electrophoresis.

Separation of the cleaved N-terminal portion of the PN3.17 propeptide from the remainder of the PN3.17 CPBpro_glargine proinsulin (SEQ ID NO:66) was achieved by cation-exchange chromatography ('CEX') using a Capto S medium (GE Healthcare, Pittsburgh, Pa.). A cleavage reaction, in which PN3.17 CPBpro_glargine proinsulin was treated with 0.1M acetic acid at pH 2 and incubated at 60 degrees C. for 24 hours with shaking at 275 RPM, was adjusted to pH 4 with 1M hydrochloric acid and loaded onto the cation-exchange column, then equilibrated with 8M urea in 20 mM NaOAc pH 6.5, and eluted with increasing salt concentrations, from 0M to 0.35M NaCl, in 8M urea 20 mM NaOAc pH 6.5. LC-MS analysis of the CEX-purified glargine proinsulin fragment determined that the mass of the fragment was as expected for a glargine proinsulin with all its double bonds intact. Trypsin digestion of the CEX-purified glargine proinsulin produced a mature glargine insulin molecule with intact disulfide bonds, as indicated by LC-MS analysis.

To further investigate the precipitation of PN3.15 CPBpro_glargine proinsulin (SEQ ID NO:62) by acidic conditions, samples of PN3.15 CPBpro_glargine proinsulin prepared by solubilization of solubilizable complexes and elution from a Ni-NTA column with 500 mM imidazole in 1×PBS pH 7.8, as described above, were adjusted to the following pH values using 10% formic acid: pH 7.5, 7.2, 7.0, 6.7, 6.5, 6.0, 5.5, and 5.0. The samples were then centrifuged at 14K×g at 4 degrees C. for 15 minutes, and the supernatants were removed and dried by centrifugal evaporation. The pellets and dried supernatants were then resuspended in 8M urea in 1×PBS pH 7.5, and analyzed by polyacrylamide gel electrophoresis under denaturing conditions. At pH values between 7.8 and 7.2, the majority of the PN3.15 CPBpro_glargine proinsulin remained soluble. At pH 7.0, approximately equal amounts of PN3.15 CPBpro_glargine proinsulin was observed in the supernatant and the pellet. As the pH was decreased, increasing portions of the PN3.15 CPBpro_glargine proinsulin were present in the pellet, until almost all was precipitated at pH 5.0. The ability to precipitate proteins by altering the pH of the protein solution is useful, for example, for resuspension of the protein in a smaller, more concentrated volume, and/or in a different buffer. This effect of pH on solubility was also observed for PN3.17 CPBpro_glargine proinsulin, and is considered likely to be a characteristic of other polypeptide gene products that form solubilizable complexes.

To obtain purified PN3.17 CPBpro_glargine proinsulin (SEQ ID NO:66) for further analysis, the PN3.17 CPBpro_glargine proinsulin was produced by fermentation essentially as described in Example 2B, with lysis of host cells followed by centrifugation at 20K×g at 4 degrees C. for 30 minutes. The pelleted material was solubilized in 8M urea in 1× phosphate-buffered saline (PBS) pH 7.5, at 10 mL of resuspension buffer per 1 g wet cell weight of harvested host cells, with vortexing and incubation at room temperature for 20 to 30 minutes, followed by a clarification spin at 4000×g at 4 degrees C. for 5 minutes. The solubilized PN3.17 CPBpro_glargine proinsulin was run over a 5-mL Ni-NTA column. Five column volumes (CV) of 8M urea in PBS pH 7.5 were used to equilibrate the column, the sample was loaded, followed by wash 1 (5CV 8M urea and 20 mM imidazole in PBS pH 7.5), wash 2 (1.25CV 20 mM imidazole in PBS pH 7.5), elution (5CV 500 mM imidazole in PBS pH 7.5), and cleaning (1.25CV 0.2N NaOH, 6CV 20% EtOH). To investigate the solubility of PN3.17 CPBpro_glargine proinsulin in various buffers, samples of the Ni-NTA-purified PN3.17 CPBpro_glargine proinsulin corresponding to 0.5 g wet cell weight of harvested host cells were run through 5-mL Zeba™ spin desalting columns with a 7K molecular weight cut-off (MWCO) (Thermo Fisher Scientific Inc., Waltham, Mass.). The buffers that the samples were spun into were: 500 mM imidazole in PBS pH 7.5, 200 mM imidazole in PBS pH 7.5, PBS pH 7.5, 50 mM EDTA in PBS pH 7.5, and 25 mM L-arginine in 10 mM K phosphate pH 7.5. A Bradford protein assay was used to measure the protein concentration of the PN3.17 CPBpro_glargine proinsulin solution as eluted in 500 mM imidazole in PBS pH 7.5, and the protein concentration of the PN3.17 CPBpro_glargine proinsulin solutions after spin desalting into the various buffers. The yield of PN3.17 CPBpro_glargine proinsulin in the experiment where the starting buffer, 500 mM imidazole in PBS pH 7.5, was replaced with the same buffer represents the efficiency of the spin desalting procedure, and was approximately 80%. The yield of the other samples, each transferred by spin desalting into a different buffer, ranged from 77% to 91% and were not significantly different from the yields expected from the spin desalting procedure itself, suggesting that there was no additional loss of PN3.17 CPBpro_glargine proinsulin from precipitation when transferred into a different buffer. The desalted PN3.17 CPBpro_glargine proinsulin samples were also analyzed by polyacrylamide gel electrophoresis under reducing and nonreducing conditions, and the shift in the electrophoretic mobility of the PN3.17 CPBpro_glargine proinsulin bands when exposed to reducing conditions indicates that the PN3.17 CPBpro_glargine proinsulin, as eluted from the Ni-NTA column and desalted, contained disulfide bonds.

Example 3

Use of Variant Propeptides and C-Peptides in the Production of Glargine Proinsulin A. Preparation of Glargine Proinsulin Additional glargine proinsulins were prepared (PN3.62, PN3.116, PN3.165, PN3.172, and PN3.185), each having a variant propeptide portion corresponding to either SEQ ID NO:36 or SEQ ID NO:37, and a variant C-peptide corresponding to one of SEQ ID NOs 12, 13, and 14 (see Table 4).

TABLE 4

Glargine proinsulin polypeptides

| PN, SEQ ID NO: | Propeptide | Insulin B chain | C-peptide | Insulin A chain |
|---|---|---|---|---|
| PN3.62; SEQ ID NO: 68 | MHHHHHHEVFVENDISLR (SEQ ID NO: 36) | SEQ ID NO: 7 | Human C-peptide variant (amino acids 3-35 of SEQ ID NO: 12) | SEQ ID NO: 6 |
| PN3.116; SEQ ID NO: 69 | MHHHHHHEVFVENDISLR (SEQ ID NO: 36) | SEQ ID NO: 7 | DDNLER C-peptide (amino acids 3-8 of SEQ ID NO: 14) | SEQ ID NO: 6 |
| PN3.165; SEQ ID NO: 70 | MHHHHHHR (SEQ ID NO: 37) | SEQ ID NO: 7 | Human C-peptide variant (amino acids 3-35 of SEQ ID NO: 12) | SEQ ID NO: 6 |
| PN3.172; SEQ ID NO: 71 | MHHHHHHEVFVENDISLR (SEQ ID NO: 36) | SEQ ID NO: 7 | Human C-peptide variant (amino acids 3-25 of SEQ ID NO: 13) | SEQ ID NO: 6 |
| PN3.185; SEQ ID NO: 72 | MHHHHHHR (SEQ ID NO: 37) | SEQ ID NO: 7 | Human C-peptide variant (amino acids 3-25 of SEQ ID NO: 13) | SEQ ID NO: 6 |

Polynucleotides encoding each of the glargine proinsulin polypeptides were inserted downstream of the araBAD promoter in the pSOL expression vector (SEQ ID NO:42). These expression constructs each also contained the coding sequence for protein disulfide isomerase (PDI, SEQ ID NO:41) downstream of the prpBCDE promoter within the pSOL expression vector.

Each of the expression vectors encoding the glargine proinsulin polypeptides were used to transform *E. coli* EB0001 host cells, to form the following:

EB0001(pSOL:PN3.62proglargine/PDI),
EB0001(pSOL:PN3.116proglargine/PDI),
EB0001(pSOL:PN3.165proglargine/PDI),
EB0001(pSOL:PN3.172proglargine/PDI), and
EB0001(pSOL:PN3.185proglargine/PDI).

Each of the five types of host cells above was grown in fermentation culture and induced for protein expression, then harvested, generally as described in Example 2B. Two factors that varied between samples during the fermentation process was whether the fermentation was carried out in a DASbox or an NLF apparatus, and whether or not MnCl2 was added to the fermentation as a component of the Korz trace metals (see Example 2B). These factors are indicated for each of the glargine proinsulin samples that were purified and analyzed, as described in Example 3B.

B. Purification of Glargine Proinsulin by Direct Solubilization

In order to prepare highly purified samples of properly folded glargine proinsulin with correctly placed disulfide bonds, for the purpose of transversion to mature glargine insulin as described in Example 3C, the host cells harvested above were subjected to a direct solubilization treatment following lysis that does not use an initial centrifugation step to separate the soluble and insoluble fraction in order to collect the glargine proinsulin in the form of solubilizable complexes.

The samples of harvested host cells that were purified are referred to as shown in the following list, noting the fermentation apparatus and whether MnCl2 was added (+) or was absent (−) during fermentation.

| | | |
|---|---|---|
| PN3.62 A | DASbox | MnCl2 added (+) |
| PN3.62 B | NLF | MnCl2 absent (−) |
| PN3.62 C | NLF | MnCl2 absent (−) |
| PN3.116 | DASbox | MnCl2 absent (−) |
| PN3.165 A | DASbox | MnCl2 absent (−) |
| PN3.165 B | NLF | MnCl2 added (+) |
| PN3.165 C | NLF | MnCl2 added (+) |
| PN3.172 | DASbox | MnCl2 absent (−) |
| PN3.185 A | DASbox | MnCl2 added (+) |
| PN3.185 B | NLF | MnCl2 added (+) |
| PN3.185 C | NLF | MnCl2 added (+) |

For lysis, the 'main sample group' included PN3.62 A, B, and C; PN3.116; PN3.165 A; PN3.172; and PN3.185 A. For the main sample group, the harvested host cells were suspended in 7M urea, 50 mM Tris pH 8 at a 10-fold dilution relative to fermentation culture volume. The additional samples (PN3.165 B and C, and PN3.185 B and C) were suspended in 7M urea, 2.5 mM L-Cys, 50 mM Tris pH 9.5 at a 2-fold dilution relative to fermentation culture volume. All samples were homogenized at 8,000 psi for a total of five passes, lysing the cells. The lysates were diluted 3.5-fold in 50 mM Tris pH 8 (main sample group), or 2.5 mM L-Cys, 50 mM Tris pH 9.5 (PN3.165 B and C, and PN3.185 B and C), so that all samples were in 2M urea solutions. All samples except PN3.165 C and PN3.185 C were incubated at 16 degrees C. with shaking at 120 RPM for 48-72 hours, or for PN3.165 C and PN3.185 C, for 24 hours.

Following the incubation, for purification using immobilized metal affinity chromatography (IMAC), the lysate samples were all clarified via centrifugation at 3300×g, and the soluble lysates were filtered through 0.45 micrometer polyethersulfone (PES) membranes and collected, with imidazole added to the lysates for a final concentration of 10 mM. The centrifugation step in the clarification can also be performed at 7000 to 20,000×g for 30-60 minutes, and the soluble lysates can also be filtered by glass fiber filtration (0.7 micrometer particle retention in liquid). Additives to the clarified lysate, to prevent nonspecific binding during IMAC, can include 10-20 mM imidazole and/or 0-300 mM NaCl.

The IMAC columns were equilibrated with 2-4 column volumes (CVs) of 7 M urea, 0.3 M NaCl, 10 mM imidazole, 25 mM Tris pH 8, then washed with 2-4 CVs of 0.1 M NaCl, 40 mM Tris pH 10. For one sample group (PN3.62 A and B, PN3.165 A, PN3.172, and PN3.185 A), each sample was loaded onto a Ni Sepharose Fast Flow column (GE Healthcare Life Sciences, Pittsburgh, Pa.). For a second sample group (PN3.62 C, PN3.116, PN3.165 B and C, and PN3.185 B and C), each sample was loaded onto a Ni HisTrap High Performance column (GE Healthcare Life Sciences, Pittsburgh, Pa.). The samples were loaded at the equivalent of 0.5-1 mL fermentation culture volume per mL resin. All samples were eluted using 2-4 CVs 0.5 M imidazole, 40 mM Tris, 0.1 M NaCl pH 10. The columns were cleaned in place with 2 CVs 0.5 M NaOH, and stripped with 7 M urea, 0.3 M NaCl, 0.5 M imidazole, and 25 mM Tris pH 8.

Following the IMAC, the samples were concentrated and desalted. For one sample group (PN3.62 A, PN3.165 A, PN3.172, and PN3.185 A), each sample was concentrated using a 3-kDa molecular weight cut-off (MWCO) Amicon® centrifugal concentrator (Sigma-Aldrich, St. Louis, Mo.), adding distilled water to return each sample to its starting volume for 2-3 exchanges using the same centrifugal concentrator. For the other sample group (PN3.62 B and C, PN3.116, PN3.165 B and C, and PN3.185 B and C), each sample was concentrated by tangential flow filtration and discontinuous diafiltration on a 3-kDa MWCO Vivaflow 50 tangential concentrator (Sartorius, Goettingen, Germany), with the volume in the feed reservoir concentrated to about one tenth the starting volume, then adding distilled water to return each sample to its starting volume, and repeating that process 2-3 times.

C. Transversion of Glargine Proinsulin to Mature Glargine Insulin

Experiments were performed to identify optimal conditions for transversion, by digestion with trypsin, of various forms of glargine proinsulin to mature glargine insulin ('B32 glargine'). Following treatment protocols, the results were analyzed by solid-phase extraction mass spectrometry (SPE-MS).

The SPE-MS parameters were as follows:

MS: LTQ

Column: Optimize C4 SPE

Vinject: 20 microliters

Buffer A: 2.5% MeCN in water with 0.1% formic acid

Buffer B (only to MS): 75% MeCN/25% water with 0.1% formic acid

Method: 0.6 minutes

Gradient: 100% A, 100% B, 100% A

The condition for each glargine proinsulin that produced optimal B32 glargine, according to the SPE-MS results, was selected and the corresponding sample was run by quadrupole time-of-flight (QTOF) liquid chromatography mass spectrometry (LCMS). An authentic standard of USP glargine was used for an external standard curve to quantitate the percentage of material that had undergone transversion. The percentage of transversion (% Transversion) equals the concentration of B32 glargine, as determined via A280 LC integration versus the USP glargine standard, divided by the starting concentration of glargine proinsulin, as determined via A280 LC integration versus an amino acid analyzed standard, multiplied by 100%. Integrations at A214 and via extracted ion chromatograms, versus the same glargine external standard curve, were in agreement with the integrations at A280.

The QTOF-LCMS parameters were as follows:

MS: 5600+

Column: CSH_C18 1.7 micron 2×150 mm

Vinject: 1 microliter

Buffer A: 0.1% formic acid in water

Buffer B: 0.1% formic acid in acetonitrile with the following gradient table:

| Time: | Flow Rate: | % A: | % B: | Curve: |
|---|---|---|---|---|
| Initial | 0.350 | 80.0 | 20.0 | Initial |
| 13.00 | 0.350 | 72.0 | 28.0 | 6 |
| 13.10 | 0.350 | 5.0 | 95.0 | 6 |
| 14.00 | 0.350 | 5.0 | 95.0 | 1 |
| 16.00 | 0.350 | 80.0 | 20.0 | 1 |

In Experiment 1, 5 microliters of each glargine proinsulin sample were mixed with 5 microliters of NiCl2 solution of varying concentration, and 5 microliters of a trypsin solution (4.5 g/L trypsin in 120 mM Tris 300 mM NaCl pH 9, 15 mM CaCl2). The combined volumes were spun at 500×g for 1 minute, then incubated at room temperature with shaking at 100 RPM for variable amounts of time, then the reaction was stopped by addition of 8M urea with 1% formic acid (pH 3-3.5).

In Experiment 2, varying concentrations of NiCl2, FeCl2, NaCl, and CaCl2 were added to the trypsin reaction mixture, and the reaction was carried out for varying amounts of time, but otherwise generally as described above.

In Experiment 3, varying concentrations of NaCl or of Tris buffer were added to the trypsin reaction mixture, which had constant amounts of 1.5 g/L trypsin, 50 mM CaCl2, and 7 micromolar NiCl2, and the reaction was carried out for varying amounts of time, but otherwise generally as described for Experiment 1.

In Experiment 4, varying concentrations of NiCl2 and reaction times were tested, in a trypsin reaction mixture than contained 1.5 g/L trypsin, 5 mM CaCl2, 120 mM Tris, 300 mM NaCl.

In Experiment 5, two trypsin reaction conditions were tested, containing 1.5 g/L trypsin, for varying lengths of reaction time. Each condition produced a comparable maximum result, as indicated in the table below.

In Experiment 6, varying concentrations of NaCl and pH were tested for varying amounts of time, in a trypsin reaction mixture that contained 1.5 g/L trypsin and 7 micromolar NiCl2.

For each experiment, the best reaction conditions for each of the glargine proinsulins of interest that were tested are indicated below, along with the percent transversion.

| Glargine Proinsulin | Experiment | Optimal Reaction Conditions | A280 % Transversion |
|---|---|---|---|
| PN3.62, sample A | 1 | 7 micromolar NiCl2; 120 minutes | 7.2 |
| PN3.62, pooled samples B and C | 2 | 0 micromolar NiCl2; 7 micromolar FeCl2; 0.15M NaCl; 2.5 mM CaCl2; 120 minutes | 31.2 |
| PN3.165, sample A | 1 | 35 micromolar NiCl2; 240 minutes | 30.2 |
| PN3.165, sample A | 3 | 50 mM Tris; 180 minutes | 16.2 |
| PN3.165, sample A | 3 | 250 mM Tris; 120 minutes | 16.2 |
| PN3.165, pooled samples B and C | 5 | 100 mM NaCl, 5 mM CaCl2, 40 mM Tris pH 8.8; 90 minutes | 41.9 |
| PN3.165, pooled samples B and C | 5 | 150 mM NaCl, 2.5 mM CaCl2, 7 micromolar NiCl2 pH 8.8; 90 minutes | 41.1 |
| PN3.172 | 1 | 7 micromolar NiCl2; 180 minutes | 24.8 |
| PN3.172 | 3 | 100 mM Tris; 240 minutes | 45.0 |
| PN3.185, sample A | 4 | 0 micromolar NiCl2; 60 minutes | 54.6 |
| PN3.185, sample A | 6 | 0 mM NaCl, 5 mM CaCl2, 33 mM Tris pH 9; 75 minutes | 65.2 |

These results demonstrate that high transversion frequencies can be obtained for the variant glargine proinsulin polypeptides of the invention, using the methods disclosed herein.

Example 4

Determination of Solubility of Expression Products; Methods of Detecting Inclusion Bodies When methods of the invention are used to express gene products in the cytoplasm of host cells, the following procedures can be used to determine the degree to which the gene products are produced in the cell in soluble form.

The most straightforward approach is to lyse cells using any effective method, such as enzymatic lysis with lysozyme, as described in more detail in Example 1, or by cell disruption with a microfluidizer. A sample of the cell lysate can be retained as a measure of the total gene product, soluble and insoluble, produced by the host cells. The lysed cells are then centrifuged at 20,000×g for 15 minutes at room temperature to separate out the insoluble fraction as a pellet; the soluble fraction (the supernatant) is collected. The amount of total gene product present in the cell lysate, minus the amount of soluble gene product recovered in the supernatant, represents the total amount of insoluble gene product present in the pellet. The methods for solubilization described herein can be used to determine what portion of the insoluble fraction in the pellet is solubilizable. Any method, such as ELISA or capillary electrophoresis Western blots, that can be used to detect the gene product, and preferably to specifically and quantifiably detect the gene product in each fraction, is employed and the amounts present in the soluble and insoluble fractions are compared. To test the effectiveness of this approach, endogenous host cell proteins, known to be soluble and present only in the host cell cytoplasm, are detected in both the soluble and insoluble fractions to determine whether the lysis and fractionation methods are trapping detectable amounts of soluble cytoplasmic products in the insoluble fraction.

It is also possible to directly assess whether cells contain inclusion bodies. Inclusion bodies can be harvested by centrifugation of lysed host cells, stained with dyes such as Congo Red, and visualized using bright-field or cross-polarized light microscopy at modest (10×) magnification (Wang et al., "Bacterial inclusion bodies contain amyloid-like structure", PLoS Biol 2008 Aug. 5; 6(8): e195; doi: 10.1371/journal.pbio.0060195). Such inclusion bodies can also be resolubilized (Singh and Panda, "Solubilization and refolding of bacterial inclusion body proteins", J Biosci Bioeng 2005 April; 99(4): 303-310; Review) and tested, using specific binding assays or other methods of protein identification, for example, to determine if they include particular gene products. Inclusion bodies can be distinguished from the solubilizable complexes described herein, in that the majority of the gene product recovered from inclusion bodies by solubilization will not be in an active or properly folded form, and will require at least one additional refolding step to obtain a majority of gene product that is active and/or properly folded.

Example 5

Determining Additional Methods for Solubilization of Solubilizable Gene Product Complexes The buffers used for solubilization of gene product complexes produced by the methods of the invention can include several different types of components, as described below. To optimize solubilization of any gene product of interest, experiments can be undertaken to identify the most effective combinations of solubilization buffer components. Initial experiments are performed to identify which combinations of buffer components can be readily prepared in the laboratory, using commercially available compounds. Once a test buffer has been prepared, it can be used in solubilization experiments with the gene product complexes of interest, and optionally with control gene product complexes that are known to be solubilizable to different extents in reference solubilization buffers. Examples of solubilization protocols for use with gene product complexes are provided herein, such as those described in Examples 1 and 2.

Components of Solubilization Buffers:

The following description of buffer components, summarized in Table 5, is intended to provide examples of the different types of components that can be used in combination in solubilization buffers, without limitation on either possible buffer components or the combinations thereof. For example, chaotropic agents include n-butanol, ethanol, guanidinium chloride, guanidine hydrochloride, lithium perchlorate, lithium acetate, magnesium chloride, phenol, 2-propanol, sodium dodecyl sulfate, thiourea, and/or urea. One or more compound of each type of buffer component can be used in combination with one or more compound of any or all other component types, in the preparation of solubilization buffers to be tested for effectiveness in solubilizing gene product complexes. The concentrations of buffer components shown in Table 5 include ranges of concentrations and also particular examples of concentrations that can be tested for effectiveness.

For preparation of a gene product of interest in a way that retains a properly folded gene product conformation, retains properly formed disulfide bonds, and/or retains protein activity, reducing agents would not be included in the solubilization buffer. However, certain analytic assays, such as capillary electrophoresis Western blots (see Example 6), are preferably performed with the solubilized gene product samples in a reduced state. For the purpose of preparing samples for such assays, reducing agents (for example, DTE (dithioerythritol), DTT (dithiothreitol), and/or TCEP (tris(2-carboxyethyl)phosphine)) can be included in the buffer at a concentration of 10 mM, for example, or up to 100 mM.

TABLE 5

Components that can be used in combination in solubilization buffers

| Component Type: | Examples: | Final Concentration(s) in Solubilization Buffer: |
|---|---|---|
| Organic solvent | acetonitrile, dimethylformamide (DMF), dimethyl sulfoxide (DMSO), methanol, trifluoroethanol | % organic solvent (organic: water, volume:volume): 0-60% 15-40%, 20% |
| Buffering agent | Tris, phosphate, citrate, acetate | 0-200 mM, 50 mM |
| Chaotropic agent | urea, guanidine | urea: 0-10M, 2-10M, 7M-8M, 7M, 8M; guanidine: 0-8M, 2-8M, 5M-6M, 6M |
| Detergent | CHAPS (3-[(3-cholamidopropyl)dimethylammonio]-1-propanesulfonate), CHAPSO (3-[(3-cholamidopropyl)dimethylammonio]-2-hydroxy-1-propanesulfonate); deoxycholate, N-lauroylsarcosine, octyl glucoside, SDS, sodium lauroyl sarcosinate ('sarkosyl') | 0-10%, 1%-2%, 1% |
| Salt | lithium acetate, NaCl | 0-10M, 1M |
| Aggregation suppressor | L-arginine | 0-2M, 1M |
| pH | pH can be adjusted with: citric acid/sodium citrate, HCl, mono- di- or tribasic PO4, NaOH, Tris-HCl/Tris base | pH 2.0-11.0, pH 6.5-8.0, pH 7.2-7.8, pH 7.5, pH 7.5-11.0, pH 8.0-10.0, pH 9.5 |

Example 6

Characterization by Capillary Electrophoresis Western Blot

Gene products can be detected and quantified as described below, using as an example soluble or solubilized protein gene products, by a capillary electrophoresis Western blot run on a WES system (ProteinSimple, San Jose, Calif.) according to the manufacturer's instructions. Soluble protein extracts are loaded into the capillary set, and the proteins are electrophoretically separated by size. The protein of interest in the samples is detected with a primary antibody that is specific for that protein, and incubation with an HRP-conjugated secondary antibody, such as a goat anti-human or anti-mouse secondary antibody, that recognizes the heavy and/or light chains of the primary antibody. Detection of the presence of the HRP-conjugated secondary antibody is accomplished by addition of the chemiluminescent substrate to the capillary and the direct capture of the light emitted during the enzyme-catalyzed reaction. Molecular weight estimates are calculated using a standard curve generated using six biotinylated proteins ranging from 12 k to 230 kDa for each run. Fluorescent standards are included in the sample loading buffer, giving each sample an internal standard that is used to align the sample with the molecular weight standard.

To determine the amount of protein present at a given molecular weight, known amounts of a standard preparation of the protein of interest are run in some of the capillaries, and detected using the same primary and secondary antibodies as for the experimental samples. Serial dilutions are prepared of the standard for the protein of interest having a known concentration, such as a commercially available protein standard, starting for example at 10 micrograms/mL and diluted down to 1.0 nanograms/mL Approximately five WES system capillaries are used to run the serial dilution. For each protein band in both the experimental and the serial dilution capillaries, a curve is generated by the WES system software representing the protein band's chemiluminescence intensity, and the area under each curve is evaluated, with a standard curve of these areas plotted for the protein bands in the serial dilution capillaries. To determine the concentration of the experimental samples, the area under each curve representing the chemiluminescence intensity of an experimental sample can be compared to the standard curve generated for the samples of known concentration.

Example 7

Determining the Yield and Recovery of Gene Products Produced Using the Solubilization and Purification Methods of the Invention The following method can be used to calculate the amount of gene product recovered at different stages of the solubilization and purification process, as compared to the total amount present in the cell lysate.

A standard sample for the gene product is required. This could be a commercially available sample of the gene product that has a known concentration, or an amino acid analyzed (AAA) completely purified sample of the gene product.

The cell lysate from a host cell culture, such as a fermentation culture, is prepared at a known level of dilution from the host cell culture. An SDS-PAGE gel, such as a 4-12% gel, is prepared and a serial-dilution set of samples of both the cell lysate and of the standard sample of the gene product are run on the SDS-PAGE gel under reducing conditions, followed by staining with SimplyBlue SafeStain (Thermo Fisher Scientific Inc., Waltham, Mass.). The use of reducing conditions is needed to allow the total amount of gene product in the cell lysate to be measured. A densitometry measurement of the gene product band on the SDS-PAGE gel is performed for each of the samples, and curves based on the densitometry data are plotted a follows.

For the standard samples of the gene product, the band density of the gene product band of each standard sample run on the gel is plotted on the y-axis, and the sample volume (in microliters) is plotted on the x-axis. For the sample volume, the volume of the standard sample solution present in the least-diluted sample (for example, 6 microliters) is plotted. For each serially diluted standard sample, its volume is plotted as the volume of the standard in the least-diluted sample (e.g. 6 microliters) divided by each dilution factor (e.g. 2). For these values, the sample volumes (in microliters) would be 6, 3, 1.5, 0.75, etc. A best-fit linear standard curve is created based on the plotted data, which can be expressed using the formula y=m(standard)x+k, where in is the slope of the standard curve and k is the y-intercept.

For determining the yield (or titer, in g/L) of the gene product present in the cell lysate, the band density of the gene product band for each cell lysate sample is plotted on the y-axis against the sample volumes on the x-axis, in the same manner as for the standard samples, described above. A best-fit linear curve for the cell lysate samples is also created, in the form y=m(experimental)x+k. To calculate the yield of the gene product in the cell lysate, the slope for the cell lysate samples is divided by the slope for the standard samples, and then multiplied by the concentration of the standard sample solution and multiplied by the degree to which the cell lysate samples were diluted relative to the host cell culture (for example, 100 for a 100-fold dilution).

To illustrate the use of this method, the following example is the determination of the total gene product yield of PN3.172 proglargine from a fermentation process. A highly purified and amino acid analyzed (AAA) standard sample of PN3.172 had been prepared, which had a concentration of 0.266 micrograms/microliter, which is equivalent to 0.266 g/L. The PN3.172 proglargine polypeptide was expressed in host cell fermentation culture and lysed generally according to the methods described in Examples 2B and 3A above. The cell lysate that was analyzed was diluted 80-fold relative to the host cell fermentation culture, so the dilution factor is 80. Samples of both the AAA PN3.172 standard and the PN3.172 cell lysate were prepared as sets of samples serially diluted by a factor of 1.25, having volumes of 6.0, 4.8, 3.8, 3.1, and 2.5 microliters, and these samples were run on a 4-12% SDS-PAGE gel under reducing conditions, followed by staining with SimplyBlue SafeStain (Thermo Fisher Scientific Inc., Waltham, Mass.). The band densitometry was performed for each of the AAA PN3.172 standard and the PN3.172 cell lysate samples, and the best-fit linear curves were plotted. For the AAA PN3.172 standard, the curve was y=93,899x−129,917, with the slope or m(standard) equal to 93,899. For the PN3.172 cell lysate, the curve was y=72,614x−228,763, with the slope or m(experimental) equal to 72,614. The calculation of the yield of PN3.172 in the cell lysate was: (m(experimental)/m(standard))×dilution factor×concentration of standard=(72,614/93,899)×80×0.266 g/L=16.5 g/L. In additional experiments, yields of proinsulin gene product in the cell lysate have ranged from 5 to 20 g/L.

When the optical density (for example, the $OD_{600}$) of the host cell growth culture is measured at the time of lysis, it is also possible to calculate the yield of a gene product as g/L/OD, by dividing the yield in g/L as calculated above by the optical density.

This method for calculating yield can also be used at later steps in the solubilization and purification process. For example, an SDS-PAGE gel can be run with standard samples and with experimental samples solubilized by one of the methods described herein, and the post-solubilization yield of the experimental samples can be determined. Also, this yield calculation method can be used to determine the yield of gene product following purification by column chromatography, such as Ni-IMAC purification, preferably using an RP-UPLC analysis of standard sample peaks and experimental sample peaks. When RP-UPLC analysis is used, the calculated area under the chromatogram peak(s) at the expected retention time(s) for the desired gene product is used in much the same way as band density in the yield calculation method described above. A serial dilution of the standard sample is made and those samples of known gene product quantity are run through the chromatography column one at a time, the areas under the gene product peaks are calculated, and a standard curve is plotted. For the experimental sample, the calculated area under the chromatogram peak(s) at the expected retention time(s) from any single run through the RP-UPLC column can be compared to the standard curve calculated from the serial dilution of the standard sample, to obtain the amount of gene product in the experimental sample.

The percentage of the gene product that is recovered between successive process steps can be determined by dividing the yield at the later process step by the yield at the earlier process step, and multiplying by 100%. Purification processes were performed on PN3.172 proglargine, in which the yield at the cell lysate stage was determined using the above method, and the PN3.172 proglargine was solubilized either by centrifuging solubilizable complexes to form a pellet, and then solubilizing PN3.172 proglargine from the pellet (as in Examples 1 and 2), or by the direct solubilization method (as in Example 3). The yields of soluble PN3.172 proglargine were determined using the above method, and the percent recovery of soluble PN3.172 proglargine was calculated for each solubilization method. The 'pelleting and solubilization' method of Examples 1 and 2 produced PN3.172 proglargine with 84.7% recovery, with the recovered material being 75.3% pure PN3.172 proglargine protein as determined by RP-UPLC analysis, using a BEH 300A 1.7 μm 2.1×150 mm C4 protein column (product number 186006549, Waters, Milford, Mass.). The 'direct solubilization' method of Example 3 produced PN3.172 proglargine with a comparable 81.4% recovery, however the recovered material was 30.4% pure PN3.172 proglargine protein as determined by RP-UPLC analysis. Subsequent purification of the PN3.172 proglargine prepared by each solubilization method, using a Ni-IMAC column and a buffer-exchange step, resulted in a 70.8% total recovery for the 'pelleting and solubilization' PN3.172 proglargine, with 98.2% purity, and a 71.0% total recovery for the 'direct solubilization' PN3.172 proglargine, with 94.7% purity. This experiment demonstrated that the 'pelleting and solubilization' method of Examples 1 and 2 recovers as much gene product as the direct solubilization method of Example 3, and results in a higher purity of material both before and after the subsequent chromatography step.

Example 8

Characterizing the Disulfide Bonds Present in Expression Products

The number and location of disulfide bonds in protein expression products can be determined by digestion of the protein with a protease, such as trypsin, under nonreducing conditions, and subjecting the resulting peptide fragments to mass spectrometry (MS) combining sequential electron transfer dissociation (ETD) and collision-induced dissociation (CID) MS steps (MS2, MS3) (Nili et al., "Defining the disulfide bonds of insulin-like growth factor-binding protein-5 by tandem mass spectrometry with electron transfer dissociation and collision-induced dissociation", J Biol Chem 2012 Jan. 6; 287(2): 1510-1519; Epub 2011 Nov. 22).

Digestion of Expressed Protein.

To prevent disulfide bond rearrangements, any free cysteine residues are first blocked by alkylation: the expressed protein is incubated protected from light with the alkylating agent iodoacetamide (5 mM) with shaking for 30 minutes at 20° C. in buffer with 4 M urea. Alternatively and preferably, NEM is used as the alkylating reagent, with trypsin proteolysis in combination with reduction/alkylation conducted under denaturing conditions (6M GuaHCl). Following alkylation, the expressed protein is separated by nonreducing SDS-PAGE using precast gels. Alternatively, the expressed protein is incubated in the gel after electrophoresis with iodoacetamide or NEM, or without as a control. Protein bands are stained, de-stained with double-deionized water, excised, and incubated twice in 500 microliters of 50 mM ammonium bicarbonate, 50% (v/v) acetonitrile while shaking for 30 minutes at 20° C. Protein samples are dehydrated in 100% acetonitrile for 2 minutes, dried by vacuum centrifugation, and rehydrated with 10 mg/ml of trypsin or chymotrypsin in buffer containing 50 mM ammonium bicarbonate and 5 mM calcium chloride for 15 minutes on ice. Excess buffer is removed and replaced with 50 microliters of the same buffer without enzyme, followed by incubation for 16 hours at 37° C. or 20° C., for trypsin and chymotrypsin, respectively, with shaking. Digestions are stopped by addition of 3 microliters of 88% formic acid, and after brief vortexing, the supernatant is removed and stored at −20° C. until analysis. Alternative protein fragmentation methods (LysC, Glu-C, or CNBr) are used if trypsinolysis provides insufficient sequence coverage (<75%). Using the reducing agent TCEP (tris(2-carboxyethyl)phosphine) under acidic conditions in the presence of NEM provides access to fragments with partly intact disulfide linkages. The disulfide-intact digest map is compared to the reduced (DTT or TCEP) digest map.

Localization of Disulfide Bonds by Mass Spectrometry.

Peptides are injected onto a 1 mm×8 mm trap column (Michrom BioResources, Inc., Auburn, Calif.) at 20 microliters/minute in a mobile phase containing 0.1% formic acid. The trap cartridge is then placed in-line with a 0.5 mm×250 mm column containing 5 mm Zorbax SB-C18 stationary phase (Agilent Technologies, Santa Clara, Calif.), and peptides separated by a 2-30% acetonitrile gradient over 90 minutes at 10 micro-liters/minute with a 1100 series capillary HPLC (Agilent Technologies); alternatively, a C18 column suitable for UPLC is used. Peptides are analyzed using a LTQ Velos linear ion trap with an ETD source (Thermo Fisher Scientific Inc., Waltham, Mass.). Electrospray ionization is performed using a Captive Spray source (Michrom Bioresources, Inc.), or preferably, an uncoated, pulled fused silica emitter (New Objective Inc., Woburn, Massachuetts) at 3.0 kV. Alternatively, analysis of medium-sized proteolytic fragments is performed using a Thermo LTQ-FT MS (7 Tesla) instrument, or a Synapt G2-Si quadrupole traveling wave ion mobility time-of-flight (ToF) mass spectrometer (Waters Corp., Milford, Mass.). Preferably, peptides are analyzed using an Orbitrap Fusion™ Tribrid™ mass spectrometer (Thermo Fisher Scientific). Disulfide-linked peptides have charge states of +4 or greater following trypsinization due to the presence of two N-termini and two basic residues (arginine or lysine) at the carboxy termini. These disulfide-linked peptides are preferentially isolated by the Orbitrap Fusion™ instrument so that the disulfide bonds can be broken using ETD fragmentation. Survey MS scans are followed by seven data-dependant scans consisting of CID and ETD MS2 scans on the most intense ion in the survey scan, followed by five MS3 CID scans on the first- to fifth-most intense ions in the ETD MS2 scan. CID scans use normalized collision energy of 35, and ETD scans use a 100 ins activation time with supplemental activation enabled. Minimum signals to initiate MS2 CID and ETD scans are 10,000, minimum signals for initiation of MS3 CID scans are 1000, and isolation widths for all MS2 and MS3 scans are 3.0 m/z. The dynamic exclusion feature of the software is enabled with a repeat count of 1, exclusion list size of 100, and exclusion duration of 30 seconds. Inclusion lists to target specific cross-linked species for collection of ETD MS2 scans are used. Separate data files for MS2 and MS3 scans are created by Bioworks 3.3 (Thermo Fisher Scientific) using ZSA charge state analysis. Matching of MS2 and MS3 scans to peptide sequences is performed by Sequest (V27, Rev 12, Thermo Fisher Scientific). The analysis is performed without enzyme specificity, a parent ion mass tolerance of 2.5, fragment mass tolerance of 1.0, and a variable mass of +16 for oxidized methionine residues. Results are then analyzed using the program Scaffold (V3_00_08, Proteome Software, Portland, Oreg.) with minimum peptide and protein probabilities of 95 and 99% being used. Software tools for data interpretation also include Proteome Discoverer™ 2.0 with the Disulfinator node (Thermo Fisher Scientific). Peptides from MS3 results are sorted by scan number, and cysteine containing peptides are identified from groups of MS3 scans produced from the five most intense ions observed in ETD MS2 scans. The identities of cysteine peptides participating in disulfide-linked species are further confirmed by manual examination of the parent ion masses observed in the survey scan and the ETD MS2 scan.

Example 9

Solubilization and Purification of Expression Products from Bacterial Cell Periplasm, from Spheroplasts, and from Whole Cells The solubilization and purification methods of the invention can be used in the production of gene products that accumulate in different compartments of the cell, such as the cytoplasm or periplasm. Host cells such as *E. coli* or *S. cerevisiae* have an outer cell membrane or cell wall, and can form spheroplasts when the outer membrane or wall is removed. Expressed proteins made in such hosts can be purified specifically from the periplasm, or from spheroplasts, or from whole cells, using the following method (Schoenfeld, "Convenient, rapid enrichment of periplasmic and spheroplasmic protein fractions using the new PeriPreps™ Periplasting Kit", Epicentre Forum 1998 5(1): 5; available at epibio.com/docs/default-source/forum-archive/forum-05-1---convenient-rapid-enrichment-of-periplasmic-and-spheroplasmic-protein-fractions-using-the-new-peripreps-periplasting-kit.pdf). This method is designed for *E. coli* and other grain negative bacteria, but the general approach can be modified for other host cells such as *S. cerevisiae*.

1. The bacterial host cell culture is grown to late log phase only, as older cell cultures in stationary phase commonly demonstrate some resistance to lysozyme treatment. If the expression of recombinant protein is excessive, cells may prematurely lyse; therefore, cell cultures are not grown in rich medium or at higher growth temperatures that might induce excessive protein synthesis. Protein expression is then induced; the cells should be in log phase or early stationary phase.

2. The cell culture is pelleted by centrifugation at a minimum of 1,000×g for 10 minutes at room temperature. Note: the cells must be fresh, not frozen. The wet weight of the cell pellet is determined in order to calculate the amount of reagents required for this protocol.

3. The cells are thoroughly resuspended in a minimum of 2 ml of PeriPreps Periplasting Buffer (200 mM Tris-HCl pH 7.5, 20% sucrose, 1 mM EDTA, and 30 U/microliter Ready-Lyse Lysozyme) for each gram of cells, either by vortex mixing or by pipetting until the cell suspension is homogeneous. Note: excessive agitation may cause premature lysing of the spheroplasts resulting in contamination of the periplasmic fraction with cytoplasmic proteins.

4. Incubate for five minutes at room temperature. Ready-Lyse Lysozyme is optimally active at room temperature. Lysis at lower temperatures (0° C.-4° C.) requires additional incubation time; at such temperatures incubation times are extended 2- to 4-fold.

5. Add 3 ml of purified water at 4° C. for each grain of original cell pellet weight (Step 2) and mix by inversion.

6. Incubate for 10 minutes on ice.

7. The lysed cells are pelleted by centrifugation at a minimum of 4,000×g for 15 minutes at room temperature.

8. The supernatant containing the periplasmic fraction is transferred to a clean tube.

9. To degrade contaminating nucleic acids, OmniCleave Endonuclease is optionally added to PeriPreps Lysis Buffer. Inclusion of a nuclease will generally improve the yield of protein and the ease of handling of the lysates, but addition of a nuclease is undesirable in some cases: for example, the use of a nuclease should be avoided if residual nuclease activity or transient exposure to the magnesium cofactor will interfere with subsequent assays or uses of the purified protein. The addition of EDTA to the lysate to inactivate OmniCleave Endonuclease, likewise, may interfere with subsequent assay or use of the purified protein. If nuclease is to be added, 2 microliters of OmniCleave Endonuclease and 10 microliters of 1.0 M $MgCl_2$ are diluted up to 1 ml with PeriPreps Lysis Buffer (10 mM Tris-HCl pH 7.5, 50 mM KCl, 1 mM EDTA, and 0.1% deoxycholate) for each milliliter of Lysis Buffer needed in Step 10.

10. The pellet is resuspended in 5 ml of PeriPreps Lysis Buffer for each gram of original cell pellet weight.

11. The pellet is incubated at room temperature for 10 minutes (if included, OmniCleave Endonuclease activity will cause a significant decrease in viscosity; the incubation is continued until the cellular suspension has the consistency of water).

12. The cellular debris is pelleted by centrifugation at a minimum of 4,000×g for 15 minutes at 4° C.

13. The supernatant containing the spheroplast fraction is transferred to a clean tube.

14. If OmniCleave Endonuclease was added to the PeriPreps Lysis Buffer, 20 microliters of 500 mM EDTA is added for each milliliter of the resultant spheroplastic fraction, to chelate the magnesium (the final concentration of EDTA in the lysate is 10 mM). Following hydrolysis of nucleic acids with OmniCleave Endonuclease, lysates may contain substantial amounts of mono- or oligonucleotides. The presence of these degradation products may affect further processing of the lysate: for example, nucleotides may decrease the binding capacity of anion exchange resins by interacting with the resin.

The above protocol can be used to prepare total cellular protein with the following modifications. The cells pelleted in Step 2 can be fresh or frozen; at Step 4, the cells are incubated for 15 minutes; Steps 5 through 8 are omitted; at Step 10, 3 ml of PeriPreps Lysis Buffer is added for each grain of original cell pellet weight.

After preparation of periplasmic, or spheroplastic, or whole-cell protein samples, the samples can be analyzed by any of a number of protein characterization and/or quantification methods. In one example, the successful fractionation of periplasmic and spheroplastic proteins is confirmed by analyzing an aliquot of both the periplasmic and spheroplastic fractions by SDS-PAGE (two microliters of each fraction is generally sufficient for visualization by staining with Coomassie Brilliant Blue). The presence of unique proteins or the enrichment of specific proteins in a given fraction indicates successful fractionation. For example, if the host cell contains a high-copy number plasmid with the ampicillin resistance marker, then the presence of β-lactamase (31.5 kDa) mainly in the periplasmic fraction indicates successful fractionation. Other *E. coli* proteins found in the periplasmic space include alkaline phosphatase (50 kDa) and elongation factor Tu (43 kDa). The amount of protein found in a given fraction can be quantified using any of a number of methods (such as SDS-PAGE and densitometry analysis of stained or labeled protein bands, scintillation counting of radiolabeled proteins, enzyme-linked immunosorbent assay (ELISA), or scintillation proximity assay, among other methods.) Comparing the amounts of a protein found in the periplasmic fraction as compared to the spheroplastic fraction indicates the degree to which the protein has been exported from the cytoplasm into the periplasm.

Example 10

Titration of Expression by Varying Inducer Concentration

To optimize production of a gene product using the expression systems of the invention, it is possible to independently adjust or titrate the concentrations of the inducers. Host cells containing expression constructs comprising inducible promoters—such as L-arabinose-inducible, propionate-inducible, L-rhamnose-inducible, or D-xylose-inducible promoters—are grown to the desired density for small-volume titrations (such as an $OD_{600}$ of approximately 0.5) in M9 minimal medium containing the appropriate antibiotics, then cells are aliquoted into small volumes of M9 minimal medium, optionally prepared with no carbon source such as glycerol, and with the appropriate antibiotics and varying concentrations of each inducer. Small-volume titrations can be performed in 200- to 500-ml shake flasks. The concentration of L-arabinose, L-rhamnose, or D-xylose necessary to induce expression is typically less (and is often substantially less) than 0.02% per OD unit of cells. In a titration experiment, the tested concentrations of L-arabinose can range from 2% to 1.5%, 1%, 0.5%, 0.2%, 0.1%, 0.05%, 0.04%, 0.03%, 0.02%, 0.01%, 0.005%, 0.002%, 0.001%, 0.0005%, 0.0002%, 0.0001%, 0.00005%, 0.00002%, 0.00001%, 0.000005%, 0.000002%, 0.000001%, 0.0000005%, 0.0000002%, 0.0000001%, 0.00000005%, 0.00000002%, and 0.00000001%, all per OD unit of cells. A concentration of 66.61 micromolar L-arabinose corresponds to 0.001% L-arabinose. An alternative titratation experiment for L-arabinose, L-rhamnose, or D-xylose would be to test the following concentrations, expressed in terms of molarity: 250 mM, 100 mM, 50 mM, 25 mM, 10 mM, 5 mM, 2.5 mM, 1.0 mM, 500 micromolar, 250 micromolar, 100 micromolar, 75 micromolar, 50 micromolar, 25 micromolar, 10 micromolar, 5.0 micromolar, 2.5 micromolar, 1.0 micromolar, 500 nM, 250 nM, 100 nM, 50 nM, 25 nM, 10 nM, 5.0 nM, 2.5 nM, 1.0 nM, 500 pM, 250 pM, 100 pM, 50 pM, 25 pM, 10 pM, 5.0 pM, 2.5 pM, and 1.0 pM, all per OD unit of cells. For propionate, concentrations to be tested can range from 1 M to 750 mM, 500 mM, 250 mM, 100 mM, 75 mM, 50 mM, 25 mM, 10 mM, 5 mM, 1 mM, 750 micromolar, 500 micromolar, 250 micromolar, 100 micromolar, 50 micromolar, 25 micromolar, 10 micromolar, 5.0 micromolar, 2.5 micromolar, 1.0 micromolar, 500 nM, 250 nM, 100 nM, 50 nM, 25 nM, 10 nM, 5.0 nM, 2.5 nM, and 1.0 nM all per OD unit of cells.

For each concentration 'x' of L-arabinose (or L-rhamnose or D-xylose) that is tested, the concentration of a different inducer such as propionate, added to each of the tubes containing concentration 'x' of the first inducer, is varied in each series of samples. Alternatively, titration experiments can start at a 'standard' combination of inducer concentrations, which for host cells having a reduced level of gene function of at least one gene encoding a protein that metabolizes the inducer is 0.0015% (100 micromolar) of any of L-arabinose, L-rhamnose, or D-xylose per OD unit of cells, and/or 100 micromolar propionate per OD unit of cells. For host cells in which the proteins that metabolize the inducer are functional, the 'standard' combination of inducer concentrations is 0.0033% (220 micromolar) of any of L-arabinose, L-rhamnose, or D-xylose per OD unit of cells, and/or 83 mM propionate per OD unit of cells. Additional combinations of inducer concentrations that vary from that of the 'standard' combination are tested; in a series of titration experiments, the results from initial experiments can be used to 'fine-tune' the inducer concentrations used in later experiments. Similar titration experiments can be performed with any combination of inducers used in an expression system of the invention, including but not limited to L-arabinose, propionate, L-rhamnose, and D-xylose. After growth in the presence of inducers for 6 hours, the cells are pelleted, the desired product is extracted from the cells, and the yield of product per mass value of cells is determined by a quantitative immunological assay such as ELISA, or by purification of the product and quantification by UV absorbance at 280 nm.

It is also possible to titrate inducer concentrations using a high-throughput assay, in which the proteins to be expressed are engineered to include a fluorescent protein moiety, such as that provided by the mKate2 red fluorescent protein (Evrogen, Moscow, Russia), or the enhanced green fluorescent proteins from *Aequorea victoria* and *Bacillus cereus*. Another approach to determining the amount and activity of gene products produced by different concentrations of inducers in a high-throughput titration experiment, is to use a sensor capable of measuring biomolecular binding interactions, such as a sensor that detects surface plasmon resonance, or a sensor that employs bio-layer interferometry (BLI) (for example, an Octet® QK system from forteBIO, Menlo Park, Calif.). If an antibody is available that binds with sufficient specificity to the gene product that is being expressed, the gene product can be detected and quantified using a capillary electrophoresis Western blot, such as that run on a WES system as described in Example 6.

Example 11

Determination of Polynucleotide or Amino Acid Sequence Similarity

Percent polynucleotide sequence or amino acid sequence identity is defined as the number of aligned symbols, i.e. nucleotides or amino acids, that are identical in both aligned sequences, divided by the total number of symbols in the alignment of the two sequences, including gaps. The degree of similarity (percent identity) between two sequences may be determined by aligning the sequences using the global alignment method of Needleman and Wunsch (*J. Mol. Biol.* 48:443, 1970), as implemented by the National Center for Biotechnology Information (NCBI) in the Needleman-Wunsch Global Sequence Alignment Tool, available through the website blast.ncbi.nlm.nih.gov/Blast.cgi. In one embodiment, the Needleman and Wunsch alignment parameters are set to the default values (Match/Mismatch Scores of 2 and −3, respectively, and Gap Costs for Existence and Extension of 5 and 2, respectively). Other programs used by those skilled in the art of sequence comparison may also be used to align sequences, such as, for example, the basic local alignment search tool or BLAST® program (Altschul et al., "Basic local alignment search tool", J Mol Biol 1990 Oct. 5; 215(3): 403-410), as implemented by NCBI, using the default parameter settings described at the blast.ncbi.nlm.nih.gov/Blast.cgi website. The BLAST algorithm has multiple optional parameters including two that may be used as follows: (A) inclusion of a filter to mask segments of the query sequence that have low compositional complexity or segments consisting of short-periodicity internal repeats, which is preferably not utilized or set to 'off', and (B) a statistical significance threshold for reporting matches against database sequences, called the 'Expect' or E-score (the expected probability of matches being found merely by chance; if the statistical significance ascribed to a match is greater than this E-score threshold, the match will not be reported). If this 'Expect' or E-score value is adjusted from the default value (10), preferred threshold values are 0.5, or in order of increasing preference, 0.25, 0.1, 0.05, 0.01, 0.001, 0.0001, 0.00001, and 0.000001.

In practicing the present invention, many conventional techniques in molecular biology, microbiology, and recombinant DNA technology are optionally used. Such conventional techniques relate to vectors, host cells, and recombinant methods. These techniques are well known and are explained in, for example, Berger and Kimmel, Guide to Molecular Cloning Techniques, Methods in Enzymology volume 152 Academic Press, Mc, San Diego, Calif.; Sambrook et al., Molecular Cloning—A Laboratory Manual (3rd Ed.), Vol. 1-3, Cold Spring Harbor Laboratory, Cold Spring Harbor, N.Y., 2000; and Current Protocols in Molecular Biology, F. M. Ausubel et al., eds., Current Protocols, a joint venture between Greene Publishing Associates, Inc. and John Wiley & Sons, Inc., (supplemented through 2006). Other useful references, for example for cell isolation and culture and for subsequent nucleic acid or protein isolation, include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg N.Y.); and Atlas and Parks (Eds.) The Handbook of Microbiological Media (1993) CRC Press, Boca Raton, Fla. Methods of making nucleic acids (for example, by in vitro amplification, purification from cells, or chemical synthesis), methods for manipulating nucleic acids (for example, by site-directed mutagenesis, restriction enzyme digestion, ligation, etc.), and various vectors, cell lines, and the like useful in manipulating and making nucleic acids are described in the above references. In addition, essentially any polynucleotide (including labeled or biotinylated polynucleotides) can be custom or standard ordered from any of a variety of commercial sources.

The present invention has been described in terms of particular embodiments found or proposed to comprise certain modes for the practice of the invention. It will be appreciated by those of ordinary skill in the art that, in light of the present disclosure, numerous modifications and changes can be made in the particular embodiments exemplified without departing from the intended scope of the invention.

All cited references, including patent publications, are incorporated herein by reference in their entirety. Nucleotide and other genetic sequences, referred to by published genomic location or other description, are also expressly incorporated herein by reference.

SEQUENCES PRESENTED IN THE SEQUENCE LISTING

| SEQ ID NO: | Length: | Type: | Organism: | Description; 'Other Information' |
|---|---|---|---|---|
| 1 | 21 | PRT | *Homo sapiens* | Native human insulin, A chain |
| 2 | 30 | PRT | *Homo sapiens* | Native human insulin, B chain |
| 3 | 30 | PRT | Artificial Sequence | Insulin lispro, B chain |
| 4 | 30 | PRT | Artificial Sequence | Insulin aspart, B chain |
| 5 | 30 | PRT | Artificial Sequence | Insulin glulisine, B chain |
| 6 | 21 | PRT | Artificial Sequence | Insulin glargine, A chain |
| 7 | 32 | PRT | Artificial Sequence | Insulin glargine, B chain |
| 8 | 29 | PRT | Artificial Sequence | Insulin degludec, B chain; modification of lysine at B29 with a hexadecanedioic acid molecule bound to B29 through an L-gamma-Glu linker |
| 9 | 29 | PRT | Artificial Sequence | Insulin detemir, B chain; modification of lysine at B29 with a myristic acid molecule |
| 10 | 35 | PRT | *Homo sapiens* | The C-peptide of human insulin |
| 11 | 9 | PRT | Artificial Sequence | Artificial C-peptide |
| 12 | 34 | PRT | Artificial Sequence | Artificial variant of the human C-peptide |
| 13 | 25 | PRT | Artificial Sequence | Artificial variant of the human C-peptide |
| 14 | 8 | PRT | Artificial Sequence | Artificial C-peptide |
| 15 | 147 | PRT | Artificial Sequence | Metreleptin |
| 16 | 168 | PRT | Hog cholera virus (strain Alfort) | Hog cholera virus/classical swine fever virus (CSFV) $N^{pro}$ |
| 17 | 91 | PRT | *Caenorhabditis elegans* | Small ubiquitin-related modifier (SUMO) |
| 18 | 26 | PRT | Artificial Sequence | Linker polypeptide |
| 19 | 50 | PRT | Artificial Sequence | Linker polypeptide |
| 20 | 7 | PRT | Artificial Sequence | Acid-cleavable amino acid sequence |
| 21 | 8 | PRT | Artificial Sequence | TEV (tobacco etch virus) protease cleavage site |
| 22 | 6 | PRT | Artificial Sequence | Enterokinase cleavage site |
| 23 | 6 | PRT | Artificial Sequence | Thrombin cleavage site |
| 24 | 396 | PRT | *Escherichia coli* | Maltose binding protein (MBP) |
| 25 | 169 | PRT | *Thermotoga maritima* | Family 9 carbohydrate-binding module from *Thermotoga maritima* xylanase 10a (CBM9) |
| 26 | 95 | PRT | *Homo sapiens* | Carboxypeptidase B propeptide |
| 27 | 44 | PRT | Artificial Sequence | Carboxypeptidase B propeptide variant |
| 28 | 51 | PRT | Artificial Sequence | Carboxypeptidase B propeptide variant |

-continued

SEQUENCES PRESENTED IN THE SEQUENCE LISTING

| SEQ ID NO: | Length: | Type: | Organism: | Description; 'Other Information' |
|---|---|---|---|---|
| 29 | 51 | PRT | Artificial Sequence | Carboxypeptidase B propeptide variant |
| 30 | 53 | PRT | Artificial Sequence | Carboxypeptidase B propeptide variant |
| 31 | 53 | PRT | Artificial Sequence | Carboxypeptidase B propeptide variant |
| 32 | 58 | PRT | Artificial Sequence | Carboxypeptidase B propeptide variant |
| 33 | 48 | PRT | Artificial Sequence | Carboxypeptidase B propeptide variant with acid-cleavable Asp-Pro sequence |
| 34 | 48 | PRT | Artificial Sequence | Carboxypeptidase B propeptide variant with acid-cleavable Asp-Pro sequence |
| 35 | 51 | PRT | Artificial Sequence | Carboxypeptidase B propeptide variant with acid-cleavable Asp-Pro sequence |
| 36 | 18 | PRT | Artificial Sequence | Carboxypeptidase B propeptide variant |
| 37 | 8 | PRT | Artificial Sequence | Artificial propeptide |
| 38 | 189 | PRT | *S. cerevisiae* | *Saccharomyces cerevisiae* (strain S288c) Erv1p |
| 39 | 191 | PRT | Artificial Sequence | CPBpro variant attached to N-terminus of metreleptin |
| 40 | 486 | PRT | Artificial Sequence | *Humicola insolens* protein disulfide isomerase (PDI), without signal peptide |
| 41 | 1487 | DNA | Artificial Sequence | Polynucleotide encoding *Humicola insolens* PDI without signal peptide |
| 42 | 5304 | DNA | Artificial Sequence | Dual-promoter vector, pSOL |
| 43 | 104 | PRT | Artificial Sequence | CPBpro variant lispro proinsulin polypeptide PN2.5 |
| 44 | 329 | DNA | Artificial Sequence | Polynucleotide encoding CPBpro variant lispro proinsulin polypeptide PN2.5 |
| 45 | 111 | PRT | Artificial Sequence | CPBpro variant lispro proinsulin polypeptide PN2.6 |
| 46 | 350 | DNA | Artificial Sequence | Polynucleotide encoding CPBpro variant lispro proinsulin polypeptide PN2.6 |
| 47 | 111 | PRT | Artificial Sequence | CPBpro variant lispro proinsulin polypeptide PN2.7 |
| 48 | 350 | DNA | Artificial Sequence | Polynucleotide encoding CPBpro variant lispro proinsulin polypeptide PN2.7 |
| 49 | 113 | PRT | Artificial Sequence | CPBpro variant lispro proinsulin polypeptide PN2.8 |
| 50 | 356 | DNA | Artificial Sequence | Polynucleotide encoding CPBpro variant lispro proinsulin polypeptide PN2.8 |
| 51 | 113 | PRT | Artificial Sequence | CPBpro variant lispro proinsulin polypeptide PN2.9 |
| 52 | 356 | DNA | Artificial Sequence | Polynucleotide encoding CPBpro variant lispro proinsulin polypeptide PN2.9 |

-continued

SEQUENCES PRESENTED IN THE SEQUENCE LISTING

| SEQ ID NO: | Length: | Type: | Organism: | Description; 'Other Information' |
|---|---|---|---|---|
| 53 | 118 | PRT | Artificial Sequence | CPBpro variant lispro proinsulin polypeptide PN2.10 |
| 54 | 371 | DNA | Artificial Sequence | Polynucleotide encoding CPBpro variant lispro proinsulin polypeptide PN2.10 |
| 55 | 104 | PRT | Artificial Sequence | CPBpro variant glargine proinsulin polypeptide PN3.13 |
| 56 | 329 | DNA | Artificial Sequence | Polynucleotide encoding CPBpro variant glargine proinsulin polypeptide PN3.13 |
| 57 | 570 | DNA | Artificial Sequence | Polynucleotide encoding *Saccharomyces cerevisiae* (strain S288c) Erv1p |
| 58 | 13 | PRT | *Homo sapiens* | Fragment of insulin A chain |
| 59 | 12 | PRT | *Homo sapiens* | Fragment of insulin B chain |
| 60 | 4 | PRT | *Homo sapiens* | Fragment of insulin A chain |
| 61 | 8 | PRT | *Homo sapiens* | Fragment of insulin B chain |
| 62 | 108 | PRT | Artificial Sequence | CPBpro variant glargine proinsulin polypeptide PN3.15 |
| 63 | 359 | DNA | Artificial Sequence | Polynucleotide encoding CPBpro variant glargine proinsulin polypeptide PN3.15 |
| 64 | 108 | PRT | Artificial Sequence | CPBpro variant glargine proinsulin polypeptide PN3.16 |
| 65 | 359 | DNA | Artificial Sequence | Polynucleotide encoding CPBpro variant glargine proinsulin polypeptide PN3.16 |
| 66 | 111 | PRT | Artificial Sequence | CPBpro variant glargine proinsulin polypeptide PN3.17 |
| 67 | 368 | DNA | Artificial Sequence | Polynucleotide encoding CPBpro variant glargine proinsulin polypeptide PN3.17 |
| 68 | 103 | PRT | Artificial Sequence | Variant glargine proinsulin polypeptide PN3.62 |
| 69 | 77 | PRT | Artificial Sequence | Variant glargine proinsulin polypeptide PN3.116 |
| 70 | 93 | PRT | Artificial Sequence | Variant glargine proinsulin polypeptide PN3.165 |
| 71 | 94 | PRT | Artificial Sequence | Variant glargine proinsulin polypeptide PN3.172 |
| 72 | 84 | PRT | Artificial Sequence | Variant glargine proinsulin polypeptide PN3.185 |
| 73 | 23 | PRT | Artificial Sequence | Artificial variant of the human C-peptide: amino acids 3-25 of SEQ ID NO: 13 |
| 74 | 6 | PRT | Artificial Sequence | Artificial C-peptide: amino acids 3-8 of SEQ ID NO: 14 |

What is claimed is:

1. A connecting polypeptide comprising SEQ ID NO:73.

2. A proinsulin polypeptide comprising:

a mature insulin A-chain;

a mature insulin B-chain; and a connecting peptide comprising SEQ ID NO:73 linking the mature A-chain and the mature B-chain, wherein the connecting peptide is not a native human proinsulin C-peptide.

3. The proinsulin polypeptide of claim 2, wherein the mature insulin A-chain is selected from the group consisting of SEQ ID NO:1 and SEQ ID NO:6.

4. The proinsulin polypeptide of claim 3, wherein the mature insulin A-chain comprises SEQ ID NO:6.

5. The proinsulin polypeptide of claim 2, wherein the mature insulin B-chain is selected from the group consisting of SEQ ID NO:2, SEQ ID NO:3, SEQ ID NO:4, SEQ ID NO:5, SEQ ID NO:7, SEQ ID NO:8, and SEQ ID NO:9.

6. The proinsulin polypeptide of claim 5, wherein the mature insulin B-chain comprises SEQ ID NO:7.

7. The proinsulin polypeptide of claim 2, wherein the proinsulin polypeptide lacks a signal peptide.

8. The proinsulin polypeptide of claim 2, further comprising a carboxypeptidase B propeptide coupled to the N-terminal residue of the mature insulin B-chain, the carboxypeptidase B propeptide selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36.

9. The proinsulin polypeptide of claim 8, wherein the carboxypeptidase B propeptide comprises SEQ ID NO:36.

10. The proinsulin polypeptide of claim 2, further comprising a propeptide coupled to the N-terminal residue of the mature insulin B-chain, wherein the propeptide is SEQ ID NO:37.

11. An expression construct comprising a polynucleotide sequence encoding the insulin polypeptide of claim 2.

12. A host cell comprising the expression construct of claim 11.

13. A proinsulin polypeptide comprising:

a mature insulin A-chain comprising SEQ ID NO:6;

a mature insulin B-chain comprising SEQ ID NO:7; and a connecting peptide comprising SEQ ID NO: 73 linking the mature A-chain and the mature B-chain, wherein the connecting peptide is not a native human proinsulin C-peptide.

14. The proinsulin polypeptide of claim 13, wherein the proinsulin polypeptide lacks a signal peptide.

15. The proinsulin polypeptide of claim 13, further comprising a carboxypeptidase B propeptide coupled to the N-terminal residue of the mature insulin B-chain, the carboxypeptidase B propeptide selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36.

16. The proinsulin polypeptide of claim 15, wherein the carboxypeptidase B propeptide comprises SEQ ID NO:36.

17. An expression construct comprising a polynucleotide sequence encoding the insulin polypeptide of claim 13.

18. A host cell comprising the expression construct of claim 17.

19. A proinsulin polypeptide comprising:

a mature insulin A-chain comprising SEQ ID NO:6;

a mature insulin B-chain comprising SEQ ID NO:7;

a connecting peptide comprising SEQ ID NO:73 linking the mature A-chain and the mature B-chain, wherein the connecting peptide is not a native human proinsulin C-peptide; and a carboxypeptidase B propeptide coupled to the N-terminal residue of the mature insulin B-chain, the carboxypeptidase B propeptide comprising SEQ ID NO:36.

20. The proinsulin polypeptide of claim 19, wherein the proinsulin polypeptide lacks a signal peptide.

* * * * *

UNITED STATES PATENT AND TRADEMARK OFFICE
CERTIFICATE OF CORRECTION

| | | |
|---|---|---|
| PATENT NO. | : 11,584,785 B2 | Page 1 of 1 |
| APPLICATION NO. | : 16/866361 | |
| DATED | : February 21, 2023 | |
| INVENTOR(S) | : Amy Doerner et al. | |

It is certified that error appears in the above-identified patent and that said Letters Patent is hereby corrected as shown below:

On the Title Page

At item (57), Lines 3-4, "SEQ ID NO: 73" should be -- SEQ ID NO:73 --.

In the Claims

At Column 117, Line 19, "SEQ ID NO: 73" should be -- SEQ ID NO:73 --.

Signed and Sealed this
Seventh Day of November, 2023

*Katherine Kelly Vidal*

Katherine Kelly Vidal
*Director of the United States Patent and Trademark Office*